US007732457B2

(12) United States Patent
Malamas et al.

(10) Patent No.: US 7,732,457 B2
(45) Date of Patent: Jun. 8, 2010

(54) AMINO-PYRIDINES AS INHIBITORS OF β-SECRETASE

(75) Inventors: Michael Sotirios Malamas, Jamison, PA (US); William Floyd Fobare, Lawrenceville, NJ (US); William Ronald Solvibile, Jr., East Windsor, NJ (US); Frank Eldridge Lovering, Acton, MA (US); Jeffrey Scott Condon, Cambridge, MA (US); Albert Jean Robichaud, Ringoes, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/344,432

(22) Filed: Jan. 31, 2006

(65) Prior Publication Data

US 2006/0173049 A1   Aug. 3, 2006

Related U.S. Application Data

(60) Provisional application No. 60/649,068, filed on Feb. 1, 2005.

(51) Int. Cl.
*A61K 31/506* (2006.01)
*C07D 401/14* (2006.01)
(52) U.S. Cl. ..................... 514/269; 544/298
(58) Field of Classification Search ............... 544/298; 514/269
See application file for complete search history.

(56) References Cited

U.S. PATENT DOCUMENTS

| | | | |
|---|---|---|---|
| 4,140,793 | A | 2/1979 | Ward |
| 4,225,613 | A | 9/1980 | Ward |
| 6,054,457 | A | 4/2000 | Setoi et al. |
| 6,399,824 | B1 | 6/2002 | Hofmeister et al. |
| 6,656,957 | B1 | 12/2003 | Allgeier et al. |
| 6,689,804 | B2 | 2/2004 | Wu et al. |
| 6,974,829 | B2 | 12/2005 | Tung et al. |
| 7,285,682 | B2 | 10/2007 | Hu |
| 2005/0282825 | A1 | 12/2005 | Malamas et al. |
| 2005/0282826 | A1 | 12/2005 | Malamas et al. |
| 2006/0111370 | A1 | 5/2006 | Zhu et al. |
| 2006/0160828 | A1 | 7/2006 | Malamas et al. |
| 2006/0183790 | A1 | 8/2006 | Cole et al. |
| 2006/0183792 | A1 | 8/2006 | Fobare et al. |
| 2007/0004730 | A1 | 1/2007 | Zhou |
| 2007/0004786 | A1 | 1/2007 | Malamas et al. |
| 2007/0027199 | A1 | 2/2007 | Malamas et al. |
| 2007/0072925 | A1 | 3/2007 | Malamas et al. |
| 2007/0191431 | A1 | 8/2007 | Zhou |
| 2007/0203116 | A1 | 8/2007 | Quagliato et al. |
| 2008/0051390 | A1 | 2/2008 | Malamas et al. |

FOREIGN PATENT DOCUMENTS

| | | |
|---|---|---|
| EP | 0861831 A1 | 9/1998 |
| GB | 2013192 A | 8/1979 |
| WO | WO 97/45417 A1 | 12/1997 |
| WO | WO 98/45267 | 10/1998 |
| WO | WO 01/87829 A1 | 11/2001 |
| WO | WO 03/053938 A1 | 7/2003 |
| WO | WO 03/064396 A1 | 8/2003 |
| WO | WO 03/094854 A2 | 11/2003 |
| WO | WO 2004/058727 A1 | 7/2004 |
| WO | WO 2005/005412 A1 | 1/2005 |
| WO | WO 2005/058311 A1 | 6/2005 |
| WO | WO 2006/009653 A1 | 1/2006 |
| WO | WO 2006/065277 A2 | 6/2006 |
| WO | WO 2007/005404 A1 | 1/2007 |
| WO | WO 2007/016012 A2 | 2/2007 |

OTHER PUBLICATIONS

Rips et al., "1,2,5-trisubstiuted, etc." J. Org. Chem., 1960, 25(3), 390-392.*
Abbott et al., Molecular Medicine Today, 1996, vol. 2, p. 106-113.
Allimony et al., "Synthesis and antimicrobial activity of some nitrogen heterobicyclic systems: Part I", Indian Journal of Chemistry, 1999, vol. 38B, pp. 445-451.
Fact Sheet Alzheimer's Association, 2006.
Lefrance-Jullien et al., "Design and characterization of a new cell-permeant inhibitor of the beta-secretase BACE1", British Journal of Pharmacology, 2005, vol. 145, pp. 228-235.
Lyketsos et al., "Position statement of the American Association for Geriatric Psychiatry regarding principles of care for patients with dementia resulting from Alzheimer's Disease", 2006, vol. 14, pp. 561-573.
Alzheimer's Disease, retrieved from internet on Jun. 27, 2007, http://www.mayoclinic.com/health/alzheimers-disease/DA00161/DSECTION-3.
National Institute of Neurological Discorders and Stroke, "Alzheimer's Disease Information Page", retrieved from internet on Jun. 27, 2007, http://www.ninds.nih.gov/disorders/alzheimersdisease/alzheimersdisease.htm.
PCT Preliminary Report on Patentability, Written Opinion of the ISR, International Patent Application PCT/US2006/024793, International filing date Jun. 26, 2006.

(Continued)

Primary Examiner—Patricia L Morris
(74) Attorney, Agent, or Firm—Ram W. Sabnis

(57) ABSTRACT

The present invention provides an amino-pyridine compound of formula I

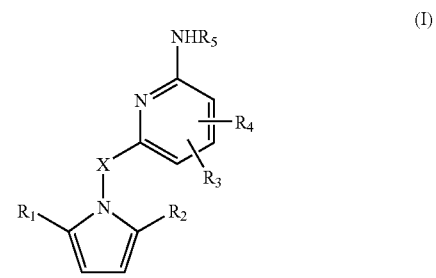

(I)

The present invention also provides methods for the use thereof to inhibit β-secretase (BACE) and treat β-amyloid deposits and neurofibrillary tangles.

9 Claims, No Drawings

OTHER PUBLICATIONS

PCT Preliminary Report on Patentability, Written Opinion of the ISR, International Patent Application PCT/US2006/024912, International filing date Jun. 26, 2006.

Selkoe, "Alzheimer's Disease: Genes, Proteins, and Therapy", Physiological Reviews, 2001, vol. 81(2), pp. 741-766.

Su et al. "Drug delivery across the blood-brain barrier: why is it difficult? How to measure and improve it?", Expert Opinion on Drug Delivery, Abstract, 2006, vol. 3, pp. 419-425.

Tao et al., "Synthesis of Conformationally constrained spirohydantoins with a Dibenzo[a,d]heptadiene ring", Synthesis 2000, No. 10, pp. 1449-1453.

Vandana et al., "Transferring coupled liposomes as drug delivery carriers for brain trageting of 5-florouracil", Journal of Drug Targeting, Abstract, 2005, vol. 13 pp. 245-250.

Varghese et al., "Human beta-secretase (BACE) and BACE Inhibitors", J. Med. Chem. 2003, vol. 46(22), pp. 4625-4630.

Xiao et al., "An improved procedure for the synthesis of 4,4-disubstituted-3-oxo-1,2,5-thiadiazolidine 1,1-dioxides", J. Heterocyclic Chem., 2000, vol. 37, pp. 773-777.

Yamada et al., "Hydantoin derivatives, I. Actions on central nervous system of 5,5-diarylhydantoins and 5,5-diarylhydantion-2-imines", Abstract, Oyo Yakuri, 1975, vol. 9(6), pp. 841-847.

* cited by examiner

AMINO-PYRIDINES AS INHIBITORS OF β-SECRETASE

This application claims the benefit under 35 U.S.C. §119 (e) to U.S. Provisional Application No. 60/649,068, filed Feb. 1, 2005, which is hereby incorporated by reference in its entirety.

BACKGROUND OF THE INVENTION

β-amyloid deposits and neurofibrillary tangles are two major pathologic characterizations associated with Alzheimer's disease (AD). Clinically, AD is characterized by the of loss of memory, cognition, reasoning, judgment, and orientation. Also affected, as the disease progresses, are motor, sensory, and linguistic abilities until global impairment of multiple cognitive functions occurs. These cognitive losses take place gradually, but typically lead to severe impairment and eventual death in 4-12 years.

Amyloidogenic plaques and vascular amyloid angiopathy also characterize the brains of patients with Trisomy 21 (Down's Syndrome), Hereditary Cerebral Hemorrhage with Amyloidosis of the Dutch-type (HCHWA-D), and other neurodegenerative disorders. Neurofibrillary tangles also occur in other neurodegenerative disorders including dementia-inducing disorders (Varghese, J., et al, Journal of Medicinal Chemistry, 2003, 46, 4625-4630).

β-amyloid deposits are predominately an aggregate of Aβ peptide, which in turn is a product of the proteolysis of amyloid precursor protein (APP). More specifically, Aβ peptide results from the cleavage of APP at the C-terminus by one or more β-secretases, and at the N-terminus by β-secretase enzyme (BACE), also known as aspartyl protease, as part of the β-amyloidogenic pathway.

BACE activity is correlated directly to the generation of Aβ peptide from APP (Sinha, et al, Nature, 1999, 402, 537-540), and studies increasingly indicate that the inhibition of BACE inhibits the production of Aβ peptide (Roberds, S. L., et al, Human Molecular Genetics, 2001, 10, 1317-1324).

Therefore, it is an object of this invention to provide compounds which are inhibitors of β-secretase and are useful as therapeutic agents in the treatment, prevention or amelioration of a disease or disorder characterized by elevated β-amyloid deposits or β-amyloid levels in a patient.

It is another object of this invention to provide therapeutic methods and pharmaceutical compositions useful for the treatment, prevention or amelioration of a disease or disorder characterized by elevated β-amyloid deposits or β-amyloid levels in a patient.

It is a feature of this invention that the compounds provided may also be useful to further study and elucidate the p-secretase enzyme.

These and other objects and features of the invention will become more apparent by the detailed description set forth hereinbelow.

SUMMARY OF THE INVENTION

The present invention provides a compound of formula I

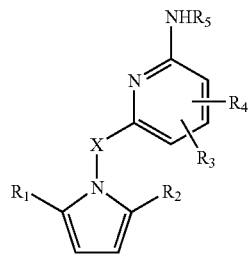

(I)

wherein
X is $CH_2$ or NR;
R is H or alkyl;
$R_1$ and $R_2$ are each independently an alkyl, cycloalkyl, cycloheteroalkyl, phenyl or heteroaryl group each group optionally substituted;
$R_3$ and $R_4$ are each independently H, halogen, $NR_6R_7$, $OR_8$, or an alkyl, haloalkyl or aryl group each group optionally substituted;
$R_5$ is H or an alkyl or haloalkyl group each optionally substituted;
$R_6$ and $R_7$ are each independently H or an optionally substituted alkyl group; and
$R_8$ is H or an alkyl or alkenyl group each group optionally substituted; or
a pharmaceutically acceptable salt thereof.

The present invention also relates to the use of the formula I amino-pyridine compound for the treatment of β-amyloid deposits and neurofibrillary tangles. The compound of the invention is particularly useful for treating Alzheimer's disease, cognitive impairment, Down's Syndrome, HCHWA-D, cognitive decline, senile dementia, cerebral amyloid angiopathy, degenerative dementia, or other neurodegenerative disorders.

DETAILED DESCRIPTION OF THE INVENTION

Alzheimer's disease (AD) is a major degenerative disease of the brain which presents clinically by progressive loss of memory, cognition, reasoning, judgement and emotional stability and gradually leads to profound mental deterioration and death. The exact cause of AD is unknown, but increasing evidence indicates that amyloid beta peptide (A-beta) plays a central role in the pathogenesis of the disease. (D. B. Schenk; R. E. Rydel et al, Journal of Medicinal Chemistry, 1995, 21, 4141 and D. J. Selkoe, Physiology Review, 2001, 81, 741). Patients with AD exhibit characteristic neuropathological markers such as neuritic plaques (and in β-amyloid angiopathy, deposits in cerebral blood vessels) as well as neurofibrillary tangles detected in the brain at autopsy. A-beta is a major component of neuritic plaques in AD brains. In addition, β-amyloid deposits and vascular β-amyloid angiopathy also characterize individuals with Downs Syndrome, Hereditary Cerebral Hemorrhage with Amyloidosis of the Dutch type and other neurodegenerative and dementia-inducing disorders. Over expression of the amyloid precursor protein (APP), altered cleavage of APP to A-beta or a decrease in the clearance of A-beta from a patient's brain may increase the levels of soluble or fibrillar forms of A-beta in the brain. The β-site APP cleaving enzyme, BACE1, also called memapsin-2 or Asp-2, was identified in 1999 (R. Vassar, B. D. Bennett, et al., Nature, 1999, 402, 537). BACE1 is a membrane-bound aspartic protease with all the known functional properties and characteristics of β-secretase. Low molecular weight, non-peptide, non-substrate-related inhibitors of BACE1 or β-secretase are earnestly sought both as an aid in the study of the β-secretase enzyme and as potential therapeutic agents.

Surprisingly, it has now been found that amino-pyridine compounds of formula I demonstrate inhibition of β-secretase and the selective inhibition of BACE1. Advantageously, said amino-pyridine compounds may be used as effective therapeutic agents for the treatment, prevention or amelioration of a disease or disorder characterized by elevated p-amyloid deposits or β-amyloid levels in a patient. Accordingly, the present invention provides an amino-pyridine compound of formula I

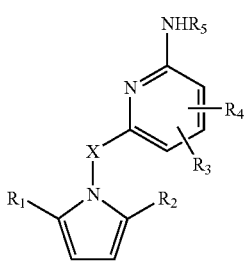

wherein
X is CH$_2$ or NR;
R is H or alkyl;
R$_1$ and R$_2$ are each independently an alkyl, cycloalkyl, cycloheteroalkyl, phenyl or heteroaryl group each group optionally substituted;
R$_3$ and R$_4$ are each independently H, halogen, NR$_6$R$_7$, OR$_8$, or an alkyl, haloalkyl or aryl group each group optionally substituted;
R$_5$ is H or an alkyl or haloalkyl group each optionally substituted;
R$_6$ and R$_7$ are each independently H or an optionally substituted alkyl group; and
R$_8$ is H or an alkyl or alkenyl group each group optionally substituted; or a pharmaceutically acceptable salt thereof.

Preferred compounds of formula I are those compounds having the structure of formula Ia

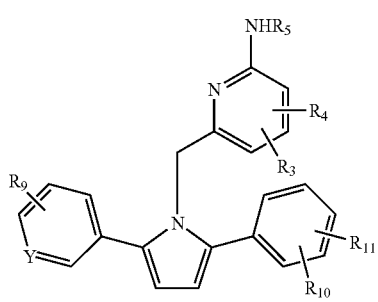

wherein
Y is CR$_{12}$ or N;
R$_3$, R$_4$ and R$_5$ are as defined for formula I hereinabove;
R$_9$ is H, halogen, OR$_{12}$, CO$_2$R$_{12}$, CONHR$_{12}$, NHCOR$_{12}$, or an alkyl, haloalkyl, aryl or heteroaryl group each group optionally substituted;
R$_{10}$ and R$_{11}$ are each independently H, halogen, OR$_{13}$, or an alkyl or haloalkyl group each group optionally substituted; and
R$_{12}$ and R$_{13}$ are each independently H or an optionally substituted alkyl, haloalkyl, cycloheteroalkyl, aryl or heteroaryl group each group optionally substituted.

It is understood that the claims encompass all possible stereoisomers and prodrugs. Moreover, unless stated otherwise, each alkyl, alkenyl, alkynyl, cycloalkyl cycloheteroalkyl, aryl or heteroaryl group is contemplated as being optionally substituted.

An optionally substituted moiety may be substituted with one or more substituents. The substituent groups which are optionally present may include halogen atoms, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy, heterocyclyl or cycloalkyl groups, preferably halogen atoms or lower alkyl or lower alkoxy groups. Unless otherwise specified, typically, 0-4 substituents may be present. When any of the foregoing substituents represents or contains an alkyl substituent group, this may be linear or branched and may contain up to 12 carbon atoms, preferably up to 6 carbon atoms, more preferably up to 4 carbon atoms.

As used herein, the term "alkyl" includes both (C$_1$-C$_{10}$) straight chain and (C$_3$-C$_{12}$) branched-chain (unless defined otherwise) monovalent saturated hydrocarbon moiety. Examples of saturated hydrocarbon alkyl moieties include, but are not limited to, chemical groups such as methyl, ethyl, n-propyl, isopropyl, n-butyl, tert-butyl, isobutyl, sec-butyl; higher homologs such as n-pentyl, n-hexyl, and the like. Specifically included within the definition of "alkyl" are those alkyl groups that are optionally substituted. Suitable alkyl substitutions include, but are not limited to, CN, OH, halogen, phenyl, carbamoyl, carbonyl, alkoxy or aryloxy.

As used herein the term "haloalkyl" designates a C$_n$H$_{2n+1}$ group having from one to 2n+1 halogen atoms which may be the same or different. Examples of haloalkyl groups include CF$_3$, CH$_2$C$_1$, C$_2$H$_3$BrCl, C$_3$H$_5$F$_2$, or the like.

The term "alkenyl", as used herein, refers to either a (C$_2$-C$_8$) straight chain or (C$_3$-C$_{10}$) branched-chain monovalent hydrocarbon moiety containing at least one double bond. Such hydrocarbon alkenyl moieties may be mono or polyunsaturated, and may exist in the E or Z configurations. The compounds of this invention are meant to include all possible E and Z configurations. Examples of mono or polyunsaturated hydrocarbon alkenyl moieties include, but are not limited to, chemical groups such as vinyl, 2-propenyl, isopropenyl, crotyl, 2-isopentenyl, butadienyl, 2-(butadienyl), 2,4-pentadienyl, 3-(1,4-pentadienyl), and higher homologs, isomers, or the like.

The term "cycloalkyl", as used herein, refers to a monocyclic, bicyclic, tricyclic, fused, bridged, or spiro monovalent saturated hydrocarbon moiety of 3-10 carbon atoms, unless otherwise specified, wherein the carbon atoms are located inside or outside of the ring system. Any suitable ring position of the cycloalkyl moiety may be covalently linked to the defined chemical structure. Examples of cycloalkyl moieties include, but are not limited to, chemical groups such as cyclopropyl, cyclopropylmethyl, cyclobutyl, cyclopentyl, cyclohexyl, cyclohexylmethyl, cyclohexylethyl, cycloheptyl, norbornyl, adamantyl, spiro[4.5]decanyl, and homologs, isomers, or the like.

The term "cycloheteroalkyl" as used herein designates a 5- to 7-membered cycloalkyl ring system containing 1, 2 or 3 heteroatoms, which may be the same or different, selected from N, O or S and optionally containing one double bond. Exemplary of the cycloheteroalkyl ring systems included in the term as designated herein are the following rings wherein X$_1$ is NR', O or S and R is H or an optional substituent as defined hereinbelow.

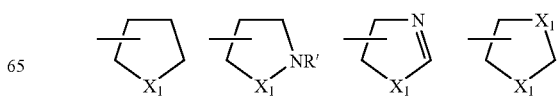

-continued

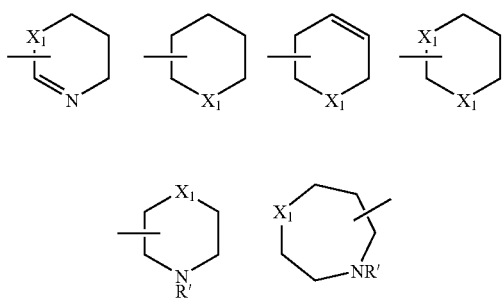

The term "aryl", as used herein, refers to an aromatic carbocyclic moiety of up to 20 carbon atoms, which may be a single ring (monocyclic) or multiple rings (bicyclic, up to three rings) fused together or linked covalently. Any suitable ring position of the aryl moiety may be covalently linked to the defined chemical structure. Examples of aryl moieties include, but are not limited to, chemical groups such as phenyl, 1-naphthyl, 2-naphthyl, dihydronaphthyl, tetrahydronaphthyl, biphenyl, anthryl, phenanthryl, fluorenyl, indanyl, biphenylenyl, acenaphthenyl, acenaphthylenyl, and the like. The term "aryl" further includes both unsubstituted carbocyclic groups and carbocyclic groups containing 1-5-substitutions.

The term "heteroaryl" as used herein means an aromatic heterocyclic ring system, which may be a single ring (monocyclic) or multiple rings (bicyclic, up to three rings) fused together or linked covalently. Preferably, heteroaryl is a 5- to 6-membered ring. The rings may contain from one to four hetero atoms selected from nitrogen, oxygen, or sulfur, wherein the nitrogen or sulfur atom(s) are optionally oxidized, or the nitrogen atom(s) are optionally quarternized. Any suitable ring position of the heteroaryl moiety may be covalently linked to the defined chemical structure. Examples of heteroaryl moieties include, but are not limited to, heterocycles such as furan, thiophene, pyrrole, N-methylpyrrole, pyrazole, N-methylpyrazole, imidazole, N-methylimidazole, oxazole, isoxazole, thiazole, isothiazole, 1H-tetrazole, 1-methyltetrazole, 1,3,4-oxadiazole, 1H-1,2,4-triazole, 1-methyl-1,2,4-triazole 1,3,4-triazole, 1-methyl-1,3,4-triazole, pyridine, pyrimidine, pyrazine, pyridazine, benzoxazole, benzisoxazole, benzothiazole, benzofuran, benzothiophene, thianthrene, dibenzo[b,d]furan, dibenzo[b,d]thiophene, benzimidazole, N-methylbenzimidazole, indole, indazole, quinoline, isoquinoline, quinazoline, quinoxaline, purine, pteridine, 9H-carbazole, α-carboline, or the like.

The term "halogen", as used herein, designates fluorine, chlorine, bromine, and iodine.

The compounds of the present invention may be converted to salts, in particular pharmaceutically acceptable salts using art recognized procedures. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono-, di- or tri-$C_1$-$C_6$alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Salts which are unsuitable for pharmaceutical uses but which can be employed, for example, for the isolation or purification of free compounds or their pharmaceutically acceptable salts, are also included. The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The compounds of this invention may contain an asymmetric carbon atom and some of the compounds of this invention may contain one or more asymmetric centers and may thus give rise to optical isomers and diastereomers. While shown without respect to stereochemistry in Formula I, the present invention includes such optical isomers and diastereomers; as well as the racemic and resolved, enantiomerically pure R and S stereoisomers; as well as other mixtures of the R and S stereoisomers and pharmaceutically acceptable salts thereof. Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one stereoisomer, preferably less than about 50%, more preferably less than about 75%, and even more preferably less than about 90%.

Preferred compounds of formula I are those compounds wherein X is $CH_2$ and $R_5$ is H. Another group of preferred compounds are those compounds of formula I wherein $R_1$ is an optionally substituted cycloalkyl or phenyl group and $R_2$ is an optionally substituted phenyl or heteroaryl. Also preferred are those compounds of formula I having the structure of formula Ia

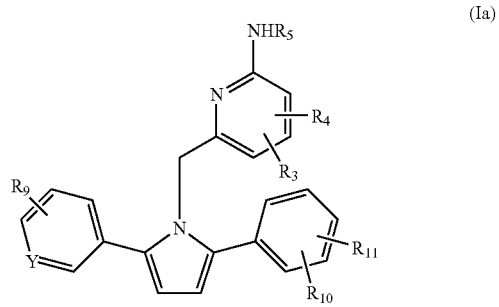

(Ia)

wherein
Y is $CR_{12}$ or N;
$R_3$, $R_4$ and $R_5$ are as defined for formula I hereinabove;
$R_9$ is H, halogen, $OR_{12}$, $CO_2R_{12}$, $CONHR_{12}$, $NHCOR_{12}$, or an alkyl, haloalkyl, aryl or heteroaryl group each group optionally substituted;
$R_{10}$ and $R_{11}$, are each independently H, halogen, $OR_{13}$, or an alkyl or haloalkyl group each group optionally substituted; and $R_{12}$ and $R_{13}$ are each independently H or an optionally substituted alkyl, haloalkyl, cycloheteroalkyl, aryl or heteroaryl group each group optionally substituted.

More preferred compounds of the invention are those compounds of formula Ia wherein $R_3$ is attached in the ring position ortho to the $NHR_5$ group and $R_4$ and $R_5$ are H. Another group of more preferred compounds of the invention are those compounds of formula Ia wherein $R_{10}$ is H, halogen or an optionally substituted alkyl or alkoxy group and $R_4$, $R_5$ and $R_{11}$ are H. A further group of more preferred compounds of the invention are those compounds of formula Ia wherein Y is CH; $R_4$, $R_5$, and $R_{11}$ are H; $R_3$ is H, $OR_8$ or an optionally substituted alkyl group; $R_9$ is H, $OR_{12}$, or an alkyl, aryl or heteroaryl group each group optionally substituted; and $R_{10}$ is H, halogen, $OR_{13}$ or an optionally substituted alkyl group.

Preferred compounds of the invention include:

N-{4-[1-(6-Amino-pyridin-2-ylmethyl)-5-(2-chloro-phenyl)-1H-pyrrol-2-yl]-phenyl}-3-methyl-benzamide;

N-{4-[1-(6-Amino-pyridin-2-ylmethyl)-5-(2-chloro-phenyl)-1H-pyrrol-2-yl]-phenyl}-3-bromo-benzamide;

N-{4-[1-(6-Amino-pyridin-2-ylmethyl)-5-(2-chloro-phenyl)-1H-pyrrol-2-yl]-phenyl}-benzamide;

6-[2-(4-bromo-phenyl)-5-(2-chloro-phenyl)-pyrrol-1-ylmethyl]-pyridin-2-ylamine;

6-[2-(2-Chloro-phenyl)-5-(4-methoxy-phenyl)-pyrrol-1-ylmethyl]-pyridin-2-ylamine;

4-[1-(6-Amino-pyridin-2-ylmethyl)-5-(2-chloro-phenyl)-1H-pyrrol-2-yl]-phenol;

6-[2-(2-Chloro-phenyl)-5-(4-propoxy-phenyl)-pyrrol-1-ylmethyl]-pyridin-2-ylamine hydrochloride;

6-[2-(4-Butoxy-phenyl)-5-(2-chloro-phenyl)-pyrrol-1-ylmethyl]-pyridin-2-ylamine hydrochloride;

6-[2-(2-Chloro-phenyl)-5-(4-pentyloxy-phenyl)-pyrrol-1-ylmethyl]-pyridin-2-ylamine hydrochloride;

6-[2-(2-Chloro-phenyl)-5-(4-hexyloxy-phenyl)-pyrrol-1-ylmethyl]-pyridin-2-ylamine hydrochloride;

4-{4-[1-(6-Amino-pyridin-2-ylmethyl)-5-(2-chloro-phenyl)-1H-pyrrol-2-yl]-phenoxy}-butyronitrile hydrochloride;

5-{4-[1-(6-Amino-pyridin-2-ylmethyl)-5-(2-chloro-phenyl)-1H-pyrrol-2-yl]-phenoxy}-pentanenitrile hydrochloride;

6-{4-[1-(6-Amino-pyridin-2-ylmethyl)-5-(2-chloro-phenyl)-1H-pyrrol-2-yl]-phenoxy}-hexanenitrile hydrochloride;

6-{2-(2-Chloro-phenyl)-5-[4-(pyridin-4-yloxy)-phenyl]-pyrrol-1-ylmethyl}-pyridin-2-ylamine dihydrochloride;

6-{2-(2-Chloro-phenyl)-5-[2-(pyridin-4-yloxy)-phenyl]-pyrrol-1-ylmethyl}-pyridin-2-ylamine dihydrochloride;

6-[2-(2-Chloro-phenyl)-5-(4-phenoxy-phenyl)-pyrrol-1-ylmethyl]-pyridin-2-ylamine hydrochloride;

6-[2-Biphenyl-4-yl-5-(2-chloro-phenyl)-pyrrol-1-ylmethyl]-pyridin-2-ylamine;

6-{2-(2-Chloro-phenyl)-5-[4-(1,2-dihydro-pyridin-3-yl)-phenyl]-pyrrol-1-ylmethyl}-pyridin-2-ylamine;

6-[2-(2-Chloro-phenyl)-5-(4-pyrimidin-5-yl-phenyl)-pyrrol-1-ylmethyl]-pyridin-2-ylamine;

6-[2-(2-Chloro-phenyl)-5-(4-pyridin-3-yl-phenyl)-pyrrol-1-ylmethyl]-pyridin-2-ylamine;

6-{2-(2-Chloro-phenyl)-5-[4-(pyrimidin-2-yloxy)-phenyl]-pyrrol-1-ylmethyl}-pyridin-2-ylamine hydrochloride;

6-{2-(2-Chloro-phenyl)-5-[4-(thiazol-2-yloxy)-phenyl]-pyrrol-1-ylmethyl}-pyridin-2-ylamine hydrochloride;

6-{2-(2-Chloro-phenyl)-5-[4-(pyridazin-3-yloxy)-phenyl]-pyrrol-1-ylmethyl}-pyridin-2-ylamine hydrochloride;

6-{2-(2-Chloro-phenyl)-5-[4-(pyrazin-2-yloxy)-phenyl]-pyrrol-1-ylmethyl}-pyridin-2-ylamine hydrochloride;

6-{2-(2-Chloro-phenyl)-5-[4-(pyridin-3-yloxy)-phenyl]-pyrrol-1-ylmethyl}-pyridin-2-ylamine hydrochloride;

6-{2-(2-Chloro-phenyl)-5-[4-(pyrimidin-5-yloxy)-phenyl]-pyrrol-1-ylmethyl}-pyridin-2-ylamine hydrochloride;

1-(4-{4-[1-(6-Amino-pyridin-2-ylmethyl)-5-(2-chloro-phenyl)-1H-pyrrol-2-yl]-phenoxy}-phenyl)-ethanone hydrochloride;

6-[2-[4-(4-Bromo-phenoxy)-phenyl]-5-(2-chloro-phenyl)-pyrrol-1-ylmethyl]-pyridin-2-ylamine hydrochloride;

6-[2-(2-Chloro-phenyl)-5-(4-pentyloxy-phenyl)-pyrrol-1-ylmethyl]-pyridin-2-ylamine hydrochloride;

6-[2-(2-Chloro-phenyl)-5-(4-pentyloxy-phenyl)-pyrrol-1-ylmethyl]-3-methoxy-2-nitropyridine;

6-[2-(2-Chloro-phenyl)-5-(4-pentyloxy-phenyl)-pyrrol-1-ylmethyl]-3-methoxy-pyridin-2-ylamine hydrochloride;

3-{6-[2-(2-Chloro-phenyl)-5-(4-pentyloxy-phenyl)-pyrrol-1-ylmethyl]-3-methoxy-pyridin-2-ylamino}-propan-1-ol hydrochloride;

2-Amino-6-[2-(2-chloro-phenyl)-5-(4-pentyloxy-phenyl)-pyrrol-1-ylmethyl]-pyridin-3-ol hydrochloride;

6-[2-(2-Chloro-phenyl)-5-(4-pentyloxy-phenyl)-pyrrol-1-ylmethyl]-pyridine-2,3-diamine hydrochloride;

3-{2-Amino-6-[2-(2-chloro-phenyl)-5-(4-pentyloxy-phenyl)-pyrrol-1-ylmethyl]-pyridin-3-yloxy}-propan-1-ol hydrochloride;

4-{2-Amino-6-[2-(2-chloro-phenyl)-5-(4-pentyloxy-phenyl)-pyrrol-1-ylmethyl]-pyridin-3-yloxy}-butyronitrile hydrochloride;

2-{2-Amino-6-[2-(2-chloro-phenyl)-5-(4-pentyloxy-phenyl)-pyrrol-1-ylmethyl]-pyridin-3-ylamino}-ethanol hydrochloride;

3-{2-Amino-6-[2-(2-chloro-phenyl)-5-(4-pentyloxy-phenyl)-pyrrol-1-ylmethyl]-pyridin-3-ylamino}-propan-1-ol hydrochloride;

2-{2-Amino-6-[2-(2-chloro-phenyl)-5-(4-pentyloxy-phenyl)-pyrrol-1-ylmethyl]-pyridin-3-yloxy}-ethanol hydrochloride;

2-{2-Amino-6-[2-(2-chloro-phenyl)-5-(4-pentyloxy-phenyl)-pyrrol-1-ylmethyl]-pyridin-3-yloxy}-ethanol hydrochloride;

2-{2-Amino-6-[2-(4-bromo-phenyl)-5-(2-chloro-phenyl)-pyrrol-1-ylmethyl]-pyridin-3-yloxy}-ethanol;

{4-[1-(6-Amino-pyridin-2-ylmethyl)-5-(2-chloro-phenyl)-1H-pyrrol-2-yl]-phenyl}-pyrimidin-5-yl-amine;

2-(2-Amino-6-{2-(2-chloro-phenyl)-5-[4-(pyrimidin-5-yloxy)-phenyl]-pyrrol-1-ylmethyl}-pyridin-3-yloxy)-ethanol;

2-(2-Amino-6-{2-(2-chloro-phenyl)-5-[4-(pyrimidin-5-yloxy)-phenyl]-pyrrol-1-ylmethyl}-pyridin-3-ylamino)-ethanol;

Pentanoic acid {4-[1-(6-amino-pyridin-2-ylmethyl)-5-(2-chloro-phenyl)-1H-pyrrol-2-yl]-phenyl}-amide;

6-[2-(2-Chloro-phenyl)-5-(4-pentylamino-phenyl)-pyrrol-1-ylmethyl]-pyridin-2-ylamine hydrochloride;

2-[(2-amino-6-{[2-(2-chlorophenyl)-5-(4-propoxyphenyl)-1H-pyrrol-1-yl]methyl}pyridine-3-yl)oxy]ethanol;

6-[(2,5-diphenyl-1H-pyrrol-1-yl)methyl]pyridin-2-amine;

6-{[2-phenyl-5-(4-propoxyphenyl)-1H-pyrrol-1-yl]methyl}pyridin-2-amine;

Ethyl 4-[1-[(6-aminopyridin-2-yl)methyl]-5-(4-fluorophenyl)-1H-pyrrol-2-yl]benzoate;

Ethyl 4-{1-[(6-aminopyridin-2-yl)methyl]-5-phenyl-1H-pyrrol-2-yl}benzoate;

4-{1-[(6-aminopyridin-2-yl)methyl]-5-phenyl-1H-pyrrol-2-yl}-N-cyclopropylbenzamide;

4-{1-[(6-aminopyridin-2-yl)methyl]-5-phenyl-1H-pyrrol-2-yl}-N-ethylbenzamide;

4-[1-[(6-aminopyridin-2-yl)methyl]-5-(4-fluorophenyl)-1H-pyrrol-2-yl]-N-ethylbenzamide;

4-{1-[(6-aminopyridin-2-yl)methyl]-5-phenyl-1H-pyrrol-2-yl}-N-isopropylbenzamide;

4-{1-[(6-aminopyridin-2-yl)methyl]-5-phenyl-1H-pyrrol-2-yl}-N-butylbenzamide;

N-allyl-4-{1-[(6-aminopyridin-2-yl)methyl]-5-phenyl-1H-pyrrol-2-yl}benzamide;

4-{1-[(6-aminopyridin-2-yl)methyl]-5-phenyl-1H-pyrrol-2-yl}-N-propylbenzamide;

4-{1-[(6-aminopyridin-2-yl)methyl]-5-phenyl-1H-pyrrol-2-yl}-N-(tetrahydrofuran-2-ylmethyl)benzamide;

4-{1-[(6-aminopyridin-2-yl)methyl]-5-phenyl-1H-pyrrol-2-yl}-N-cyclobutylbenzamide;

or the stereoisomers or pharmaceutically acceptable salts thereof.

Compounds of the invention may be prepared employing conventional methods that utilize readily available reagents and starting materials. The reagents used in the preparation of the compounds of this invention can be either commercially obtained or can be prepared by standard procedures described in the literature. Representative compounds of the present invention can be prepared using the following synthetic schemes. The skilled practitioner will know how to make use of variants of these reaction sequences, which in themselves are well known in the art. For example, compounds of formula I wherein X is $CH_2$ (Ib) may be prepared as shown in Scheme 1 below.

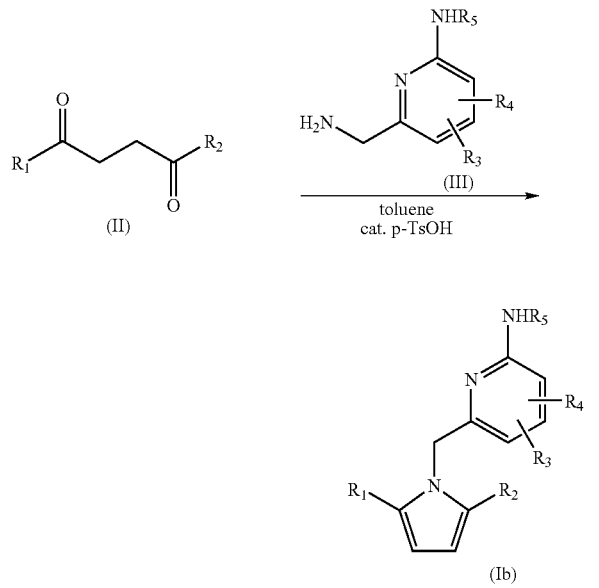

In scheme 1, the diketone II is reacted with the aminomethylpyridine III in the presence of a solvent such as toluene and a catalytic amount of an acid such a p-toluenesulfonic acid (p-TsOH) to give the desired compound of formula Ib.

Compounds of formula Ia wherein $R_9$ is other than H (Ic) may be prepared as shown in Scheme 2 below wherein Hal represents Cl or Br.

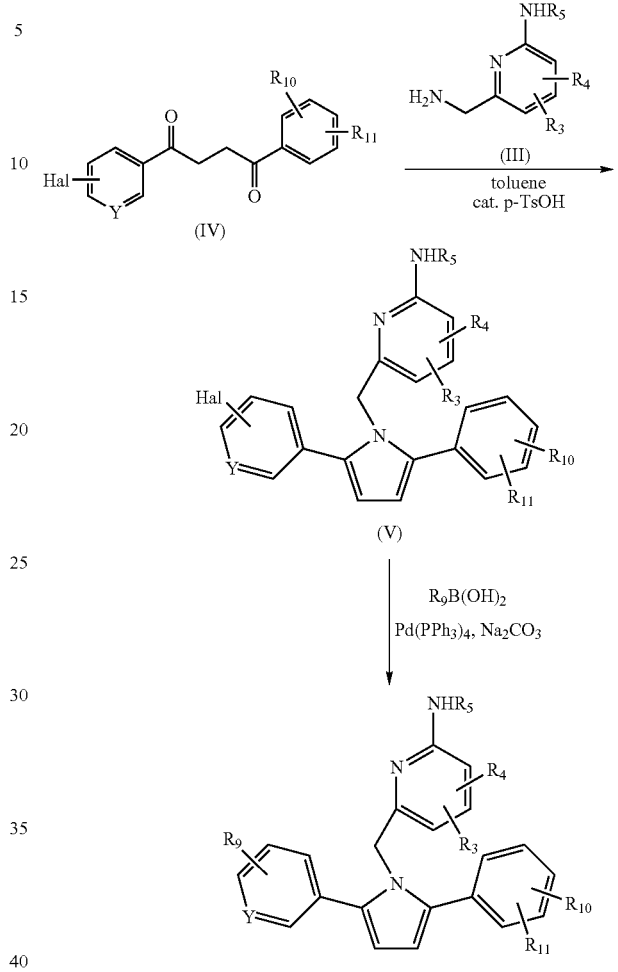

In scheme 2, the diketone IV is reacted with the aminomethylpyridine III as shown hereinabove in scheme 1 to give the compound V. Compound V is reacted with the appropriate boronic acid, $R_9B(OH)_2$, wherein $R_9$ is other than H, in the presence of $Pd(PPh_3)_4$ and a base such as $Na_2CO_3$ to give the desired compound of formula Ia wherein $R_9$ is other than H (Ic).

Similarly, compounds of formula I wherein X is NR (Id) may be prepared as shown in scheme 3 below.

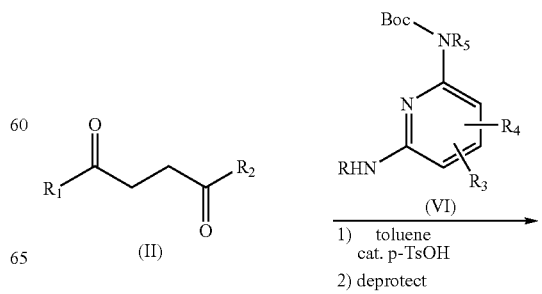

-continued

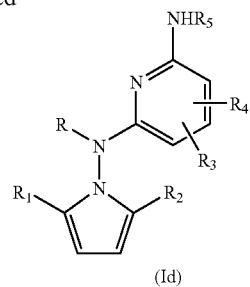

(Id)

In scheme 3, the diketone II is reacted with the protected 2,6-diaminopyridine VI in the presence of a solvent such as toluene and a catalytic amount of an acid such a p-toluenesulfonic acid (p-TsOH) and then deprotected to give the desired compound of formula Id.

Advantageously, the compounds of formula I act as BACE inhibitors for the treatment of β-amyloid deposits and neurofibrillary tangles associated with such diseases as Alzheimer's disease, Trisomy 21 (Down's Syndrome), Hereditary Cerebral Hemorrhage with Amyloidosis of the Dutch-type (HCHWA-D), and other neurodegenerative disorders. Accordingly, the present invention provides methods for modulating BACE and treating, preventing, or ameliorating β-amyloid deposits and neurofibrillary tangles associated with diseases and disorders such as Alzheimer's disease, Trisomy 21 (Down's Syndrome), Hereditary Cerebral Hemorrhage with Amyloidosis of the Dutch-type (HCHWA-D), and other neurodegenerative disorders. Such methods generally involve administering to a patient suspected of suffering from or being susceptible to the disease or injury an effective amount of a compound of formula I. Also according to the present invention there is provided a method of treating Alzheimer's disease and related senile dementia's in humans or other mammals which comprises administering to a human or other mammal an effective amount of a compound of the present invention.

The present invention also provides methods for treating a patient suspected of suffering from a disease associated with excessive BACE activity, comprising the step of administering to the patient an effective amount of at least one compound of Formula I. Representative diseases include Alzheimer's disease, cognitive impairment, Down's Syndrome, HCHWA-D, cognitive decline, senile dementia, cerebral amyloid angiopathy, degenerative dementia, or other neurodegenerative disorders. Certain of these diseases are characterized by production of β-amyloid deposits or neurofibrillary tangles.

The present invention also provides methods for modulating (and, preferably, inhibiting) the activity of BACE, comprising administering to a patient and/or contacting a receptor thereof with an effective amount of at least one compound of Formula I. Certain methods further comprise determining BACE activity, either before or after said contacting step.

The present invention also provides methods of ameliorating β-amyloid deposits in a mammal, comprising administering to said mammal an effective amount of at least one compound of Formula I. Further methods ameliorate neurofibrillary tangles in a mammal, and comprise administering to said mammal an effective amount of at least one compound of Formula I.

Also provided are methods of ameliorating symptoms of Alzheimer's disease, cognitive impairment, Down's Syndrome, HCHWA-D, cognitive decline, senile dementia, cerebral amyloid angiopathy, degenerative dementia, or other neurodegenerative disorders in a mammal, comprising administering to said mammal an effective amount of at least one compound of Formula I.

Further methods prevent Alzheimer's disease, cognitive impairment, Down's Syndrome, HCHWA-D, cognitive decline, senile dementia, cerebral amyloid angiopathy, degenerative dementia, or other neurodegenerative disorders in a mammal that is known to suffer from or suspected to be at risk of suffering from such diseases. These methods comprise administering to said mammal an amount of at least one compound of Formula I that is effective to prevent such disease.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The terms "effective amount", "therapeutically effective amount" and "effective dosage" as used herein, refer to the amount of a compound that, when administered to a patient, is effective to at least partially ameliorate (and, in preferred embodiments, cure) a condition form which the patient is suspected to suffer.

It is understood that the effective dosage of the active compounds of this invention may vary depending upon the particular compound utilized, the mode of administration, the condition, and severity thereof, of the condition being treated, as well as the various physical factors related to the individual being treated. For treating Alzheimer's disease and other related senile dementia's, generally, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg preferably from about 3.5 to about 5 mg. In the case of a 70 kg human adult, the total daily dose will generally be from about 7 mg to about 70 mg and may be adjusted to provide the optimal therapeutic result. This regimen may be adjusted to provide the optimal therapeutic response.

In one aspect, the present invention is directed to compositions comprising one or more compounds of formula I and one or more pharmaceutically acceptable carriers.

The present invention also comprises pharmaceutical compositions comprising compounds of the above-described Formula I and a pharmaceutically acceptable carrier.

The term "carrier", as used herein, shall encompass carriers, excipients, and diluents. Examples of carriers are well known to those skilled in the art and are prepared in accordance with acceptable pharmaceutical procedures, such as, for example, those described in Remington's Pharmaceutical Sciences, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulsifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, and may given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabronchial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975).

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The present compounds are further described in the following examples. The following abbreviations are used: DMSO is dimethylsulfoxide, DMF is N,N-dimethylformamide, HNMR is proton nuclear magnetic resonance, and MS is mass spectroscopy with (+) referring to the positive mode which generally gives a M+1 (or M+H) absorption where M=the molecular mass. All compounds are analyzed at least by MS and NMR.

Proton nuclear magnetic resonance spectra were obtained on a Bruker AVANCE 300 spectrometer at 300 MHz. Spectra are given in ppm (δ) and coupling constants, J values, are reported in Hertz. Tetramethylsilane was used as an internal reference standard. Infrared spectra were obtained on a Nicolet Nexus 470 (ATR) spectrometer. Mass spectra were obtained on a Perkin Elmer Sciex 100 atmospheric pressure ionization (APCI) mass spectrometer, or a Finnigan LCQ Duo LCMS ion trap electrospray ionization (ESI) mass spectrometer. Thin-layer chromatography (TLC) was performed using Analtech silica gel plates and visualized by ultraviolet (UV) light or iodine. HPLC analyses were obtained using a Waters Symmetry C18 column (4.6×250 mm) with UV detection at 254 nm using standard solvent gradient programs (Method 1 and Method 2). Preparative HPLC purifications were performed using a Phenomenex C18 column (21.2×150 mm) with UV detection at 254 nm using a standard solvent gradient program (Method 3). Elemental analyses were performed by Quantitative Technologies, Inc. (Whitehouse, N.J.).

Method 1

| Time (min) | Flow (mL/min) | % A | % B |
|---|---|---|---|
| 0.0 | 1.0 | 95.0 | 5.0 |
| 20.0 | 1.0 | 5.0 | 95.0 |
| 30.0 | 1.0 | 5.0 | 95.0 |

A = Water with 0.05% v/v Trifluoroacetic Acid
B = Acetonitrile with 0.05% v/v Trifluoroacetic Acid Method 2

| Time (min) | Flow (mL/min) | % A | % B |
|---|---|---|---|
| 0.0 | 1.0 | 90.0 | 10.0 |
| 20.0 | 1.0 | 10.0 | 90.0 |
| 30.0 | 1.0 | 10.0 | 90.0 |

A = Water with 0.05% v/v Trifluoroacetic Acid
B = Acetonitrile with 0.05% v/v Trifluoroacetic Acid Method 3

| Time (min) | Flow (mL/min) | % A | % B |
|---|---|---|---|
| 0.0 | 1.0 | 15.0 | 85.0 |
| 20.0 | 1.0 | 10.0 | 90.0 |

A = Water with 0.05% v/v Trifluoroacetic Acid
B = Acetonitrile with 0.05% v/v Trifluoroacetic Acid

EXAMPLE 1

Preparation of N-{4-[1-(6-Amino-pyridin-2-ylmethyl)-5-(2-chloro-phenyl)-1H-pyrrol-2-yl]-phenyl}-3-methyl-benzamide

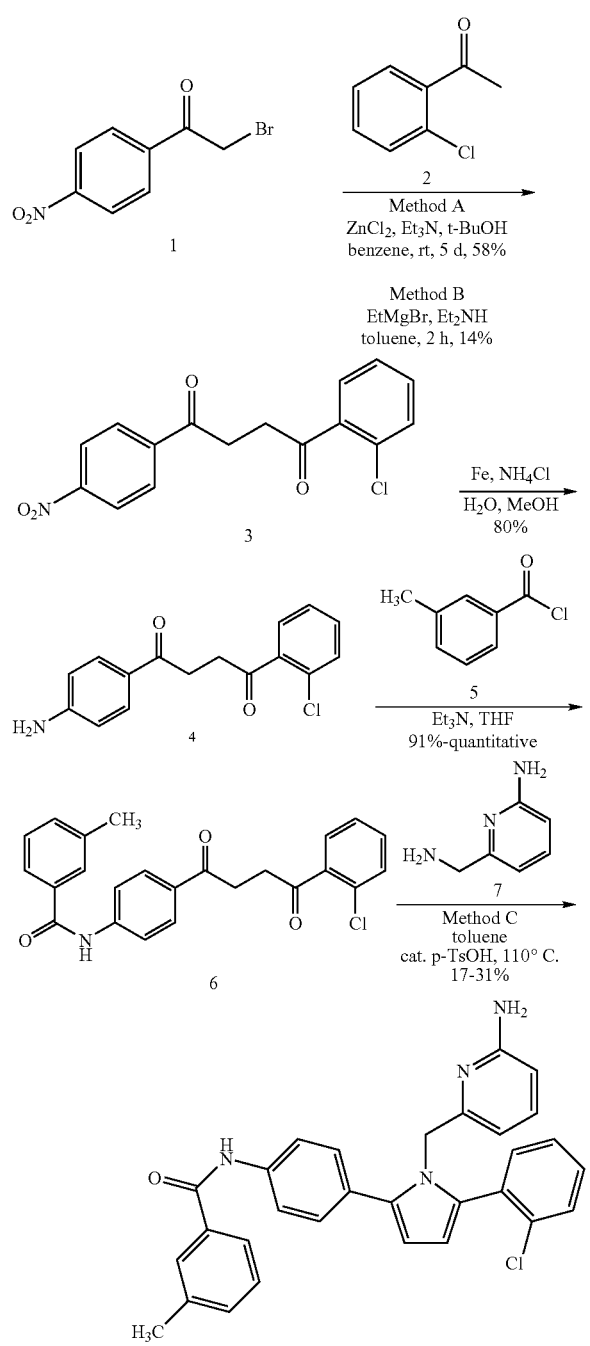

Step 1: Preparation of Intermediate 3

Method A: Zinc chloride (24.5 g, 180 mmol) was dried under vacuum at 200° C. for 15 min. After cooling to room temperature, benzene (90 mL), triethylamine (13.7 g, 135 mmol), then t-butanol (10.0 g, 135 mmol) were added and the mixture stirred at room temperature. After 3 h, compound 1 (21.9 g, 90.0 mmol) and compound 2 (20.9 g, 135 mmol) were added and stirring continued for 5 d. The reaction was then quenched with 5% aqueous $H_2SO_4$ (200 mL) and diluted with ethyl acetate (1500 mL) and water (150 mL). The organic layer was separated and washed with brine (500 mL), dried over magnesium sulfate, filtered and concentrated to afford 34.6 g of a light yellow solid. Recrystallization from ethyl acetate afforded intermediate 3 (16.5 g, 58%) as a yellow-brown solid: $^1$H NMR (300 MHz, $CDCl_3$) δ 8.34 (d, J=9.0 Hz, 2H), 8.18 (d, J=9.0 Hz, 2H), 7.64 (m, 1H), 7.45-7.36 (m, 3H), 3.51-3.43 (m, 4H).

Method B: A mixture of ethylmagnesium bromide (8.00 mL of a 3.0 M solution in diethyl ether, 24.0 mmol) and diethylamine (1.75 g, 24.0 mmol) in toluene (60 mL) was stirred at room temperature. After 15 min the mixture was cooled with an ice bath and treated with a mixture of compound 1 (4.88 g, 20.0 mmol) and compound 2 (3.71 g, 24.0 mmol) in toluene (30 mL). The mixture was stirred at ice bath temperature for 1 h then the cooling bath removed and the mixture was allowed to stir at room temperature for 1 h. HCl (1 N, 40 mL) was then added, the organic layer separated and treated with triethylamine (2.03 g, 20.0 mmol). The mixture was allowed to stand at room temperature overnight, then washed with water (20 mL), 1 N HCl (20 mL), brine (20 mL), dried over magnesium sulfate, filtered and concentrated to afford 5.38 g of a dark red syrup. Purification by flash chromatography (silica, 1:5 ethyl acetate/hexanes) afforded intermediate 3 (0.90 g, 14%) as a tan solid. This material was identical to that prepared using method A by $^1$H NMR analysis.

Step 2: Preparation of Intermediate 4

A mixture of compound 3 (1.50 g, 4.72 mmol), iron powder (1.32 g, 23.6 mmol) and ammonium chloride (1.89 g, 35.4 mmol) in 1:1 water/ethanol (90 mL) was heated at reflux for 2 h. The mixture was cooled to room temperature, and additional iron powder (0.40 g, 7.2 mmol) and ammonium chloride (0.39 g, 7.20 mmol) were added and reflux continued for an additional 1.5 h. After standing overnight at room temperature, ethyl acetate (45 mL) and sodium carbonate (4 g) were added. The mixture was stirred at room temperature for 30 min then filtered through diatomaceous earth and the solids washed with ethyl acetate (100 mL). The organic layer was separated, washed with brine (100 mL), dried over magnesium sulfate, filtered and concentrated to afford intermediate 4 (1.08 g, 80%) as a yellow solid: $^1$H NMR (300 MHz, $CDCl_3$) δ 7.87 (d, J=8.7 Hz, 2H), 7.64 (d, J=2.3 Hz, 1H), 7.41-7.30 (m, 3H), 6.66 (d, J=8.7 Hz, 2H), 4.12 (br s, 2H), 3.40-3.33 (m, 4H); ESI MS m/z 388 $[C_{16}H_{14}ClNO_2+H]^+$.

Step 3: Preparation of Intermediate 6

To a stirred, ice-cold mixture of 4 (0.30 g, 1.04 mmol) and triethylamine (0.11 g, 1.04 mmol) in THF (6 mL) was added m-toluoyl chloride (0.16 g, 1.04 mmol). After stirring for 1.5 h at ice-bath temperature and an additional 1 h at room temperature, the reaction mixture was diluted with ethyl acetate (100 mL), washed with water (50 mL), 1 N HCl (50 mL), brine (50 mL), dried over magnesium sulfate and concentrated to afford intermediate 6 as a light yellow-brown solid: $^1$H NMR (300 MHz, $CDCl_3$) δ 8.05 (d, J=8.7 Hz, 2H), 7.97 (s, 1H), 7.79 (d, J=8.7 Hz, 2H), 7.70-7.64 (m, 3H), 7.43-7.36 (m, 5H), 3.50-3.46 (m, 2H), 3.40-3.36 (m, 2H), 2.45 (s, 3H).

Step 4: Preparation of N-{4-[1-(6-Amino-pyridin-2-ylmethyl)-5-(2-chlorophenyl)-1H-pyrrol-2-yl]-phenyl}-3-methyl-benzamide A mixture of 6 (0.20 g, 0.49 mmol), 6-aminomethyl-pyridin-2-ylamine (0.06 g, 0.49, mmol) and p-toluenesulfonic acid monohydrate (0.005 g, 0.024 mmol) in toluene (12 mL) was heated at 110° C. for 22 h. The mixture was cooled and concentrated to afford 0.26 g of a yellow solid. Purification by flash chromatography (silica, 1:1 ethyl acetate/hexanes) afforded 8a (0.075 g, 31%) as a white solid: $R_f$ 0.31 (1:1 ethyl acetate/hexanes); mp 108-118° C.; $^1$H NMR (300 MHz, CDCl$_3$) δ 7.77 (s, 1H), 7.69 (s, 1H), 7.62-7.59 (m, 3H), 7.42-7.35 (m, 5H), 7.25-7.18 (m, 4H), 6.40 (d, J=3.5 Hz, 1H), 6.33 (d, J=3.5 Hz, 1H), 6.21 (d, J=8.1 Hz, 1H), 5.76 (d, J=7.4 Hz, 1H), 5.02 (s, 2H), 4.20 (s, 2H), 2.44 (s, 3H); IR (ATR) 1655, 1610, 1585, 1514, 1484 cm$^{-1}$; ESI MS m/z 493 [C$_{30}$H$_{25}$ClN$_4$O+H]$^+$; HPLC (Method 1)>99% (AUC), $t_R$=13.74 min. Anal. Calcd for C$_{30}$H$_{25}$ClN$_4$O.0.5H$_2$O: C, 71.78; H, 5.22; N, 11.16. Found: C, 71.47; H, 5.06; N, 10.93.

EXAMPLE 2

Preparation of N-{4-[1-(6-Amino-pyridin-2-ylmethyl)-5-(2-chloro-phenyl)-1H-pyrrol-2-yl]-phenyl}-3-bromo-benzamide

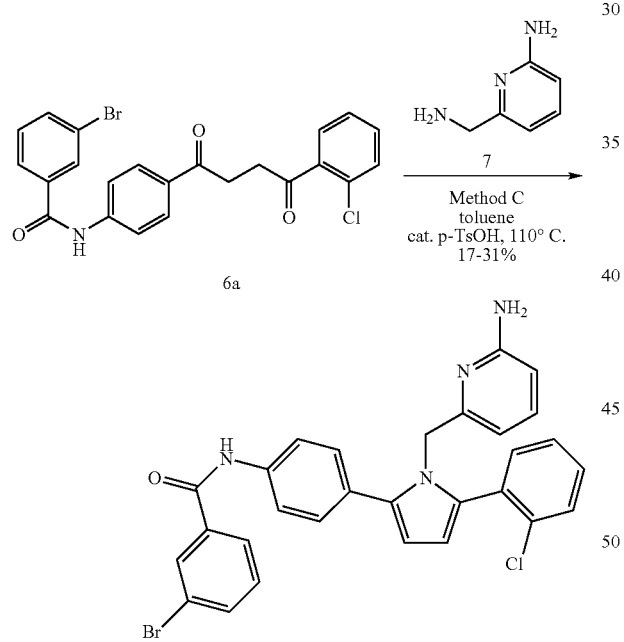

The reaction of 6a with 7 was performed essentially as described in Example 1, step 4. Purification by flash chromatography (silica, 2:3 ethyl acetate/hexanes) afforded the title compound (53.0 mg, 17%) as an off-white solid: $R_f$ 0.44 (1:4 ethyl acetate/hexanes); mp 116-122° C.; $^1$H NMR (300 MHz, CDCl$_3$) δ 8.00 (s, 1H), 7.80-7.50 (m, 5H), 7.45-7.30 (m, 4H), 7.30-7.20 (m, 4H), 6.41 (d, J=3.5 Hz, 1H), 6.33 (d, J=3.5 Hz, 1H). 6.21 (d, J=8.1 Hz, 1H), 5.76 (d, J=7.1 Hz, 1H), 5.01 (s, 2H), 4.36 (s, 2H); IR (ATR) 1522, 1461, 1316 cm$^{-1}$; ESI MS m/z 559 [C$_{29}$H$_{22}$BrClN$_4$O+H]$^+$; HPLC (Method 1)>99% (AUC), $t_R$=14.31 min. Anal. Calcd for C$_{29}$H$_{22}$BrClN$_4$O: C, 62.44; H, 3.97; N, 10.04. Found: C, 62.05; H, 4.04; N, 9.51.

EXAMPLE 3

Preparation of N-{4-[1-(6-Amino-pyridin-2-ylmethyl)-5-(2-chloro-phenyl)-1H-pyrrol-2-yl]-phenyl}-benzamide The reaction of 6b with 7 was performed essentially as described in Example 1, step 4. Purification by flash chromatography (silica, 1:1 ethyl acetate/hexanes) afforded the title compound (121 mg, 31%) as a pale yellow solid: $R_f$ 0.31 (1:1 ethyl acetate/hexanes); mp 196-198° C.; $^1$H NMR (300 MHz, CDCl$_3$) δ 7.86 (d, J=6.6 Hz, 2H), 7.80 (s, 1H), 7.62-7.21 (m, 12H), 6.41 (d, J=3.5 Hz, 1H), 6.33 (d, J=3.6 Hz, 1H), 6.21 (d, J=8.2 Hz, 1H), 5.76 (d, J=7.2 Hz, 1H), 5.01 (s, 2H), 4.21 (s, 2H); IR (ATR) 1576, 1517, 1462 cm$^{-1}$; ESI MS m/z 479 [C$_{29}$H$_{23}$ClN$_4$O+H]$^+$; HPLC (Method 1) 98.8% (AUC), $t_R$=13.39 min.

EXAMPLE 4

Preparation of 6-[2-(4-bromo-phenyl)-5-(2-chloro-phenyl)-pyrrol-1-ylmethyl]-pyridin-2-ylamine -continued

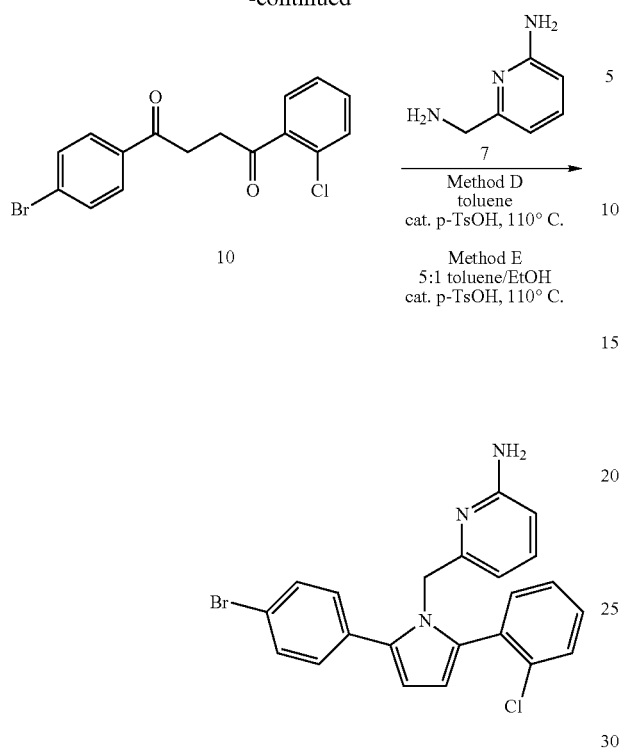

Step 1: Preparation of intermediate 10

Method A: The reaction of 2 with 9 was performed essentially as described in Example 1, step 1, method A. Purification by trituration with ether afforded 10 (4.50 g, 71%) as a white solid: $^1$H NMR (300 MHz, CDCl$_3$) δ 7.89 (d, J=8.6 Hz, 2H), 7.64-7.61 (m, 3H), 7.43-7.38 (m, 3H), 3.44-3.85 (m, 4H).

Method B: The reaction of 2 with 9 was performed essentially as described in Example 1, step 1, method B. Purification by flash chromatography (silica, 1:10 ethyl acetate/hexanes) afforded 10 (1.02 g, 40%) as an off-white solid. This material was identical to that prepared using method A by $^1$H NMR analysis.

Step 2: Preparation of 6-[2-(4-bromo-phenyl)-5-(2-chloro-phenyl)-pyrrol-1-ylmethyl]-pyridin-2-ylamine The reaction of 10 with 7 was performed essentially as described in Example 1, step 4. Purification by flash chromatography (silica, 1:4 ethyl acetate/hexanes then 1:3 ethyl acetate/hexanes) afforded the title compound (81.0 mg, 23%) as a pale yellow solid: R$_f$ 0.23 (1:4 ethyl acetate/hexanes); mp 154-158° C.; $^1$H NMR (300 MHz, CDCl$_3$) δ 7.46-7.39 (m, 3H), 7.28-7.15 (m, 6H), 6.39 (d, J=3.6 Hz, 1H), 6.31 (d, J=3.6 Hz, 1H), 6.21 (d, J=8.1 Hz, 1H), 5.72 (d, J=7.4 Hz, 1H), 4.97 (s, 2H), 4.21 (br s, 2H); IR (ATR) 1638, 1603, 1574 cm$^{-1}$; ESI MS m/z 440 [C$_{22}$H$_{17}$BrClN$_3$+H]$^+$; HPLC (Method 1) 96.3% (AUC), t$_R$=14.02 min. Anal. Calcd for C$_{22}$H$_{17}$BrClN$_3$·0.5H$_2$O: C, 59.01; H, 4.05; N, 9.38. Found: C, 59.31; H, 3.67; N, 9.06.

EXAMPLE 5

Preparation of 6-[2-(2-Chloro-phenyl)-5-(4-methoxy-phenyl)-pyrrol-1-ylmethyl]-pyridin-2-ylamine

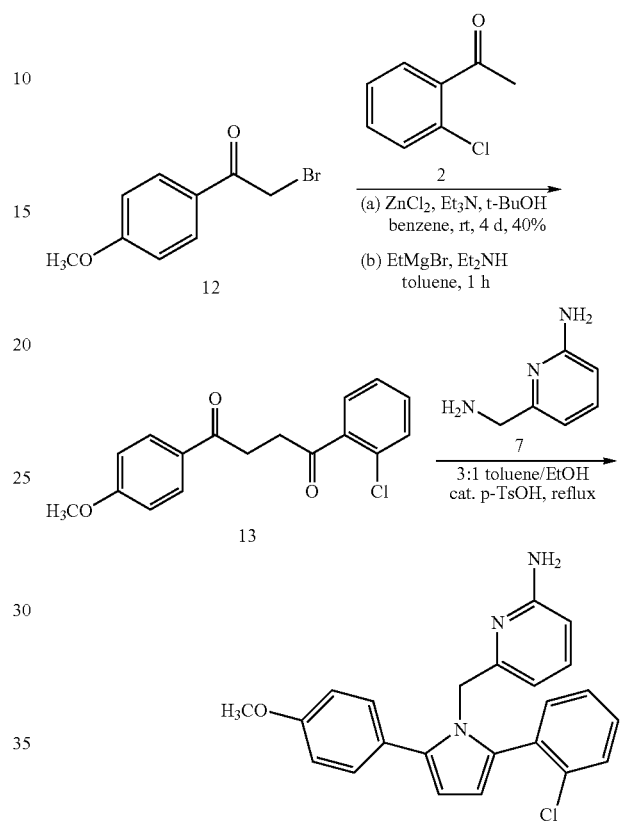

Step 1: Preparation of Intermediate 13

(a) Zinc chloride (5.72 g, 42.0 mmol) was dried under vacuum at 250° C. for 30 min. After cooling to room temperature, triethylamine (3.22 g, 32.0 mmol), toluene (50 mL), then t-butanol (2.37 g, 32.0 mmol) was added and the mixture was stirred at 60° C. for 1.5 h to dissolve most of the solid. The reaction was then cooled to room temperature and 2'-chloroacetophenone (5.00 g, 32.0 mmol) and 4-methoxyphenacyl bromide (4.94 g, 21.0 mmol) were added. The reaction was stirred for 4 d at room temperature, quenched with 6 N HCl (150 mL) and diluted with ethyl acetate (300 mL). The organic layer was separated and washed with saturated sodium bicarbonate (100 mL) and brine (100 mL), dried over sodium sulfate, filtered and concentrated. Purification by flash chromatography (silica, 1:9 ethyl acetate/hexanes) afforded the title compound (2.55 g, 40%) as a colorless syrup: $^1$H NMR (300 MHz, CDCl$_3$) δ 8.00 (d, J=9.0 Hz, 2H), 7.64 (m, 1H), 7.30-7.50 (m, 3H), 6.94 (d, J=9.0 Hz, 2H), 3.88 (s, 3H), 3.43 (t, J=6.0 Hz, 2H), 3.37 (t, J=6.0 Hz, 2H).

(b) A mixture of ethylmagnesium bromide (6.46 mL of a 3.0 M solution in diethyl ether, 19.4 mmol) and diethylamine (1.42 g, 19.4 mmol) in toluene (25 mL) was stirred at room temperature. After 15 min the mixture was cooled with an ice bath and treated with a solution of 2'-chloroacetophenone (3.00 g, 19.4 mmol) and 4-methoxyphenacyl bromide (3.71 g, 16.2 mmol) in toluene (5 mL). The cooling bath was removed and the reaction was allowed to warm and stir at room temperature for 1 h. The reaction was diluted with 6 N HCl (150 mL) and ethyl acetate (300 mL). The organic layer was separated and washed with saturated sodium bicarbonate (100 mL) and brine (100 mL), dried over sodium sulfate, filtered and concentrated. Purification by flash chromatography (silica, 1:9 ethyl acetate/hexanes) afforded 13 (2.64 g, 54%) as a colorless oil: $^1$H NMR (300 MHz, CDCl$_3$) δ 8.00 (d, J=9.0 Hz, 2H), 7.64 (m, 1H), 7.30-7.50 (m, 3H), 6.94 (d, J=9.0 Hz, 2H), 3.88 (s, 3H), 3.43 (t, J=6.0 Hz, 2H), 3.37 (t, J=6.0 Hz, 2H); ESI MS m/z 303 [C$_{17}$H$_{15}$ClO$_3$+H]$^+$.

Step 2: Preparation of 6-[2-(2-Chloro-phenyl)-5-(4-methoxy-phenyl)-pyrrol-1-ylmethyl]-pyridin-2-ylamine A mixture of 7 (0.90 g, 7.30 mmol), 13 (1.11 g, 3.65 mmol) and p-toluenesulfonic acid (0.18 g, 0.95 mmol) in 3:1 toluene/ethanol (120 mL) was heated at reflux overnight. The reaction was cooled, concentrated and diluted with methylene chloride (500 mL) and water (100 mL). The organic layer was separated, washed with brine (200 mL), dried over sodium sulfate, filtered and concentrated. Purification by flash chromatography (silica, 99.5:0.5 methylene chloride/methanol) afforded the title compound (0.66 g, 46%) as a pink solid: R$_f$ 0.60 (50:50 hexanes/ethyl acetate); mp 147-148° C.; $^1$H NMR (300 MHz, CDCl$_3$) δ 7.20-7.50 (m, 7H), 6.85 (d, J=8.7 Hz, 2H), 6.33 (d, J=3.6 Hz, 1H), 6.29 (d, J=3.6 Hz, 1H), 6.20 (d, J=7.8 Hz, 1H), 5.75 (d, J=7.8 Hz, 1H), 4.97 (s, 2H), 4.23 (s, 2H), 3.80 (s, 3H); IR (ATR) 3476, 3146, 2935, 1609, 1574, 1485, 1460, 1288, 1245, 883, 758 cm$^{-1}$; ESI MS m/z 390 [C$_{23}$H$_{20}$ClN$_3$O+H]$^+$; HPLC (Method 1) 97.8% (AUC), t$_R$=13.13 min. Anal. Calcd for C$_{23}$H$_{20}$ClN$_3$O: C, 70.85; H, 5.17; N, 10.78. Found: C, 70.17; H, 5.26; N, 10.78.

EXAMPLE 6

Preparation of 4-[1-(6-Amino-pyridin-2-ylmethyl)-5-(2-chloro-phenyl)-1H-pyrrol-2-yl]-phenol

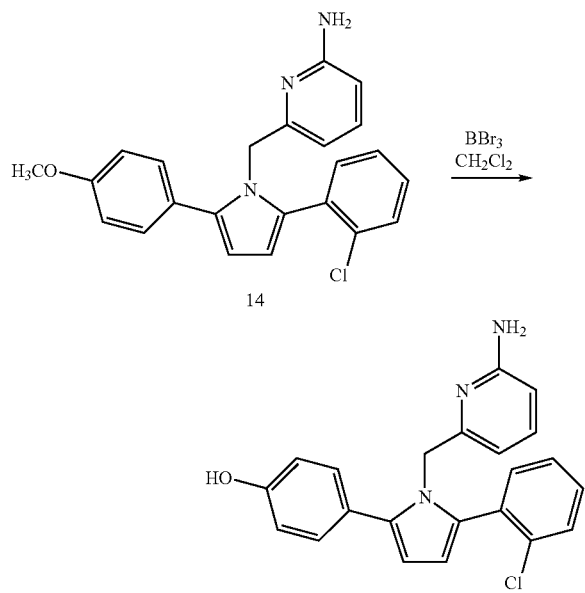

A solution of 14 (0.50 g, 1.28 mmol) in methylene chloride (16 mL) was cooled to −78° C. and treated dropwise with boron tribromide (6.42 mL of a 1.0 M solution in methylene chloride, 6.42 mmol). The reaction mixture was stirred overnight warming to room temperature, quenched with ice water and diluted with ethyl acetate (300 mL). The organic layer was separated, washed with brine (150 mL), dried over sodium sulfate, filtered and concentrated. Purification by flash chromatography (silica, 97.5:2.5 methylene chloride/methanol) afforded the title compound (0.40 g, 83%) as an off-white solid: R$_f$ 0.25 (50:50 hexanes/ethyl acetate); mp 170-172° C.; $^1$H NMR (300 MHz, CDCl$_3$) δ 7.20-7.50 (m, 7H), 6.68 (d, J=8.6 Hz, 2H), 6.32 (s, 2H), 6.23 (d, J=7.8 Hz, 1H), 5.75 (d, J=7.8 Hz, 1H), 5.03 (s, 2H), 4.22 (s, 2H); IR (ATR) 3485, 3375, 3058, 2565, 1619, 1576, 1468, 1266, 1235, 835, 752, 732 cm$^{-1}$; ESI MS m/z 376 [C$_{22}$H$_{18}$ClN$_3$O+H]$^+$; HPLC (Method 1) 97.5% (AUC), t$_R$=12.19 min. Anal. Calcd for C$_{22}$H$_{18}$ClN$_3$O: C, 70.30; H, 4.83; N, 11.18. Found: C, 69.45; H, 4.66; N, 10.45.

EXAMPLE 7

Preparation of 6-[2-(2-Chloro-phenyl)-5-(4-propoxy-phenyl)-pyrrol-1-ylmethyl]-pyridin-2-ylamine

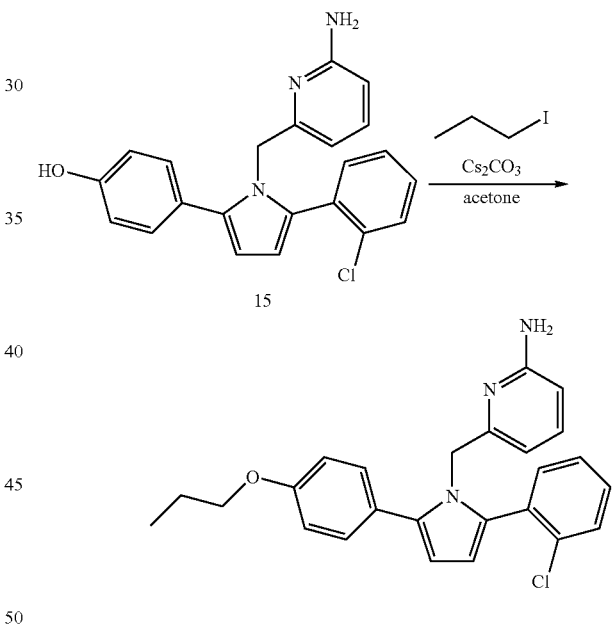

A mixture of 15 (0.12 g, 0.320 mmol) and cesium carbonate (1.04 g, 3.20 mmol) in acetone (25 mL) was heated at reflux for 10 min, treated with 1-iodopropane (0.064 g, 0.38 mmol) and heating was continued for an additional 30 min. The mixture was then cooled to room temperature, concentrated and diluted with methylene chloride (150 mL) and water (50 mL). The organic layer was separated, washed with brine (100 mL), dried over sodium sulfate, filtered and concentrated. Purification by flash chromatography (silica, 99.5:0.5 methylene chloride/methanol) afforded the title compound (0.14 g, quantitative) as a colorless syrup: $^1$H NMR (300 MHz, CDCl$_3$) δ 7.20-7.50 (m, 7H), 6.85 (d, J=8.7 Hz, 2H), 6.32 (d, J=3.6 Hz, 1H), 6.29 (d, J=3.6 Hz, 1H), 6.20 (d, J=8.4 Hz, 1H), 5.73 (d, J=8.4 Hz, 1H), 4.97 (s, 2H), 4.23 (s, 2H), 3.90 (t, J=6.6 Hz, 2H), 1.76 (tq, J=7.3, 6.6 Hz, 2H), 0.95 (t, J=7.3 Hz, 3H).

EXAMPLES 8-13

Preparation of 6-[2-(2-Chloro-phenyl)-5-(4-alkoxyphenyl)-pyrrol-1-ylmethyl]-pyridin-2-ylamine Derivatives

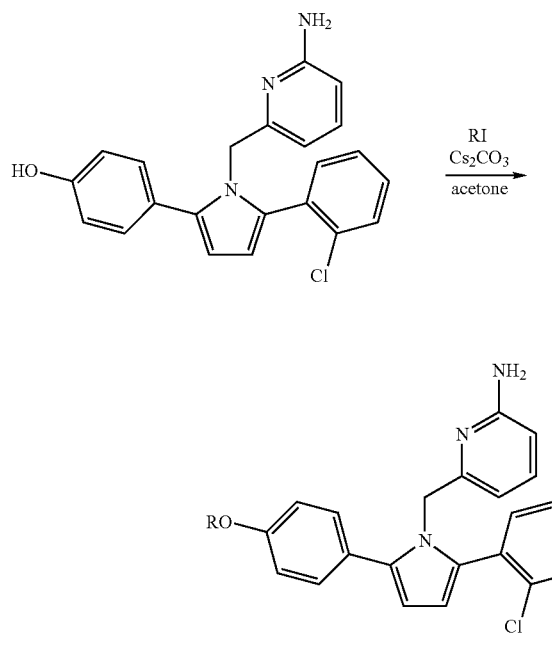

Using essentially the same procedure described in Example 7 hereinabove and employing the appropriate akyliodide, the compounds shown in Table I are obtained and identified by HNMR and mass spectral analyses.

TABLE I

| Ex. No. | R | % Yield | Ms m/z |
|---|---|---|---|
| 8 | n-butyl | 36 | 432 |
| 9 | n-pentyl | 56 | 446 |
| 10 | n-hexyl | 65 | 460 |
| 11 | $(CH_2)_3CN$ | 51 | 443 |
| 12 | $(CH_2)_4CN$ | 73 | 457 |
| 13 | $(CH_2)_5CN$ | 31 | 471 |

EXAMPLE 14

Preparation of 6-[2-(2-Chloro-phenyl)-5-(4-propoxyphenyl)-pyrrol-1-ylmethyl]-pyridin-2-ylamine hydrochloride

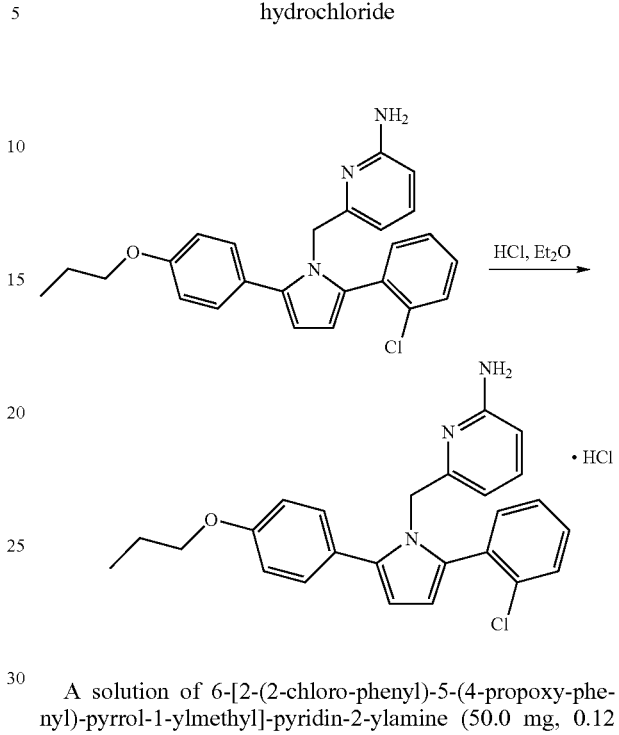

A solution of 6-[2-(2-chloro-phenyl)-5-(4-propoxy-phenyl)-pyrrol-1-ylmethyl]-pyridin-2-ylamine (50.0 mg, 0.12 mmol) and HCl (0.06 mL of a 2.0 M solution in diethyl ether, 0.12 mmol) in diethyl ether (10 mL) was stirred at room temperature for 30 min. The mixture was concentrated and the solid obtained triturated with hexanes to afford the title compound (48.0 mg g, 88%) as an off-white solid: $R_f$ 0.65 (50:50 hexanes/ethyl acetate); mp 68-76° C.; $^1$H NMR (300 MHz, $CDCl_3$) δ 7.20-7.60 (m, 7H), 6.89 (d, J=8.7 Hz, 2H), 6.65 (br s, 1H), 6.45 (d, J=8.2 Hz, 1H), 6.39 (d, J=3.6 Hz, 1H), 6.35 (d, J=3.6 Hz, 1H), 5.75 (d, J=8.2 Hz, 1H), 5.24 (s, 2H), 3.93 (t, J=6.6 Hz, 2H), 1.80 (tq, J=7.5, 6.6 Hz, 2H), 1.04 (t, J=7.5 Hz, 3H); IR (ATR) 3292, 3105, 2964, 2711, 1661, 1628, 1486, 1244, 1174, 833, 755, 722 cm$^{-1}$; ESI MS m/z 418 $[C_{25}H_{24}ClN_3O+H]+$; HPLC (Method 1) 97.1% (AUC), $t_R$=14.53 min. Anal. Calcd for $C_{25}H_{24}ClN_3O \cdot HCl \cdot 0.5H_2O$: C, 64.80; H, 5.66; N, 9.07. Found: C, 64.63; H, 5.50; N, 8.65.

EXAMPLES 15-20

Preparation of 6-[2-(4-Alkoxyphenyl)-5-(2-chlorophenyl)pyrrol-1-ylmethyl]pyridin-2-ylamine hydrochloride Salts

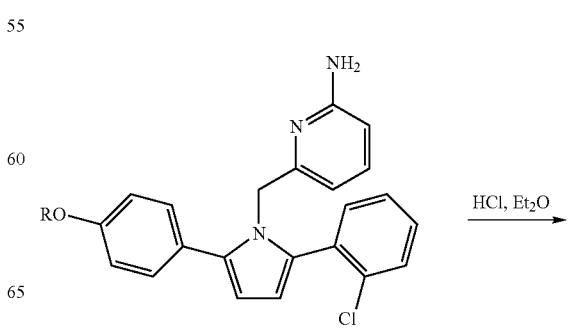

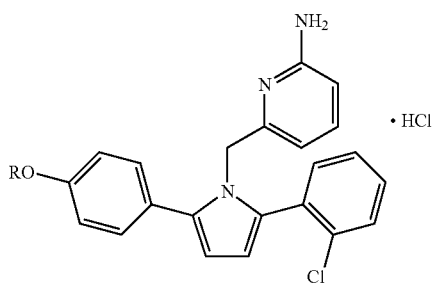

Using essentially the same procedure described in Example 14 and employing the appropriate substrate, the hydrochloride salts shown in Table II were obtained and identified by HNMR and mass spectral analyses.

TABLE II

| Ex. No. | R | % Yield | mp °C. | Ms m/z |
|---|---|---|---|---|
| 15 | n-butyl | 89 | 116-126 | 432 |
| 16 | n-pentyl | 92 | 88-98 | 446 |
| 17 | n-hexyl | 88 | 90-91 | 460 |
| 18 | (CH$_2$)$_3$CN | 92 | 112-122 | 443 |
| 19 | (CH$_2$)$_4$CN | 82 | 126-130 | 457 |
| 20 | (CH$_2$)$_5$CN | 93 | 98-106 | 471 |

EXAMPLE 21

Preparation of 6-[(2-(2-Chlorophenyl)-5-[4-(pyridin-4-yloxy)phenyl]pyrrol-1-ylmethyl]-pyridin-2-ylamine

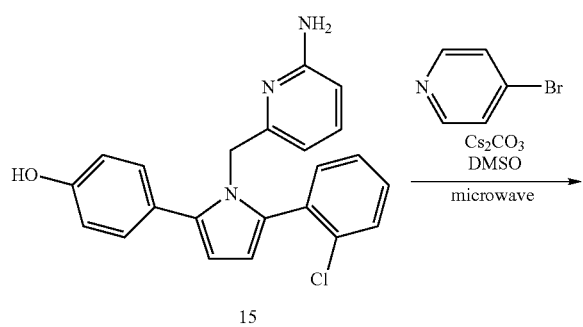

A mixture of 15 (0.05 g, 0.13 mmol), cesium carbonate (0.16 g, 0.47 mmol) and 4-bromopyridine hydrochloride (0.039 g, 0.20 mmol) in dimethyl sulfoxide (2 mL) was subjected to microwave irradiation at 160° C. and 150 W for 20 min. The reaction was cooled to room temperature and diluted with ethyl acetate (200 mL) and water (100 mL). The organic layer was separated, washed with brine (100 mL), dried over sodium sulfate, filtered and concentrated. Purification by preparative HPLC (Method 3) afforded the title product (0.041 g, 68%) as a colorless syrup: ESI MS m/z 453 [C$_{27}$H$_{21}$ClN$_4$O+H]$^+$.

EXAMPLE 22

Preparation of 6-[(2-(2-Chlorophenyl)-5-[4-(pyridin-2-yloxy)phenyl]pyrrol-1-ylmethyl]-pyridin-2-ylamine

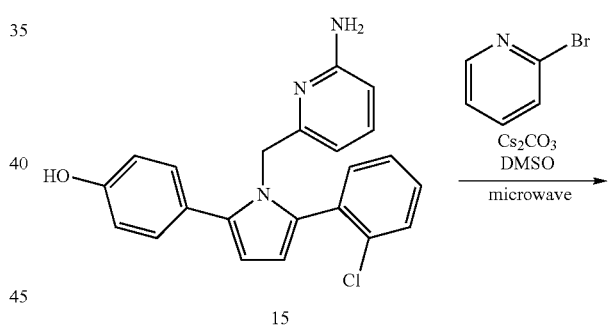

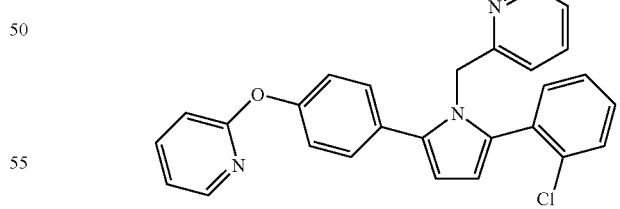

Using essentially the same procedure described in Example 21 and employing 2-bromopyridine, the title product was obtained. Purification by preparative HPLC (Method 3) (27.0 mg, 22%) afforded the title product as a colorless syrup: $^1$H NMR (300 MHz, CD$_3$OD) δ 8.20 (d, J=8.4 Hz, 1H), 7.70 (t, J=8.4 Hz, 1H), 7.00-7.50 (m, 10H), 6.90 (d, J=8.4 Hz, 1H), 6.39 (d, J=3.6 Hz, 1H), 6.30 (d, J=3.6 Hz, 1H), 6.25 (d, J=8.1 Hz, 1H), 5.76 (d, J=8.1 Hz, 1H), 5.02 (s, 2H), 4.23 (s, 2H); ESI MS m/z 453 [C$_{27}$H$_{21}$ClN$_4$O+H]$^+$.

EXAMPLE 23

Preparation of 6-{2-(2-Chlorophenyl)-5-[4-(Pyridin-4-yloxy)phenyl]pyrrol-1-ylmethyl}-pyridin-2-ylamine dihydrochloride

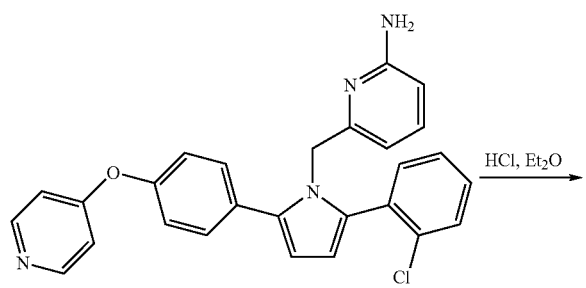

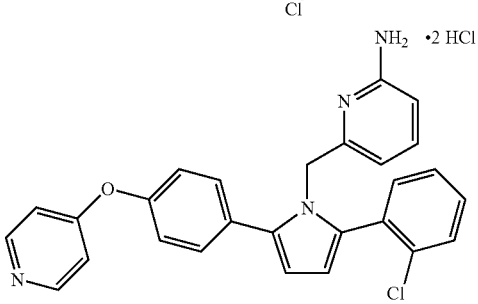

Using essentially the same procedure described in Example 14 and employing 6-{2-(2-chlorophenyl)-5-[4-(pyridin-4-yloxy)phenyl]pyrrol-1-ylmethyl}-pyridin-2-ylamine, afforded the title compound (61.0 mg, 86%) as an off-white solid: mp 180-185° C.; $^1$H NMR (300 MHz, CD$_3$OD) δ 8.69 (d, J=7.2 Hz, 2H), 7.20-7.70 (m, 11H), 6.70 (d, J=8.1 Hz, 1H), 6.50 (d, J=3.6 Hz, 1H), 6.39 (d, J=3.6 Hz, 1H), 5.89 (d, J=8.1 Hz, 1H), 5.22 (s, 2H); IR (ATR) 3483, 3432, 3144, 2644, 1661, 1630, 1479, 1285, 1193, 1168, 830, 780, 755 cm$^{-1}$; ESI MS m/z 453 [C$_{27}$H$_{21}$ClN$_4$O+H]$^+$; HPLC (Method 1)>99% (AUC), t$_R$=10.79 min. Anal. Calcd for C$_{27}$H$_{21}$ClN$_4$O.2HCl.1.5H$_2$O: C, 58.65; H, 4.74; N, 10.13. Found: C, 58.80; H, 4.50; N, 10.08.

EXAMPLE 24

Preparation of 6-[(2-(2-Chlorophenyl)-5-[2-(pyridin-2-yloxy)phenyl]pyrrol-1-ylmethyl]-pyridin-2-ylamine dihydrochloride

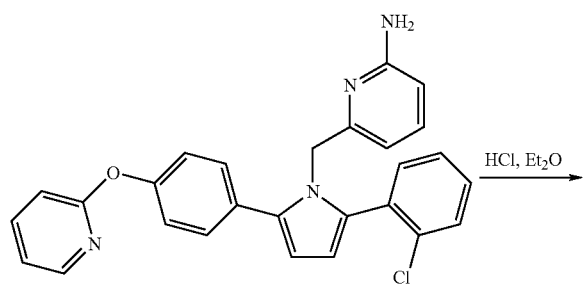

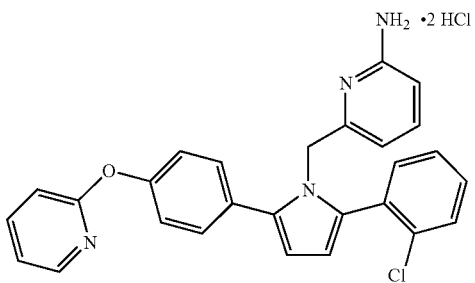

Using essentially the same procedure described in Example 14 and employing 6-{2-(2-chlorophenyl)-5-[4-(pyridin-2-yloxy)phenyl]pyrrol-1-ylmethyl}-pyridin-2-ylamine, afforded the title compound (25.0 mg, 80%) as an off-white solid: R$_f$ 0.45 (97.5:2.5 methylene chloride/methanol); mp 150-155° C.; $^1$H NMR (300 MHz, CD$_3$OD) δ 8.20 (d, J=8.4 Hz, 1H), 8.00 (t, J=8.4 Hz, 1H), 7.67 (t, J=8.4 Hz, 1H), 7.20-7.50 (m, 9H), 7.07 (d, J=8.4 Hz, 1H), 6.70 (d, J=8.1 Hz, 1H), 6.45 (d, J=3.6 Hz, 1H), 6.37 (d, J=3.6 Hz, 1H), 5.88 (d, J=8.1 Hz, 1H), 5.19 (s, 2H); IR (ATR) 3300, 3089, 2921, 2709, 1661, 1627, 1483, 1466, 1427, 1242, 1163, 766, 722 cm$^{-1}$; ESI MS m/z 453 [C$_{27}$H$_{21}$ClN$_4$O+H]$^+$; HPLC (Method 1) 93.7% (AUC), t$_R$=13.38 min.

EXAMPLE 25

Preparation of 6-[2-(2-Chlorophenyl)-5-(4-phenoxyphenyl)pyrrol-1-ylmethyl]pyridin-2-ylamine

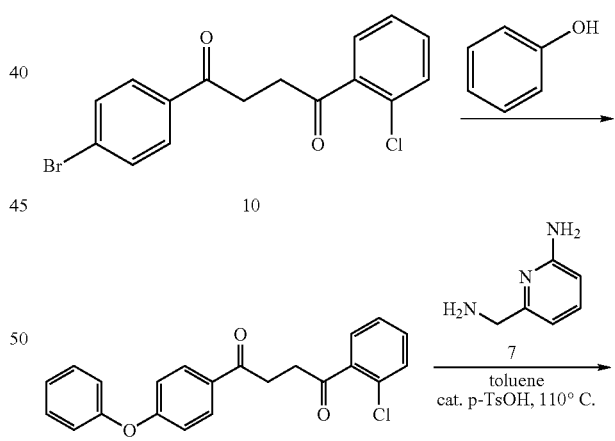

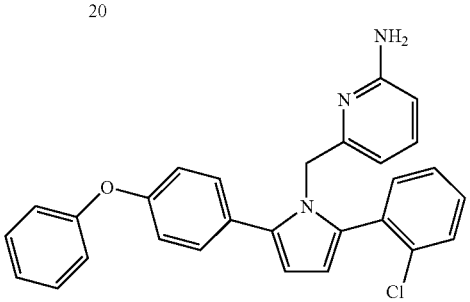

Step 1: Preparation of Intermediate 20

A mixture of 10 (0.352 g, 1.00 mmol), palladium acetate (0.005 g, 0.02 mmol), 2-(di-t-butylphosphino)biphenyl (0.009 g, 0.030 mmol), potassium acetate (0.424 g, 2.00 mmol) and phenol (0.110 g, 1.20 mmol) in toluene (3 mL) was heated at 110° C. for 18 h. The mixture was cooled to room temperature, diluted with ether (40 mL), washed with 1 N NaOH (20 mL) and brine (20 mL), dried over magnesium sulfate, filtered and concentrated to afford an amber syrup. Purification by flash chromatography (silica, 1:10 ethyl acetate/hexanes) afforded 20 (0.132 g, 36%) as a colorless syrup: $^1$H NMR (300 MHz, CDCl$_3$) δ 8.00 (d, J=8.9 Hz, 2H), 7.64 (m, 1H), 7.43-7.20 (m, 6H), 7.08 (dd, J=8.6, 1.2 Hz, 2H), 7.02 (d, J=8.9 Hz, 2H), 3.45-3.36 (m, 4H); ESI MS m/z 365 $[C_{22}H_{17}ClO_3+H]^+$.

Step 2: Preparation of 6-[2-(2-Chlorophenyl)-5-(4-phenoxyphenyl)pyrrol-1-ylmethyl]pyridin-2-ylamine A mixture of 20 (0.129 g, 0.35 mmol), 7 (0.044 g, 0.35 mmol) and p-toluenesulfonic acid (0.004 g, 0.02 mmol) in toluene (10 mL) was heated at 110° C. After 15 h, additional 6-aminomethyl-pyridin-2-ylamine (0.044 g, 0.35 mmol) was added and reflux continued for an additional 24 h. After this time the mixture was cooled and concentrated. Purification of the residue by flash chromatography (silica, 1:3 ethyl acetate/hexanes) afforded the title compound (0.075 g, 51%) as a yellow syrup: $^1$H NMR (300 MHz, CDCl$_3$) δ 7.41-7.10 (m, 10H), 7.01 (d, J=7.8 Hz, 2H), 6.95 (d, J=8.6 Hz, 2H), 6.37 (d, J=3.5 Hz, 1H), 6.32 (d, J=3.5 Hz, 1H), 6.21 (d, J=8.1 Hz, 1H), 5.77 (d, J=7.4 Hz, 1H), 4.99 (s, 2H), 4.22 (s, 2H).

EXAMPLE 26

Preparation of 6-[2-(2-Chlorophenyl)-5-(4-phenoxyphenyl)pyrrol-1-ylmethyl]pyridin-2-ylamine hydrochloride

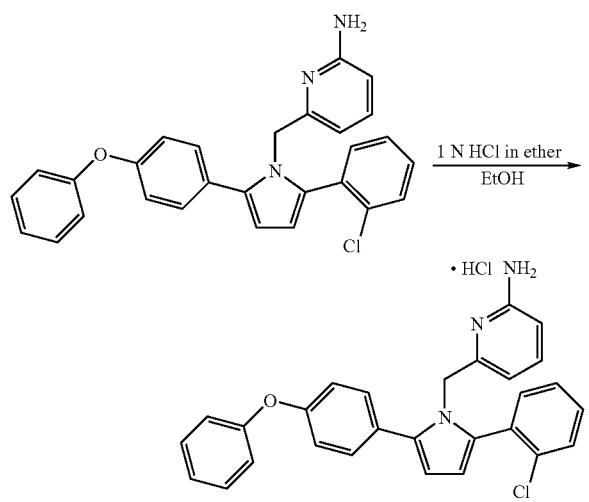

A mixture of 6-[2-(2-chlorophenyl)-5-(4-phenoxyphenyl)pyrrol-1-ylmethyl]pyridin-2-ylamine (0.071 g, 0.16 mmol) and HCl (0.16 mL of a 1.0 M solution in diethyl ether, 0.16 mmol) in ethanol (3 mL) was stirred at room temperature for 8 h. The mixture was concentrated and purified by trituration with ether to afford the title compound, (0.060 g, 78%) as a pale yellow solid: $R_f$ 0.22 (1:3 ethyl acetate/hexanes); mp 145-148° C.; $^1$H NMR (300 MHz, CD$_3$OD) δ 7.64 (dd, J=7.4, 1.4 Hz, 1H), 7.48 (d, J=7.4 Hz, 1H), 7.40-7.27 (m, 7H), 7.13 (t, J=7.4 Hz, 1H), 7.02-6.98 (m, 4H), 6.68 (d, J=8.8 Hz, 1H), 6.39 (d, J=3.6 Hz, 1H), 6.34 (d, J=3.6 Hz, 1H), 5.86 (d, J=7.3 Hz, 1H), 5.14 (s, 2H); IR (ATR) 3081, 1660, 1481, 1231 cm$^{-1}$; ESI MS m/z 452 $[C_{28}H_{22}ClN_3O+H]^+$; HPLC (Method 1) 98.6% (AUC), $t_R$=14.99 min. Anal. Calcd for $C_{28}H_{22}ClN_3O\cdot HCl\cdot 0.25H_2O$: C, 68.23; H, 4.60; N, 8.52. Found: C, 68.29; H, 4.79; N, 8.34.

EXAMPLE 27

Preparation of 6-[2-Biphenyl-4-yl-5-(2-chlorophenyl)pyrrol-1-ylmethyl]pyridin-2-ylamine

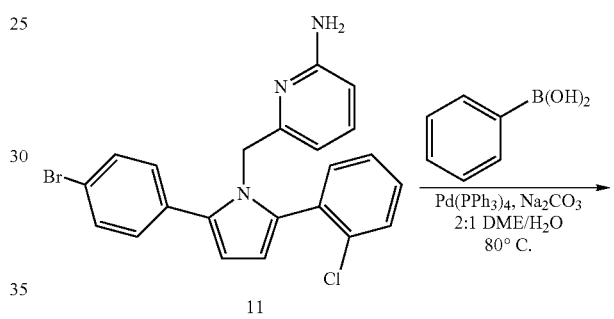

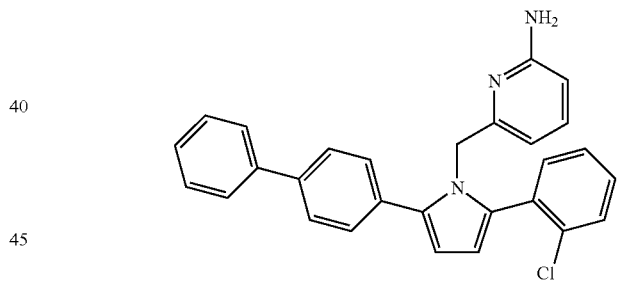

A mixture of 11 (0.048 g, 0.11 mmol), benzene boronic acid (0.016 g, 0.013 mmol), tetrakistriphenylphosphinopalladium(0) (0.006 g, 0.005 mmol) and sodium carbonate (0.035 g, 0.33 mmol) in 2:1 DME/water (3 mL) was heated at 80° C. for 3 h. The mixture was cooled to room temperature and diluted with ethyl acetate (20 mL) then washed with water (10 mL), brine (10 mL), dried over magnesium sulfate, filtered and concentrated. Purification by flash chromatography (silica, 1:3 ethyl acetate/hexanes) afforded the title compound (0.027 g, 56%) as an off-white solid: $R_f$ 0.21 (1:3 ethyl acetate/hexanes); mp 181-185° C.; $^1$H NMR (300 MHz, CDCl$_3$) δ 7.60-7.18 (m, 14H), 6.45 (d, J=3.5 Hz, 1H), 6.34 (d, J=3.5 Hz, 1H), 6.22 (d, J=8.1 Hz, 1H), 5.80 (d, J=7.4 Hz, 1H), 5.06 (s, 2H), 4.21 (s, 2H); IR (ATR) 1639, 1605, 1574 cm$^{-1}$; ESI MS m/z 436 $[C_{28}H_{22}ClN_3+H]^+$; HPLC (Method 1)>99% (AUC), $t_R$=14.99 min.

EXAMPLE 28

Preparation of 6-[(2-(2-Chlorophenyl)-5-[4-(1,2-dihydro-pyridin-3-yl)phenyl]-Pyrrol-1-ylmethyl]pyridin-2-ylamine

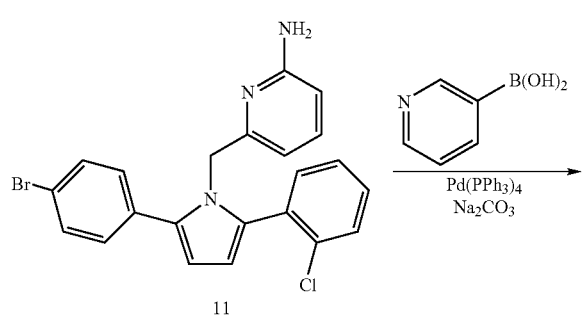

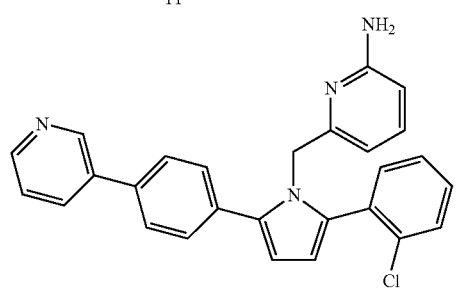

Using essentially the same procedure described in Example 27 hereinabove, and employing 3-pyridinylboronic acid, the title product was obtained. Purification by flash chromatography (silica, 2:1 ethyl acetate/hexanes) afforded the title compound, (0.069 g, 63%) as a white solid: $R_f$ 0.29 (2:1 ethyl acetate/hexanes); mp 163-166° C.; $^1$H NMR (300 MHz, CDCl$_3$) δ 8.85 (d, J=1.7 Hz, 1H), 8.57 (dd, J=4.7, 1.5 Hz, 1H), 7.87 (d, J=7.9 Hz, 1H), 7.55-7.17 (m, 10H), 6.47 (d, J=3.6 Hz, 1H), 6.35 (d, J=3.6 Hz, 1H), 6.22 (d, J=8.3 Hz, 1H), 5.79 (d, J=7.4 Hz, 1H), 5.06 (s, 2H), 4.22 (s, 2H); IR (ATR) 1607, 1572, 1464 cm$^{-1}$; ESI MS m/z 437 [C$_{27}$H$_{21}$ClN$_4$+H]$^+$; HPLC (Method 1)>99% (AUC), $t_R$=10.91 min. Anal. Calcd for C$_{27}$H$_{21}$ClN$_4$·0.25H$_2$O: C, 73.46; H, 4.91; N, 12.69. Found: C, 73.35; H, 4.90; N, 12.33.

EXAMPLE 29

Preparation of 6-[2-(2-Chloro-phenyl)-5-(4-pyrimidin-5-yl-phenyl)-pyrrol-1-ylmethyl]-pyridin-2-ylamine

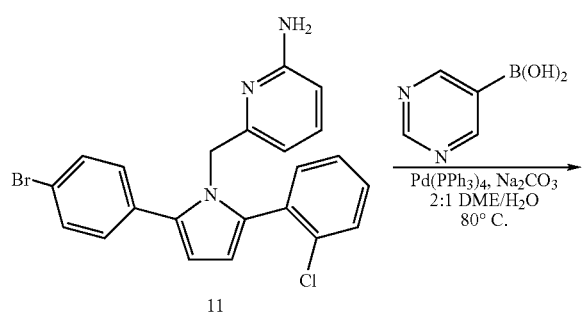

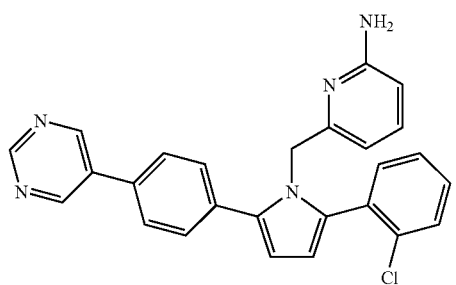

Using essentially the same procedure described in Example 27 hereinabove, and employing 5-pyrimidinylboronic acid, the title product was obtained. Purification by flash chromatography (silica, 3:1 ethyl acetate/hexanes) afforded the title compound (0.061 g, 55%) as a white solid: $R_f$ 0.22 (3:1 ethyl acetate/hexanes); mp 163-164° C.; $^1$H NMR (300 MHz, CDCl$_3$) δ 9.19 (s, 1H), 8.95 (s, 2H), 7.56 (s, 4H), 7.41 (m, 1H), 7.25-7.12 (m, 4H), 6.49 (d, J=3.6 Hz, 1H), 6.36 (d, J=3.6 Hz, 1H), 6.22 (d, J=8.1 Hz, 1H), 5.79 (d, J=7.4 Hz, 1H), 5.05 (s, 2H), 4.23 (s, 2H); IR (ATR) δ 1637, 1603, 1409 cm$^{-1}$; ESI MS m/z 438 [C$_{26}$H$_{20}$ClN$_5$+H]$^+$; HPLC (Method 1)>99% (AUC), $t_R$=12.31 min.

EXAMPLE 30

Preparation of 6-[2-(2-Chloro-phenyl)-5-(4-pyridin-3-yl-phenyl)-pyrrol-1-ylmethyl]-pyridin-2-ylamine Scheme 6

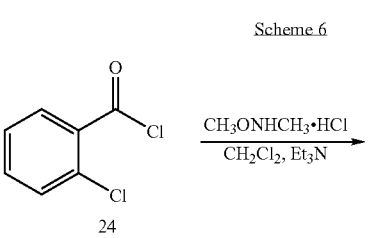

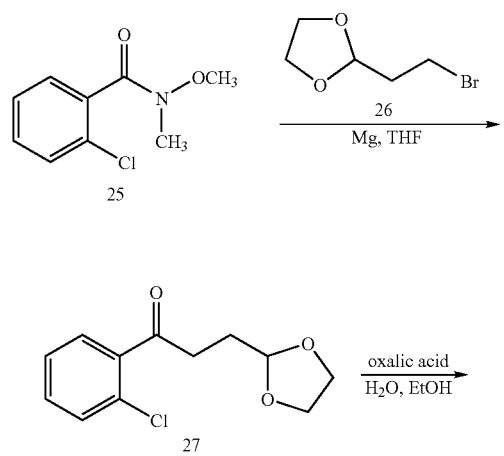

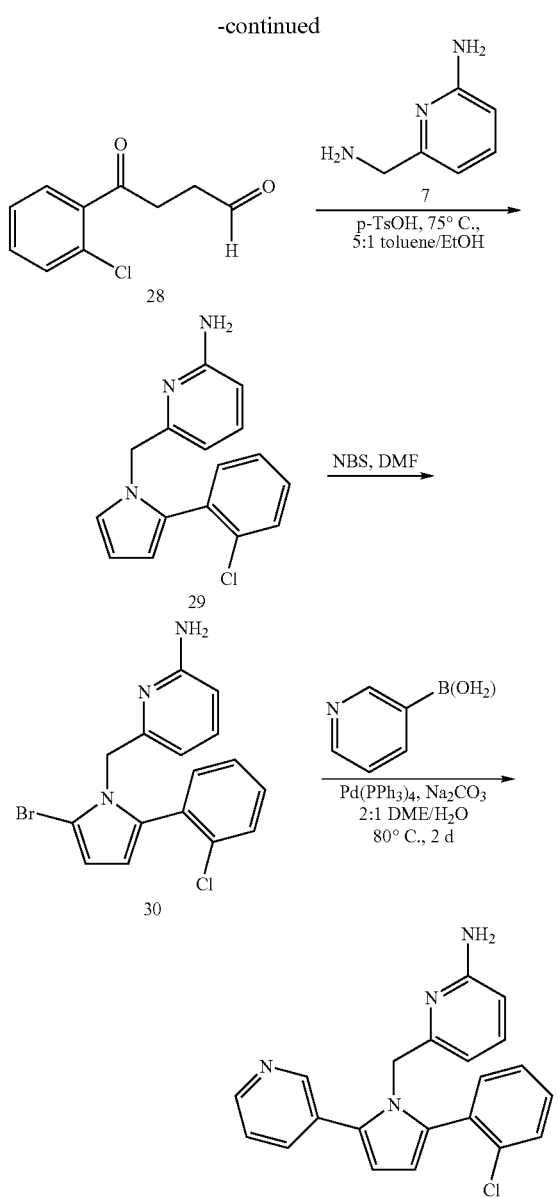

Step 1: Preparation of Intermediate 25

To a stirred ice-cold mixture of N,O-dimethylhydroxylamine hydrochloride (6.13 g, 62.8 mmol) and triethylamine (17.5 g, 126 mmol) in methylene chloride (100 mL) was added dropwise a solution of 2-chlorobenzoyl chloride (10.0 g, 57.1 mmol) over a period of 10 min. The cooling bath was removed and the mixture stirred at room temperature for 20 h. The mixture was then washed with water (100 mL), 1 N HCl (100 mL) and brine (100 mL), dried over magnesium sulfate, filtered and concentrated to afford 25 (10.7 g, 94%) as a colorless liquid: $^1$H NMR (300 MHz, CDCl$_3$) δ 7.43-7.28 (m, 4H), 3.47 (s, 3H), 3.93 (s, 3H); ESI MS m/z 200 $[C_9H_{10}ClNO_2+H]^+$.

Step 2: Preparation of Intermediate 27

To a stirred mixture of 25 (10.7 g, 53.5 mmol) in THF (100 mL) was added, over a period of 10 min, a solution of the Grignard reagent prepared from 2-(2-bromoethyl)-1,3-dioxolane (26, 11.6 g, 64.2 mmol) and magnesium (1.56 g, 64.2 mmol) in THF (125 mL). After stirring at room temperature for 20 h, the mixture was concentrated and partitioned between diethyl ether (150 mL) and 1 N HCl (100 mL). The organic layer was separated and washed with brine (100 mL), dried over magnesium sulfate, filtered and concentrated to afford a yellow liquid. Purification by flash chromatography (silica, 1:4 ethyl acetate/hexanes) afforded 27 (3.72 g, 29%) as a colorless liquid: $^1$H NMR (300 MHz, CDCl$_3$) δ 7.49-7.29 (m, 4H), 4.99 (t, J=4.2 Hz, 1H), 3.97-3.82 (m, 4H), 3.10-3.05 (m, 2H), 2.17-2.10 (m, 2H).

Step 3: Preparation of Intermediate 28

A mixture of 27 (0.750 g, 3.12 mmol) and oxalic acid (0.700 g, 7.79 mmol) in ethanol (15 mL) and water (20 mL) was heated at 75° C. for 2 h. The mixture was cooled to room temperature and diluted with diethyl ether (75 mL). The organic layer was separated then washed with saturated aqueous sodium bicarbonate (50 mL), brine (50 mL), dried over magnesium sulfate, filtered and concentrated to afford 28 (0.580 g, 95%) as a yellow liquid: $^1$H NMR (300 MHz, CDCl$_3$) δ 9.88 (s, 1H), 7.59-7.31 (m, 4H), 3.27 (t, J=6.0 Hz, 2H), 2.95 (t, J=6.0 Hz, 2H).

Step 4: Preparation of Intermediate 29

A mixture of 28 (0.570 g, 2.90 mmol), 7 (0.360 g, 2.90 mmol) and p-toluenesulfonic acid (0.028 g, 0.14 mmol) in 5:1 toluene/ethanol (72 mL) was heated at 75° C. for 15 h. The mixture was cooled and concentrated. Purification by flash chromatography (silica, 1:2 ethyl acetate/hexanes) afforded 29 (0.489 g, 60%) as an off-white solid: R$_f$ 0.31 (1:2 ethyl acetate/hexanes); mp 73-76° C.; $^1$H NMR (300 MHz, CDCl$_3$) δ 7.41 (d, J=6.9 Hz, 1H), 7.30-7.19 (m, 4H), 6.83 (t, J=1.8 Hz, 1H), 6.31-6.23 (m, 3H), 5.96 (d, J=7.5 Hz, 1H), 4.89 (s, 2H), 4.33 (s, 2H); IR (ATR) 1600, 1469, 1454 cm$^{-1}$; ESI MS m/z 284 $[C_{16}H_{14}ClN_3+H]^+$; HPLC (Method 1) 98.5% (AUC), t$_R$=11.56 min. Anal. Calcd for $C_{16}H_{14}ClN_3$: C, 67.72; H, 4.97; N, 14.81. Found: C, 67.35; H, 4.90; N, 14.64.

Step 5: Preparation of Intermediate 30

To a stirred ice-cold solution of 29 (0.421 g, 1.48 mmol) in DMF (5 mL) was added dropwise a solution of N-bromosuccinimide (0.264 g, 1.48 mmol) in DMF (2.5 mL) over a period of 2 min. After stirring for an additional 20 min, the mixture was diluted with ethyl acetate (50 mL), washed with water (30 mL), 5% aqueous lithium chloride (30 mL), and brine (30 mL), dried over magnesium sulfate, filtered and concentrated to afford an amber syrup. This material was combined with crude product from another run, AMRI lot # KDB-E-88, and purified by flash chromatography (silica, 1:3 ethyl acetate/hexanes) to afford 30 (0.501 g, 79%) as an off-white solid: R$_f$ 0.29 (1:3 ethyl acetate/hexanes); mp 91-92° C.; $^1$H NMR (300 MHz, CDCl$_3$) δ 7.42-7.16 (m, 5H), 6.36 (d, J=3.7 Hz, 1H), 6.30 (d, J=8.1 Hz, 1H), 6.26 (d, J=3.8 Hz, 1H), 5.83 (d, J=7.5 Hz, 1H), 4.96 (s, 2H), 4.32 (s, 2H); IR (ATR) 1639, 1602, 1567, 1446 cm$^{-1}$; ESI MS m/z 362 $[C_{16}H_{13}BrClN_3+H]^+$; HPLC (Method 1)>99% (AUC), t$_R$=12.32 min. Anal. Calcd for $C_{16}H_{13}BrClN_3$: C, 52.99; H, 3.61; N, 11.59. Found: C, 52.94; H, 3.57; N, 11.24.

Step 6: Preparation of 6-[2-(2-Chloro-phenyl)-5-(4-pyridin-3-yl-phenyl)-pyrrol-1-ylmethyl]-pyridin-2-ylamine A mixture of 30 (0.100 g, 0.276 mmol), pyridine-3-boronic acid (0.041 g, 0.331 mmol), tetrakistriphenylphosphinopalladium(0) (0.016 g, 0.014 mmol) and sodium carbonate (0.088 g, 0.827 mmol) in 2:1 DME/water (6 mL) was heated at 80° C. for 30 h. After this time, additional pyridine-3-boronic acid (0.021 g, 0.166 mmol) and tetrakistriphenylphosphinopalladium(0) (0.016 g, 0.014 mmol) were added and heating continued at 80° C. for a further 16 h. The mixture was then cooled to room temperature, diluted with ethyl acetate (40 mL), washed with water (20 mL), and brine (20 mL), dried over magnesium sulfate, filtered and concentrated. Purification by flash chromatography (silica, 4:1 ethyl acetate/hexanes) afforded the title compound (0.017 g, 17%) as a pale yellow solid: $R_f$ 0.23 (4:1 ethyl acetate/hexanes); mp 139-145° C.; $^1$H NMR (300 MHz, CDCl$_3$) δ 8.67 (s, 1H), 8.48 (d, J=3.3 Hz, 1H), 7.72 (m, 1H), 7.42 (m, 1H), 7.26-7.18 (m, 5H), 6.46 (d, J=3.3 Hz, 1H), 6.35 (d, J=1.9 Hz, 1H), 6.21 (d, J=8.0 Hz, 1H), 5.76 (d, J=7.5 Hz, 1H), 4.97 (s, 2H), 4.24 (s, 2H); ESI MS m/z 361 $[C_{21}H_{17}ClN_4+H]^+$; HPLC (Method 1)>99% (AUC), $t_R$=10.12 min.

EXAMPLE 31

Preparation of 6-{2-(2-Chloro-phenyl)-5-[4-(Pyrimidin-2-yloxy)-phenyl]-pyrrol-1-ylmethyl}-pyridin-2-ylamine hydrochloride A mixture of 15 (0.060 g, 0.160 mmol) and cesium carbonate (0.056 g, 0.160 mmol) in N-methylpyrrolidinone (1 mL) was degassed and treated with 2-bromopyrimidine (0.025 g, 0.160 mmol), 2,2,6,6-tetramethylheptane-3,5-dione (0.003 g, 0.0160 mmol), and copper(I) chloride (0.008 g, 0.080 mmol). The reaction was degassed again and heated at 120° C. under nitrogen overnight. The reaction was then cooled to room temperature and diluted with ethyl acetate (100 mL) and water (20 mL). The organic layer was separated and washed with brine (3×20 mL), dried over sodium sulfate, filtered and concentrated. Purification by flash chromatography (silica, 98:2 methylene chloride/methanol) and then by preparative HPLC (Method 3) afforded the free amine of the title product (0.032 g, 44%) as a colorless syrup: $^1$H NMR (300 MHz, CD$_3$OD) δ 8.70 (d, J=4.8 Hz, 2H), 7.50-7.00 (m, 10H), 6.42 (d, J=3.6 Hz, 1H), 6.32 (d, J=3.6 Hz, 1H), 6.20 (d, J=8.5 Hz, 1H), 5.85 (d, J=8.5 Hz, 1H), 5.02 (s, 2H).

To a solution of 6-{2-(2-chlorophenyl)-5-[4-(pyrimidin-2-yloxy)-phenyl]pyrrol-1-ylmethyl}pyridin-2-ylamine (0.032 g, 0.070 mmol) in diethyl ether (1 mL) was added a 2.0 M solution of HCl (0.035 mL, 0.070 mmol) in diethyl ether and the mixture stirred at room temperature for 30 min. The suspension was then concentrated and the resulting solid triturated with hexanes to afford the title compound (0.032 g, 86%) as an off-white solid: $R_f$ 0.38 (97.5:2.5 methylene chloride/methanol); mp 135-140° C.; $^1$H NMR (300 MHz, CD$_3$OD) δ 8.60 (d, J=4.8 Hz, 2H), 7.50-7.00 (m, 10H), 6.65 (d, J=8.7 Hz, 1H), 6.44 (d, J=3.6 Hz, 1H), 6.36 (d, J=3.6 Hz, 1H), 5.86 (d, J=8.7 Hz, 1H), 5.16 (s, 2H); IR (ATR) 3303, 3086, 2714, 1662, 1628, 1567, 1484, 1401, 1300, 1211, 902, 855, 757 cm$^{-1}$; ESI MS m/z 454 $[C_{26}H_{20}ClN_5O+H]^+$; HPLC (Method 1) 95.7% (AUC), $t_R$=12.48 min. Anal. Calcd for $C_{26}H_{20}ClN_5O\cdot HCl\cdot 1.25H_2O$: C, 60.88; H, 4.62; N, 13.65. Found: C, 61.12; H, 4.54; N, 13.31.

EXAMPLES 32-36

Preparation of 6-{2-(2-Chlorophenyl)-5-[heteroaryloxy)-phenyl]-pyrrol-1-ylmethyl}-pyridin-2-ylamine hydrochloride Derivatives

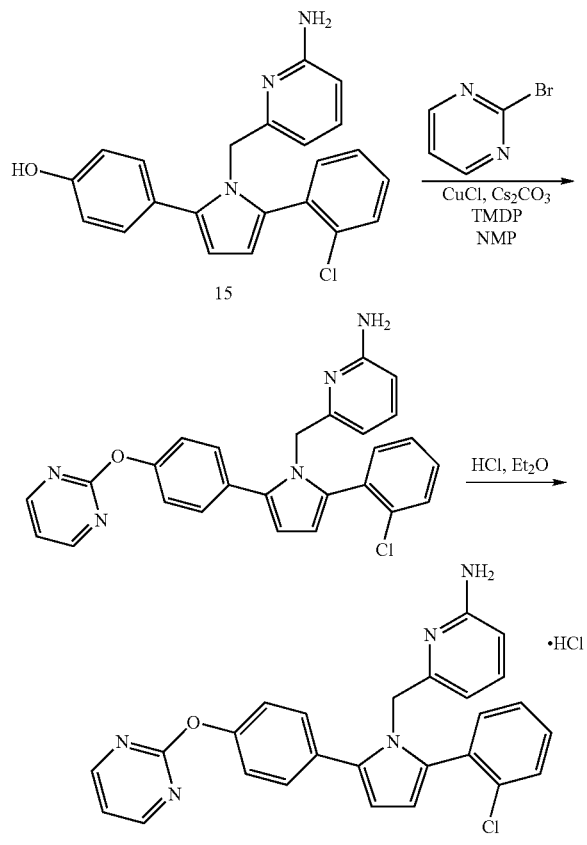

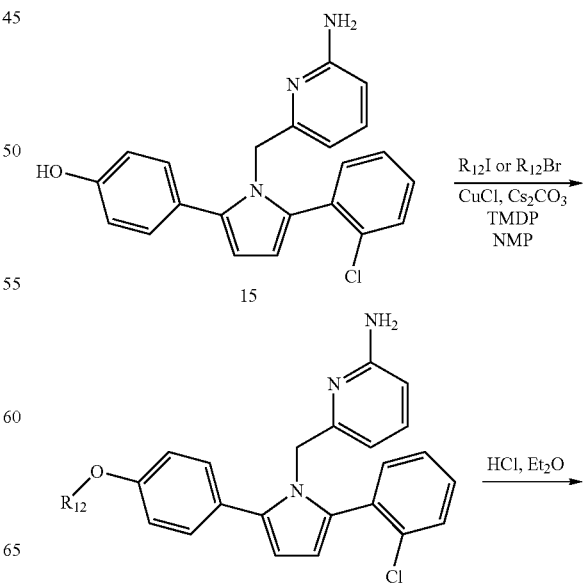

-continued

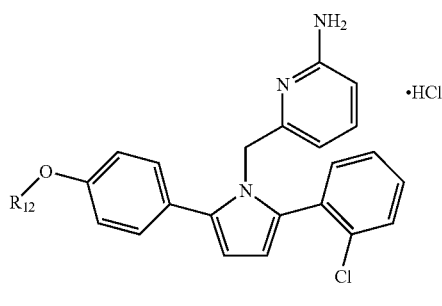

Using essentially the same procedure described hereinabove for Example 31 and employing the appropriate heteroaryl iodide or bromide, the compounds shown in Table III were obtained and identified by HNMR and mass spectral analyses.

TABLE III

| Ex. No. | R12 | mp °C. | Ms m/z |
|---|---|---|---|
| 32 | 2-thiazolyl | 126-130 | 459 |
| 33 | 2-pyrazinyl | 140-148 | 454 |
| 34 | 3-pyridazinyl | 110-120 | 454 |
| 35 | 3-pyridinyl | 130-135 | 453 |
| 36 | 5-pyrimidinyl |  | 454 |

EXAMPLE 37

Preparation of 1-(4-{4-[1-(6-Aminopyridin-2-ylmethyl)-5-(2-chlorophenyl)-1H-pyrrol-2-yl]phenoxy}-phenyl)ethanone hydrochloride

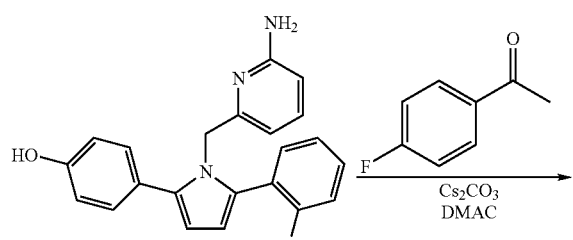

-continued

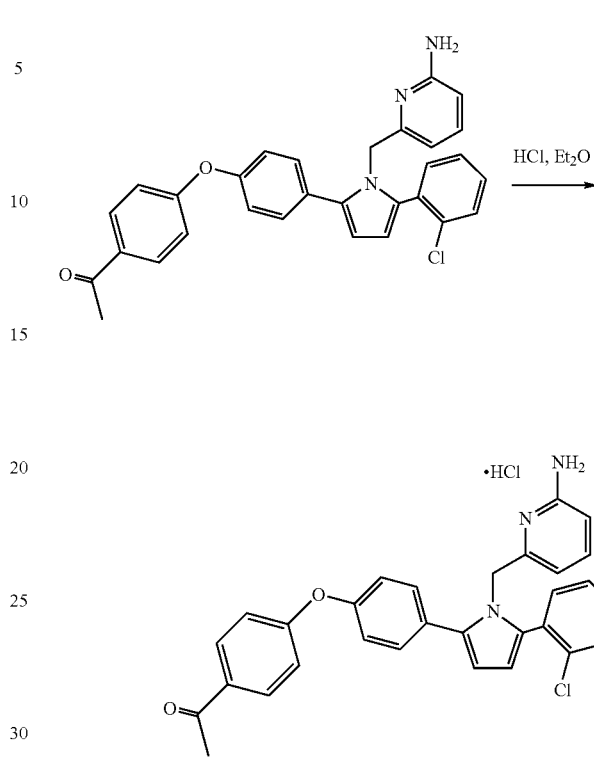

A mixture of 15 (0.050 g, 0.133 mmol), 4'-fluoroacetophenone (0.018 g, 0.133 mmol) and cesium carbonate (0.070 g, 0.200 mmol) in N,N-dimethylacetamide (1 mL) was heated at reflux for 2 h. The reaction was then cooled to room temperature and diluted with ethyl acetate (100 mL) and water (20 mL). The organic layer was separated and washed with brine (3×20 mL), dried over sodium sulfate, filtered and concentrated. Purification by flash chromatography (silica, 98:2 methylene chloride/methanol) and then preparative HPLC (Method 3) afforded the free amine of the title product (0.019 g, 29%) as a colorless syrup: $^1$H NMR (300 MHz, CDCl$_3$) δ 7.95 (d, J=2.1 Hz, 2H), 7.50-6.90 (m, 11H), 6.40 (d, J=3.6 Hz, 1H), 6.33 (d, J=3.6 Hz, 1H), 6.22 (d, J=7.8 Hz, 1H), 5.77 (d, J=7.8 Hz, 1H), 5.01 (s, 2H), 4.25 (s, 2H), 2.57 (s, 3H).

The conversion of 1-(4-{4-[1-(6-aminopyridin-2-ylmethyl)-5-(2-chlorophenyl)-1H-pyrrol-2-yl]phenoxy}-phenyl)ethanone to the hydrochloride salt was performed essentially as described in Example 31 to afford the title compound, (0.019 g, 89%) as an off-white solid: R$_f$ 0.75 (97.5:2.5 methylene chloride/methanol); mp 125-130° C.; $^1$H NMR (300 MHz, CD$_3$OD) δ 8.01 (d, J=8.8 Hz, 2H), 7.75-7.00 (m, 11H), 6.70 (d, J=8.7 Hz, 1H), 6.44 (d, J=3.6 Hz, 1H), 6.38 (d, J=3.6 Hz, 1H), 5.88 (d, J=8.7 Hz, 1H), 5.16 (s, 2H), 2.57 (s, 3H); IR (ATR) 3295, 3081, 1660, 1593, 1481, 1235, 1165, 872, 835, 757, 720 cm$^{-1}$; ESI MS m/z 494 [C$_{30}$H$_{24}$ClN$_3$O$_2$+H]$^+$; HPLC (Method 1) 91.4% (AUC), t$_R$=14.19 min.

EXAMPLE 38

Preparation of 6-[2-[4-(4-Bromophenoxy)phenyl]-5-(2-chlorophenyl)pyrrol-1-ylmethyl]pyridin-2-ylamine hydrochloride

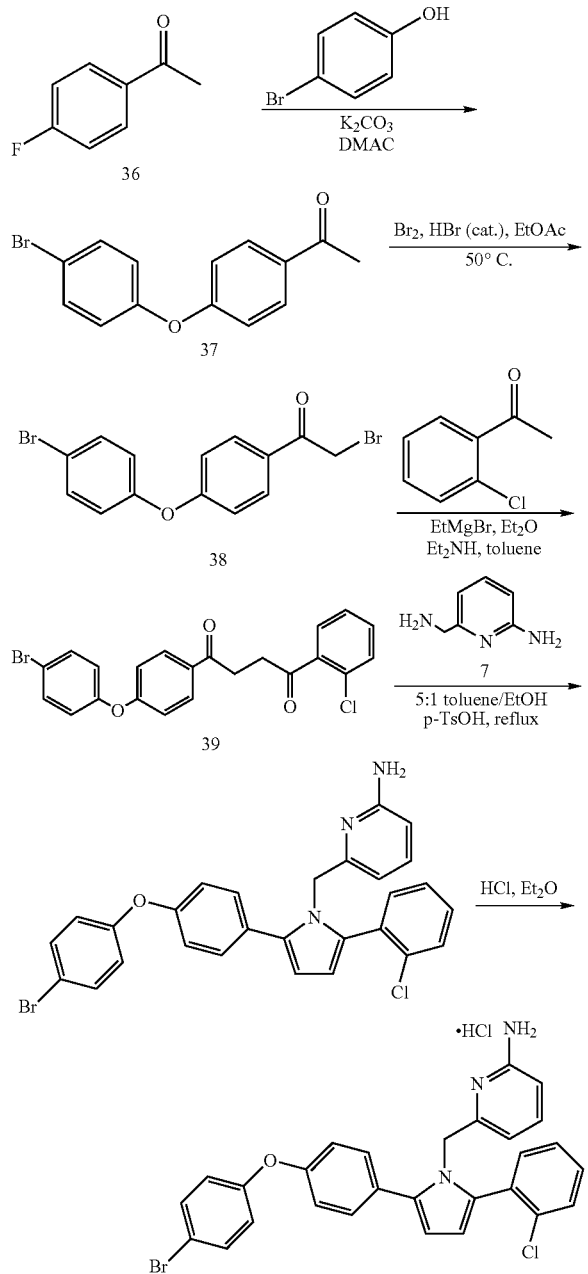

Step 1: Preparation of Intermediate 37

A mixture of 4-bromophenol (2.00 g, 11.6 mmol), 4'-fluoroacetophenone 36 (1.60 g, 11.6 mmol) and potassium carbonate (2.40 g, 17.3 mmol) in N,N-dimethylacetamide (20 mL) was heated at reflux for 2 h. The reaction was cooled to room temperature and diluted with water (100 mL) and ethyl acetate (200 mL). The organic layer was separated and washed with brine (3×100 mL), dried over sodium sulfate, filtered and concentrated to a brown residue. This residue was triturated in water (100 mL) and the solids were collected by filtration and dried to afford 37 (4.02 g, quantitative) as a brown solid: $^1$H NMR (300 MHz, CDCl$_3$) δ 7.95 (d, J=8.7 Hz, 2H), 7.52 (d, J=8.7 Hz, 2H), 7.00 (d, J=8.7 Hz, 2H), 6.95 (d, J=8.7 Hz, 2H), 2.58 (s, 3H).

Step 2: Preparation of Intermediate 38

A mixture of 37 (1.66 g, 5.70 mmol) in ethyl acetate (40 mL) was treated dropwise with bromine (0.870 g, 5.40 mmol) and then 40% hydrogen bromide (0.05 mL). After stirring at room temperature overnight, then at 50° C. for 1 h, the reaction was cooled to room temperature and concentrated. Purification by flash chromatography (silica, 2:98 ethyl acetate/hexanes) afforded 38 (0.94 g, 69%) as a white solid: $^1$H NMR (300 MHz, CDCl$_3$) δ 7.98 (d, J=7.2 Hz, 2H), 7.52 (d, J=6.9 Hz, 2H), 7.02 (d, J=7.2 Hz, 2H), 6.97 (d, J=6.9 Hz, 2H), 4.40 (s, 2H).

Step 3: Preparation of Intermediate 39

A mixture of ethyl magnesium bromide (0.47 mL of a 3.0 M solution in diethyl ether, 1.40 mmol) and diethylamine (0.103 g, 19.4 mmol) in toluene (3 mL) was stirred at room temperature. After 15 min the mixture was placed in an ice bath and treated with a solution of 2'-chloroacetophenone (0.220 g, 1.40 mmol) and 38 (0.420 g, 1.16 mmol) in toluene (2 mL). The reaction was allowed to warm to room temperature over 1 h, then diluted with 1 N HCl (50 mL) and ethyl acetate (200 mL). The organic layer was separated and washed with brine (100 mL), dried over sodium sulfate, filtered and concentrated. Purification by flash chromatography (silica, 0.5:99.5 to 5:95 ethyl acetate/hexanes) afforded 39 (0.220 g, 43%) as a colorless oil: $^1$H NMR (300 MHz, CDCl$_3$) δ 8.00 (d, J=6.6 Hz, 2H), 7.70-6.90 (m, 11H), 3.44 (t, J=4.2 Hz, 2H), 3.38 (t, J=4.2 Hz, 2H).

Step 4: Preparation of 6-[2-[4-(4-Bromo-phenoxy)-phenyl]-5-(2-chlorophenyl)-pyrrol-1-ylmethyl]-pyridin-2-ylamine hydrochloride A mixture of 39 (0.220 g, 0.496 mmol), 7 (0.061 g, 0.496 mmol) and p-toluene sulfonic acid monohydrate (0.009 g, 0.0496 mmol) in 5:1 toluene/ethanol (6 mL) was heated at reflux overnight. The reaction was then cooled to room temperature and concentrated. Purification by flash chromatography (silica, 1:9 to 1:4 ethyl acetate/hexanes) afforded the free amine of the title compound (0.120 g, 46%) as a colorless syrup: ESI MS m/z 530 [C$_{28}$H$_{21}$BrClN$_3$O+H]$^+$.

Conversion of the free amine to the hydrochloride salt was performed essentially as described in Example 31 to afford the title compound (0.090 g, 70%) as an off-white solid: R$_f$ 0.88 (97.5:2.5 methylene chloride/methanol); mp 130-138° C.; $^1$H NMR (300 MHz, CD$_3$OD) δ 7.20-7.70 (m, 9H), 7.04 (d, J=8.7 Hz, 2H), 6.93 (d, J=8.7 Hz, 2H), 6.69 (d, J=8.1 Hz, 1H), 6.40 (d, J=3.6 Hz, 1H), 6.34 (d, J=3.6 Hz, 1H), 5.86 (d, J=8.1 Hz, 1H), 5.15 (s, 2H); IR (ATR) 3290, 3085, 1661, 1477, 1232, 1067, 828, 756, 722 cm$^{-1}$; ESI MS m/z 530 [C$_{28}$H$_{21}$BrClN$_3$O+H]$^+$; HPLC (Method 1)>99% (AUC), t$_R$=16.19 min. Anal. Calcd for C$_{28}$H$_{21}$BrClN$_3$O.HCl.0.5H$_2$O: C, 58.35; H, 4.02; N, 7.29. Found: C, 58.22; H, 3.96; N, 7.09.

EXAMPLE 40

Preparation of 6-[2-(2-Chlorophenyl)-5-(4-pentyloxyphenyl)-pyrrol-1-ylmethyl]-3-methoxypyridin-2-ylamine hydrochloride

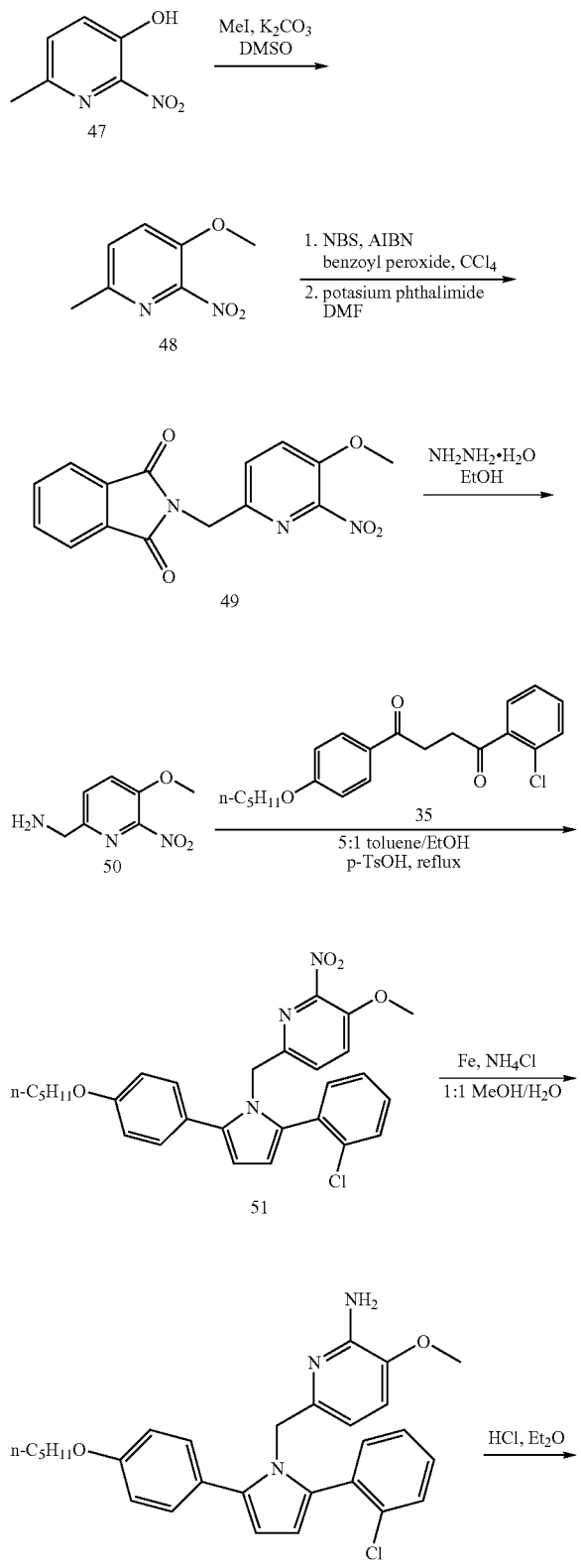

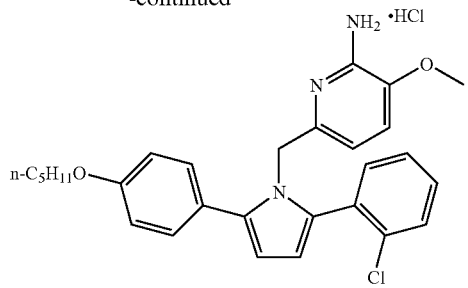

Step 1: Preparation of Intermediate 48

A mixture of 3-hydroxy-6-methyl-2-nitropyridine 47 (15.0 g, 97.3 mmol), potassium carbonate (20.2 g, 146 mmol) and iodomethane (13.8 g, 97.3 mmol) in dimethyl sulfoxide (150 mL) was stirred at room temperature overnight. The reaction was then diluted with ethyl acetate (500 mL) and water (200 mL). The organic layer was separated and washed with brine (3×300 mL), dried over sodium sulfate, filtered and concentrated to afford 48 (15.9 g, 97%) as a white solid: $^1$H NMR (300 MHz, CDCl$_3$) δ 7.72 (d, J=8.4 Hz, 1H), 7.37 (d, J=8.4 Hz, 1H), 3.95 (s, 3H), 2.54 (s, 3H); ESI MS m/z 169 $[C_7H_8N_2O_3+H]^+$.

Step 2: Preparation of Intermediate 49

A mixture of 48 (11.0 g, 66.0 mmol), N-bromosuccinimide (12.8 g, 72.0 mmol), AIBN (1.08 g, 6.60 mmol) and benzoyl peroxide (1.60 g, 6.60 mmol) in carbon tetrachloride (110 mL) was heated at reflux overnight. The mixture was cooled, concentrated and the residue diluted with ethyl acetate (300 mL) and water (100 mL). The organic layer was separated and washed with brine (2×100 mL), dried over sodium sulfate, filtered and concentrated to afford the crude bromide. A mixture of this crude bromide and potassium phthalimide (12.8 g, 69.3 mmol) in N,N-dimethylformamide (80 mL) was stirred at room temperature overnight. The reaction was then diluted with ethyl acetate (300 mL) and water (100 mL), the organic layer separated and washed with brine (2×100 mL), dried over sodium sulfate, filtered and concentrated. Purification of the residue by recrystallization from a mixture of 70:30 ethyl acetate/hexanes afforded 49 (11.0 g, 68%) as a white solid: $^1$H NMR (300 MHz, CDCl$_3$) δ 7.90 (m, 2H), 7.75 (m, 2H), 7.52 (d, J=8.4 Hz, 1H), 7.45 (d, J=8.4 Hz, 1H), 4.98 (s, 2H), 3.94 (s, 3H); ESI MS m/z 314 $[C_{15}H_{11}N_3O_5+H]^+$.

Step 3: Preparation of Intermediate 50

A mixture of 49 (11.0 g, 35.1 mmol) and hydrazine monohydrate (1.85 g, 37.0 mmol) in ethanol (100 mL) was heated at reflux for 2 h. After cooling to room temperature, 2 N HCl (19.3 mL, 38.6 mmol) was added and stirring continued for 30 min. The resulting mixture was then concentrated and water (100 mL) was added. The insolubles were removed by filtration and the filtrate washed with ethyl acetate (100 mL), neutralized with sodium bicarbonate (3.28 g, 39.0 mmol) and concentrated to afford a solid residue. Ethanol (200 mL) was added to this residue and the insolubles removed by filtration. The filtrate was concentrated to afford 50 (4.62 g, 72%) as a white solid: $^1$H NMR (300 MHz, CD$_3$OD) δ 7.80 (d, J=8.7 Hz, 1H), 7.65 (d, J=8.7 Hz, 1H), 3.97 (s, 3H), 3.87 (s, 2H); ESI MS m/z 184 $[C_7H_9N_3O_3+H]^+$.

Step 4: Preparation of Intermediate 51

A mixture of 50 (0.840 g, 2.34 mmol), 35 (0.430 g, 2.34 mmol) and p-toluene sulfonic acid monohydrate (0.045 g, 0.234 mmol) in 5:1 toluene/ethanol (12 mL) was heated at reflux overnight. As the reaction was incomplete, the mixture was then transferred to a sealed tube and heated at 150° C. for 7 h. The reaction was cooled to room temperature, concentrated and the residue diluted with ethyl acetate (300 mL) and water (100 mL). The organic layer was separated and washed with brine (2×50 mL), dried over sodium sulfate, filtered and concentrated. Purification by flash chromatography (silica, 1:19 to 1:4 ethyl acetate/hexanes) afforded the title compound 0.280 g, 24%) as a yellow oil: $R_f$ 0.79 (50:50 ethyl acetate/hexanes); $^1$H NMR (300 MHz, CD$_3$OD) δ 7.60-7.20 (m, 7H), 6.91 (d, J=7.5 Hz, 2H), 6.61 (d, J=9.0 Hz, 1H), 6.27 (d, J=3.6 Hz, 1H), 6.24 (d, J=3.6 Hz, 1H), 5.06 (s, 2H), 3.96 (t, J=6.6 Hz, 2H), 3.86 (s, 3H), 1.77 (tt, J=7.2, 6.6 Hz, 2H), 1.60-1.30 (m, 4H), 0.92 (t, J=7.2 Hz, 3H); APCI MS m/z 506 [C$_{28}$H$_{28}$ClN$_3$O$_4$+H]$^+$; HPLC (Method 1) 98.3% (AUC), $t_R$=27.96 min.

Step 5: Preparation of 6-[2-(2-Chloro-phenyl)-5-(4-pentyloxy-phenyl)-pyrrol-1-ylmethyl]-3-methoxy-pyridin-2-ylamine hydrochloride A mixture of 51 (0.050 g, 0.099 mmol), ammonium chloride (0.053 g, 0.990 mmol) and iron powder (0.039 g, 0.990 mmol) in 1:1 water/methanol (20 mL) was heated at reflux overnight. The reaction was cooled to room temperature, concentrated and diluted with ethyl acetate (100 mL) and sodium bicarbonate (50 mL). The organic layer was separated, washed with brine (50 mL), dried over sodium sulfate, filtered and concentrated. Purification by flash chromatography (silica, 1:19 to 2:3 ethyl acetate/hexanes) afforded the free amine of the title product, (0.030 g, 64%) as a colorless oil: $^1$H NMR (300 MHz, CD$_3$OD) δ 7.50-7.00 (m, 6H), 6.74 (d, J=8.7 Hz, 2H), 6.69 (d, J=8.1 Hz, 1H), 6.15 (d, J=3.6 Hz, 1H), 6.10 (d, J=3.6 Hz, 1H), 5.54 (d, J=8.1 Hz, 1H), 4.77 (s, 2H), 3.82 (t, J=6.3 Hz, 2H), 3.61 (s, 3H), 1.70-1.50 (m, 2H), 1.50-1.20 (m, 4H), 0.85 (t, J=7.2 Hz, 3H); ESI MS m/z 476 [C$_{28}$H$_{30}$ClN$_3$O$_2$+H]$^+$.

The conversion of the free amine to the hydrochloride salt was performed exxentially as described in Example 31 to afford the title compound (0.028 g, 87%) as an off-white solid: $R_f$ 0.71 (50:50 hexanes/ethyl acetate); mp 55-60° C.; $^1$H NMR (300 MHz, CD$_3$OD) δ 7.20-7.50 (m, 6H), 7.12 (d, J=8.1 Hz, 1H), 6.93 (d, J=8.7 Hz, 2H), 6.30 (d, J=3.6 Hz, 1H), 6.28 (d, J=3.6 Hz, 1H), 5.80 (d, J=8.1 Hz, 1H), 5.02 (s, 2H), 3.97 (t, J=6.3 Hz, 2H), 3.89 (s, 3H), 1.77 (tt, J=6.9, 6.3 Hz, 2H), 1.20-1.50 (m, 4H), 0.94 (t, J=6.9 Hz, 3H); IR (ATR) 3303, 3149, 2931, 2868, 1661, 1610, 1572, 1484, 1271, 1245, 1011, 833, 758 cm$^{-1}$; ESI MS m/z 476 [C$_{28}$H$_{30}$ClN$_3$O$_2$+H]+; HPLC (Method 1) 98.7% (AUC), $t_R$=16.68 min. Anal. Calcd for C$_{28}$H$_{30}$ClN$_3$O$_2$·HCl·H$_2$O: C, 63.39; H, 6.27; N, 7.92. Found: C, 63.87; H, 6.07; N, 7.54.

EXAMPLE 41

Preparation of 3-{6-[2-(2-Chloro-phenyl)-5-(4-pentyloxy-phenyl)-pyrrol-1-ylmethyl]-3-methoxy-pyridin-2-ylamino}-propan-1-ol hydrochloride

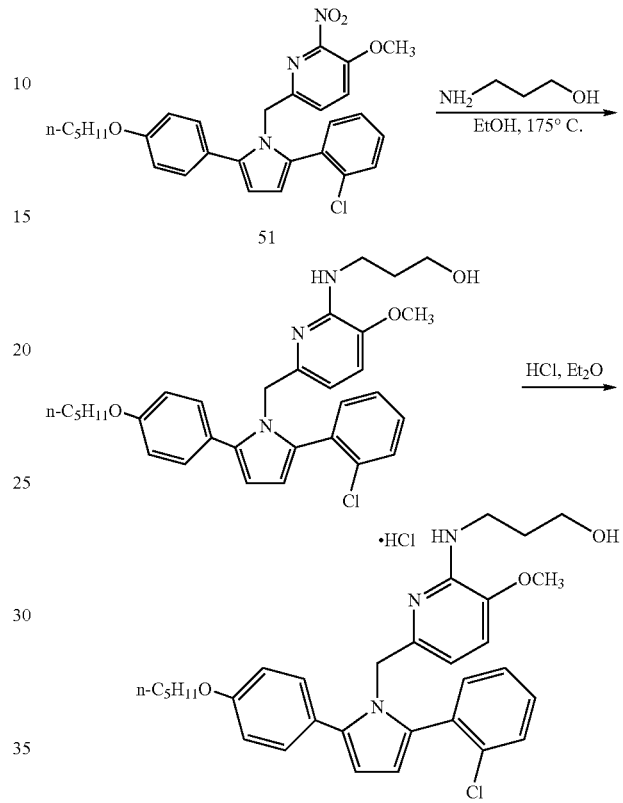

A mixture of 51 (0.150 g, 0.300 mmol) and 3-amino-1-propanol (0.070 g, 0.890 mmol) in ethanol (20 mL) was heated at 125° C. in a sealed tube overnight, then at 175° C. in a sealed tube for 24 h. The reaction was cooled to room temperature and concentrated. Purification by flash chromatography (silica, 3:7 to 1:1 ethyl acetate/hexanes) afforded the free amine of the title product, (0.0791 g, 49%) as a bright yellow syrup: $^1$H NMR (300 MHz, CDCl$_3$) δ 7.50-7.10 (m, 6H), 6.83 (d, J=8.7 Hz, 2H), 6.58 (d, J=8.1 Hz, 1H), 6.30 (d, J=3.3 Hz, 1H), 6.29 (d, J=3.3 Hz, 1H), 5.60 (d, J=8.1 Hz, 1H), 4.97 (s, 2H), 4.80-4.70 (br s, 1H), 3.92 (t, J=6.6 Hz, 2H), 3.72 (s, 3H), 3.50-3.30 (m, 4H), 1.50-1.90 (m, 4H), 1.20-1.50 (m, 4H), 0.93 (t, J=6.9 Hz, 3H); ESI MS m/z 534 [C$_{31}$H$_{36}$ClN$_3$O$_3$+H]$^+$.

The conversion of the free amine to the hydrochloride salt was performed essentially as described in Example 31 to afford the title compound (0.070 g, 83%) as an off-white solid: $R_f$ 0.57 (50:50 hexanes/ethyl acetate); mp 86-88° C.; $^1$H NMR (300 MHz, CD$_3$OD) δ 7.50-7.20 (m, 6H), 7.03 (d, J=7.9 Hz, 1H), 6.93 (d, J=8.7 Hz, 2H), 6.30 (d, J=3.3 Hz, 1H), 6.27 (d, J=3.3 Hz, 1H), 5.69 (d, J=7.9 Hz, 1H), 5.06 (s, 2H), 3.96 (t, J=6.6 Hz, 2H), 3.86 (s, 3H), 3.52 (t, J=6.0 Hz, 2H), 3.35 (t, J=6.6 Hz, 2H), 1.90-1.50 (m, 4H), 1.50-1.20 (m, 4H), 0.93 (t, J=7.0 Hz, 3H); IR (ATR) 3256, 2931, 2868, 1637, 1580, 1485, 1459, 1268, 1245, 1011, 833, 757 cm$^{-1}$; ESI MS m/z 534 [C$_{31}$H$_{36}$ClN$_3$O$_3$+H]$^+$; HPLC (Method 1) 98.0% (AUC), $t_R$=15.79 min. Anal. Calcd for C$_{31}$H$_{36}$ClN$_3$O$_3$·HCl·H$_2$O: C, 63.26; H, 6.68; N, 7.14. Found: C, 63.09; H, 6.60; N, 6.89.

EXAMPLES 42A AND 42B

Preparation of 2-Amino-6-[2-(2-chlorophenyl)-5-(4-pentyloxyphenyl)pyrrol-1-ylmethyl]pyridin-3-ol hydrochloride (A) and 6-[2-(2-Chlorophenyl)-5-(4-pentyloxyphenyl)pyrrol-1-ylmethyl]pyridine-2,3-diamine hydrochloride (B)

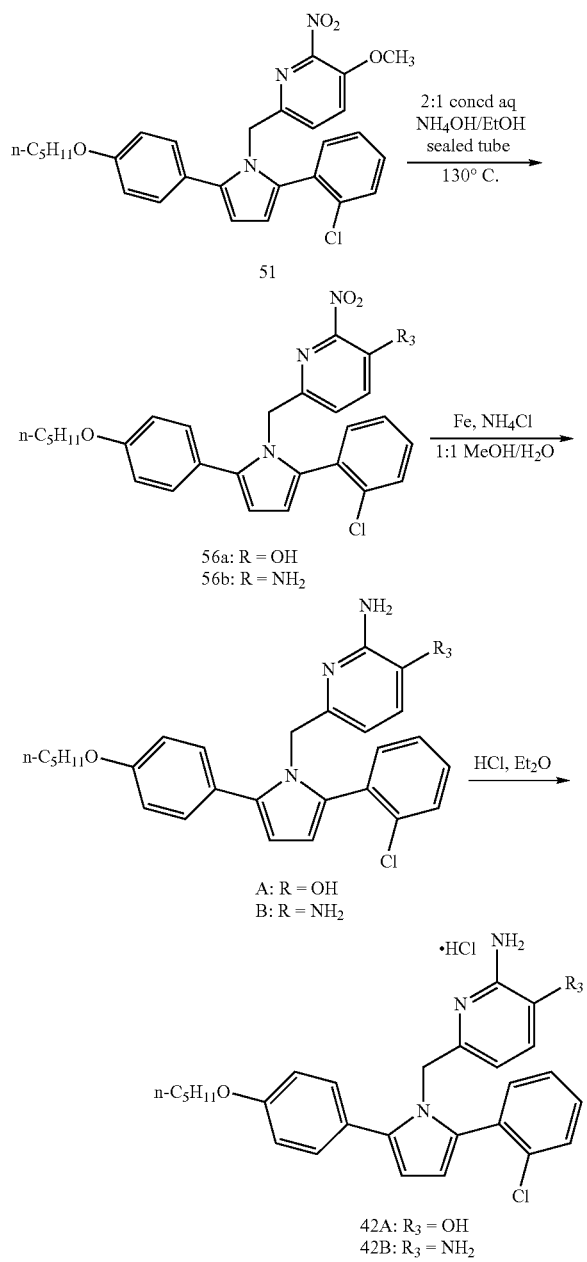

Step 1: Preparation of Intermediates 56a and 56b

A mixture of 51 (0.800 g, 1.58 mmol) in 30% aqueous ammonium hydroxide (50 mL) and ethanol (25 mL) was heated at 130° C. in a sealed tube overnight. The reaction was cooled to room temperature, concentrated and diluted with ethyl acetate (300 mL) and water (50 mL). The organic layer was separated and washed with brine (20 mL), dried over sodium sulfate, filtered and concentrated. Purification by flash chromatography (silica, 1:1 methylene chloride/hexanes) afforded 56a (0.322 g, 41%) as a yellow syrup: $^1$H NMR (300 MHz, CDCl$_3$) δ 10.03 (s, 1H), 7.50-7.10 (m, 7H), 6.86 (d, J=8.7 Hz, 2H), 6.50 (d, J=8.7 Hz, 1H), 6.36 (s, 2H), 5.19 (s, 2H), 3.93 (t, J=6.3 Hz, 2H), 1.90-1.20 (m, 6H), 0.93 (t, J=6.9 Hz, 3H); ESI MS m/z 492 [C$_{27}$H$_{26}$ClN$_3$O$_4$+H]$^+$. Further elution gave 56b (0.267 g, 34%) as a yellow syrup: $^1$H NMR (300 MHz, CDCl$_3$) δ 7.50-7.10 (m, 6H), 7.04 (d, J=8.7 Hz, 1H), 6.85 (d, J=8.7 Hz, 2H), 6.34 (s, 2H), 6.33 (d, J=8.7 Hz, 1H), 5.76 (s, 2H), 5.15 (s, 2H), 3.94 (t, J=6.6 Hz, 2H), 1.90-1.20 (m, 6H), 0.93 (t, J=6.9 Hz, 3H); ESI MS m/z 491 [C$_{27}$H$_{27}$ClN$_4$O$_3$+H]$^+$.

Step 2: Preparation of 2-Amino-6-[2-(2-chlorophenyl)-5-(4-pentyloxyphenyl)-pyrrol-1-ylmethyl]pyridin-3-ol hydrochloride (42A)

The reduction of 56a was performed essentially as described in Example 40, step 5. Purification by flash chromatography (silica, 99:1 to 97:3 methylene chloride/methanol) afforded 2-amino-6-[2-(2-chlorophenyl)-5-(4-pentyloxyphenyl)-pyrrol-1-ylmethyl]pyridin-3-ol (A) (0.015 g, 18%) as a colorless syrup: $^1$H NMR (500 MHz, CD$_3$OD) δ 7.50-7.20 (m, 6H), 6.86 (m, 2H), 6.66 (d, J=8.0 Hz, 1H), 6.23 (d, J=3.5 Hz, 1H), 6.19 (d, J=3.5 Hz, 1H), 5.66 (d, J=8.0 Hz, 1H), 4.87 (s, 2H), 3.95 (t, J=6.5 Hz, 2H), 1.80-1.70 (m, 2H), 1.50-1.30 (m, 4H), 0.94 (t, J=6.9 Hz, 3H); ESI MS m/z 462 [C$_{27}$H$_{28}$ClN$_3$O$_2$+H]$^+$.

The conversion of A to the hydrochloride salt was performed essentially as described in Example 31 to afford the title compound (0.013 g, 80%) as an off-white solid: R$_f$ 0.64 (95:5 methylene chloride/methanol); mp 92-95° C.; $^1$H NMR (300 MHz, CD$_3$OD) δ 7.50-7.20 (m, 6H), 6.95 (m, 2H), 6.92 (d, J=8.0 Hz, 1H), 6.30 (d, J=3.5 Hz, 1H), 6.28 (d, J=3.5 Hz, 1H), 5.76 (d, J=8.0 Hz, 1H), 5.03 (s, 2H), 3.98 (t, J=6.5 Hz, 2H), 1.80-1.70 (m, 2H), 1.50-1.20 (m, 4H), 0.95 (t, J=7.5 Hz, 3H); ESI MS m/z 462 [C$_{27}$H$_{28}$ClN$_3$O$_2$+H]$^+$; HPLC (Method 1) >99% (AUC), $t_R$=15.30 min.

Step 3: Preparation of 6-[2-(2-Chlorophenyl)-5-(4-pentyloxyphenyl)pyrrol-1-ylmethyl]pyridine-2,3-diamine hydrochloride (42B)

The reduction of 56b was performed essentially as described in Example 40, step 5. Purification by flash chromatography (silica, 98:2 methylene chloride/methanol) afforded 6-[2-(2-Chlorophenyl)-5-(4-pentyloxyphenyl)pyrrol-1-ylmethyl]pyridine-2,3-diamine (B) (0.014 g, 74%) as a colorless syrup: $^1$H NMR (300 MHz, CD$_3$OD) δ 7.50-7.20 (m, 6H), 6.83 (d, J=8.7 Hz, 2H), 6.71 (d, J=7.8 Hz, 1H), 6.24 (d, J=3.3 Hz, 1H), 6.19 (d, J=3.3 Hz, 1H), 5.58 (d, J=7.8 Hz, 1H), 4.87 (s, 2H), 3.94 (t, J=6.3 Hz, 2H), 1.80-1.60 (m, 2H), 1.50-1.20 (m, 4H), 0.94 (t, J=6.9 Hz, 3H); ESI MS m/z 461 [C$_{27}$H$_{29}$ClN$_4$O+H]$^+$.

The conversion of B to the hydrochloride salt was performed essentially as described in Example 31 to afford the title compound, (0.013 g, 86%) as an off-white solid: R$_f$ 0.45 (97.5:2.5 methylene chloride/methanol); mp 95-100° C.; $^1$H NMR (300 MHz, CD$_3$OD) δ 7.50-7.20 (m, 6H), 6.93 (d, J=8.7 Hz, 2H), 6.86 (d, J=8.1 Hz, 1H), 6.29 (d, J=3.3 Hz, 1H), 6.27 (d, J=3.3 Hz, 1H), 5.78 (d, J=8.1 Hz, 1H), 5.02 (s, 2H), 3.97 (t, J=6.3 Hz, 2H), 1.80-1.60 (m, 2H), 1.50-1.20 (m, 4H), 0.93 (t, J=6.9 Hz, 3H); ESI MS m/z 461 [C$_{27}$H$_{29}$ClN$_4$O+H]+; HPLC (Method 1) 96.6% (AUC), $t_R$=15.80 min.

EXAMPLES 43A AND 43B

Preparation of 3-{(2-Amino-6-[2-(2-chlorophenyl)-5-(4-pentyloxyphenyl)pyrrol-1-ylmethyl]pyridin-3-yloxy}propan-1-ol hydrochloride (43A) and 4-{2-Amino-6-[2-(2-chlorophenyl)-5-(4-pentyloxyphenyl)pyrrol-1-ylmethyl]-pyridin-3-yloxy}butyronitrile hydrochloride (43B)

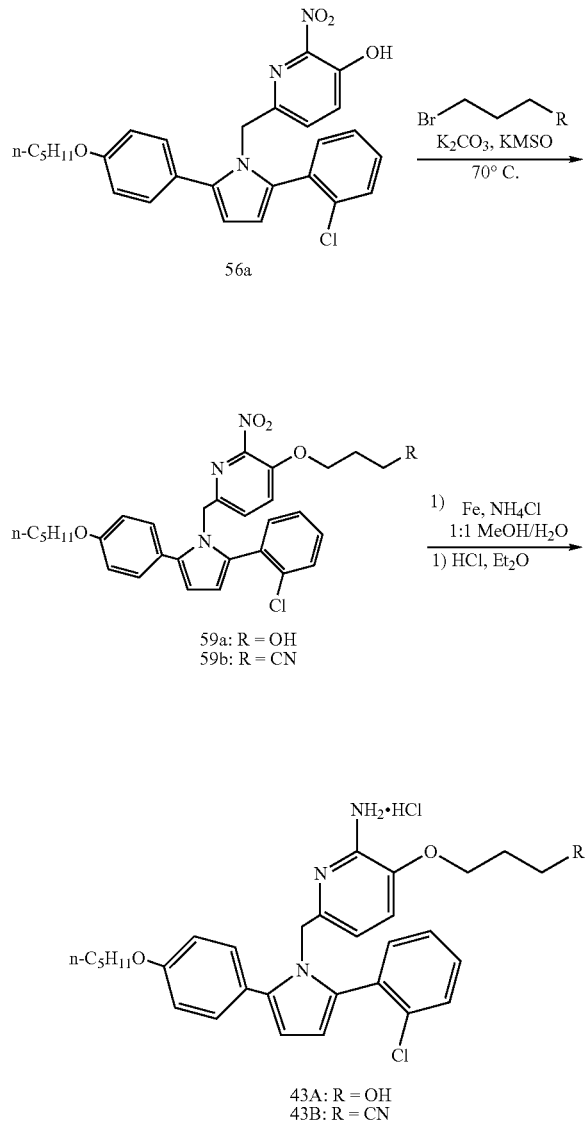

Step 1: Preparation of Intermediate 59a

A mixture of 56a (0.050 g, 0.100 mmol), potassium carbonate (0.030 g, 0.200 mmol) and 3-bromo-1-propanol (0.015 g, 0.110 mmol) in dimethyl sulfoxide (3 mL) was heated at 70° C. for 1.5 h. The reaction was then cooled to room temperature and diluted with ethyl acetate (100 mL) and water (50 mL). The organic layer was separated and washed with brine (3×50 mL), dried over sodium sulfate, filtered and concentrated. Purification by flash chromatography (silica, 98:2 methylene chloride/methanol) afforded 59a (0.035 g, 64%) as a yellow syrup: $^1$H NMR (300 MHz, CD$_3$OD) δ 7.60-7.20 (m, 7H), 6.88 (m, 2H), 6.47 (d, J=8.4 Hz, 1H), 6.35 (s, 2H), 5.14 (s, 2H), 4.30-4.30 (m, 6H), 2.20-1.00 (m, 8H), 0.92 (t, J=7.2 Hz, 3H); ESI MS m/z 550 [C$_{30}$H$_{32}$ClN$_3$O$_5$+ H]$^+$.

Step 2: Preparation of 3-{2-Amino-6-[2-(2-chlorophenyl)-5-(4-pentyloxy-phenyl)-pyrrol-1-ylmethyl]-pyridin-3-yloxy}-propan-1-ol hydrochloride The reduction of 59a was performed essentially as described in Example 40, step 5. Purification by flash chromatography (silica, 98:2 methylene chloride/methanol) afforded 3-{2-amino-6-[2-(2-chloro-phenyl)-5-(4-pentyloxy-phenyl)-pyrrol-1-ylmethyl]-pyridin-3-yloxy}-propan-1-ol (0.033 g, quantitative) as a colorless syrup: $^1$H NMR (300 MHz, CD$_3$OD) δ 7.50-7.20 (m, 6H), 6.85 (d, J=8.7 Hz, 2H), 6.84 (d, J=7.8 Hz, 1H), 6.24 (d, J=3.6 Hz, 1H), 6.22 (d, J=3.6 Hz, 1H), 5.63 (d, J=7.8 Hz, 1H), 4.85 (s, 2H), 3.71 (t, J=6.3 Hz, 2H), 3.35 (t, J=6.0 Hz, 2H), 3.51 (t, J=6.6 Hz, 2H), 1.95 (t, J=6.6 Hz, 2H), 1.80-1.70 (m, 2H), 1.50-1.20 (m, 4H), 0.94 (t, J=6.9 Hz, 3H); ESI MS m/z 520 [C$_{30}$H$_{34}$ClN$_3$O$_3$+ H]$^+$.

The conversion of 3-{2-amino-6-[2-(2-chloro-phenyl)-5-(4-pentyloxy-phenyl)-pyrrol-1-ylmethyl]-pyridin-3-yloxy}-propan-1-ol to the hydrochloride salt was performed essentially as described in Example 31 to afford the title compound (0.030 g, 85%) as an off-white solid: R$_f$ 0.75 (95:5 methylene chloride/methanol); mp 120-130° C.; $^1$H NMR (300 MHz, CD$_3$OD) δ 7.50-7.20 (m, 6H), 7.17 (d, J=8.1 Hz, 1H), 6.93 (d, J=8.4 Hz, 2H), 6.30 (d, J=3.6 Hz, 1H), 6.29 (d, J=3.6 Hz, 1H), 5.80 (d, J=8.1 Hz, 1H), 5.06 (s, 2H), 4.15 (t, J=6.0 Hz, 2H), 3.97 (t, J=6.3 Hz, 2H), 3.71 (t, J=6.0 Hz, 2H), 2.10-1.70 (m, 4H), 1.50-1.20 (m, 4H), 0.94 (t, J=6.9 Hz, 3H); IR (ATR) 3299, 3155, 2931, 2870, 1660, 1570, 1486, 1467, 1270, 1245, 1176, 1041, 831, 759 cm$^{-1}$; ESI MS m/z 520 [C$_{30}$H$_{34}$ClN$_3$O$_3$+H]$^+$; HPLC (Method 1) 96.8% (AUC), t$_R$=15.49 min. Anal. Calcd for C$_{30}$H$_{34}$ClN$_3$O$_3$.HCl.1.5H$_2$O: C, 61.75; H, 6.56; N, 7.20. Found: C, 61.94; H, 6.34; N, 6.86.

Step 3: Preparation of Intermediate 59b

The reaction of 56a with 4-bromobutyronitrile was performed essentially as described in step 1 hereinabove. The reaction was then cooled to room temperature and diluted with ethyl acetate (100 mL) and water (30 mL). The organic layer was separated and washed with brine (3×20 mL), dried over sodium sulfate, filtered and concentrated to afford 59b (0.10 g, 98%) as a yellow syrup: $^1$H NMR (300 MHz, CD$_3$OD) δ 7.60-7.20 (m, 7H), 6.87 (m, 2H), 6.50 (d, J=8.5 Hz, 1H), 6.35 (m, 2H), 5.15 (s, 2H), 4.10-4.00 (m, 2H), 3.95 (t, J=6.5 Hz, 2H), 2.58 (t, J=7.0 Hz, 2H), 2.20-1.20 (m, 8H), 0.91 (t, J=7.0 Hz, 3H); ESI MS m/z 559 [C$_{31}$H$_{31}$ClN$_4$O$_4$+ H]$^+$.

Step 4: Preparation of 4-{2-Amino-6-[2-(2-chlorophenyl)-5-(4-pentyloxy-phenyl)pyrrol-1-ylmethyl]pyridin-3-yloxy}butyronitrile hydrochloride (43B)

The reduction of 59b was performed essentially as described in Example 40, step 5. Purification by flash chromatography (silica, 99.5:0.5 methylene chloride/methanol) afforded 4-{2-amino-6-[2-(2-chlorophenyl)-5-(4-pentyloxyphenyl)-pyrrol-1-ylmethyl]pyridin-3-yloxy}butyronitrile (0.070 g, 74%) as a colorless syrup: $^1$H NMR (300 MHz, CD$_3$OD) δ 7.50-7.20 (m, 6H), 6.85 (d, J=8.7 Hz, 2H), 6.84 (d, J=7.8 Hz, 1H), 6.24 (d, J=3.6 Hz, 1H), 6.22 (d, J=3.6 Hz, 1H), 5.63 (d, J=7.8 Hz, 1H), 4.85 (s, 2H), 3.71 (t, J=6.3 Hz, 2H), 3.35 (t, J=6.0 Hz, 2H), 3.51 (t, J=6.6 Hz, 2H), 1.95 (t, J=6.6 Hz, 2H), 1.80-1.70 (m, 2H), 1.50-1.20 (m, 4H), 0.94 (t, J=6.9 Hz, 3H); ESI MS m/z 529 [C$_{31}$H$_{33}$ClN$_4$O$_2$+H]$^+$.

The conversion of 4-{2-amino-6-[2-(2-chlorophenyl)-5-(4-pentyloxyphenyl)-pyrrol-1-ylmethyl]pyridin-3-yloxy}butyronitrile to the hydrochloride salt was performed essentially as described in Example 31 to afford the title compound (0.070 g, 94%) as an off-white solid: R$_f$ 0.69 (97.5:2.5 methylene chloride/methanol); mp 65-73° C.; $^1$H NMR (300 MHz, CD$_3$OD) δ 7.50-7.20 (m, 6H), 7.04 (d, J=8.1 Hz, 1H), 6.90 (d, J=8.7 Hz, 2H), 6.29 (d, J=3.5 Hz, 1H), 6.26 (d, J=3.5 Hz, 1H), 5.79 (d, J=8.1 Hz, 1H), 4.98 (s, 2H), 4.10 (t, J=5.7 Hz, 2H), 3.97 (t, J=6.5 Hz, 2H), 2.67 (t, J=7.0 Hz, 2H), 2.30-2.00 (m, 2H), 1.80-1.60 (m, 2H), 1.50-1.20 (m, 4H), 0.94 (t, J=7.0 Hz, 3H); IR (ATR) 3298, 3142, 2931, 2869, 2679, 2245, 1660, 1571, 1486, 1270, 1245, 1176, 1036, 834, 758, 718 cm$^{-1}$; ESI MS m/z 529 [C$_{31}$H$_{33}$ClN$_4$O$_2$+H]$^+$; HPLC (Method 1) 98.6% (AUC), t$_R$=16.73 min. Anal. Calcd for C$_{31}$H$_{33}$ClN$_4$O$_2$·HCl·0.5H$_2$O: C, 64.81; H, 6.14; N, 9.75. Found: C, 64.65; H, 5.99; N, 9.54.

EXAMPLES 44-47

Preparation of 1-(2-Amino-6-pyridinylmethyl)-2,5-iphenylpyrrole Derivatives

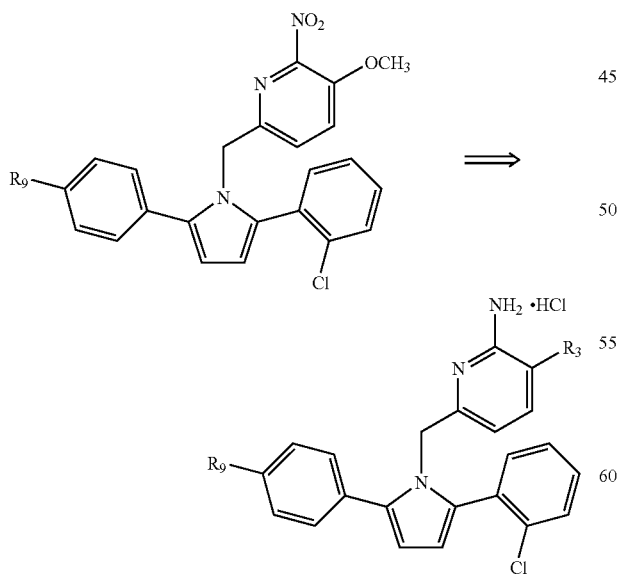

Using essentially the same procedures described hereinabove in Examples 44 and 45 and employing the appropriate substrate and suitable haloalkanol or aminoalkanol, the compounds shown on Table IV were obtained and identified by HNMR and mass spectral analyses.

TABLE IV

| Ex. No. | R3 | R9 | mp ° C. | Ms m/z |
|---|---|---|---|---|
| 44 | NH(CH$_2$)$_3$OH | OC$_5$H$_{11}$-n | 87-93 | 519 |
| 45 | NH(CH$_2$)$_2$OH | OC$_5$H$_{11}$-n | 95-100 | 505 |
| 46 | O(CH$_2$)$_2$OH | OC$_5$H$_{11}$-n | 78-81 | 514 |
| 47* | O(CH$_2$)$_2$OH | Br | 80-82 | 498 |

*Free amine

EXAMPLE 48

Preparation of {4-[1-(6-Amino-pyridin-2-ylmethyl)-5-(2-chloro-phenyl)-1H-pyrrol-2-yl]-phenyl}-pyrimidin-5-yl-amine

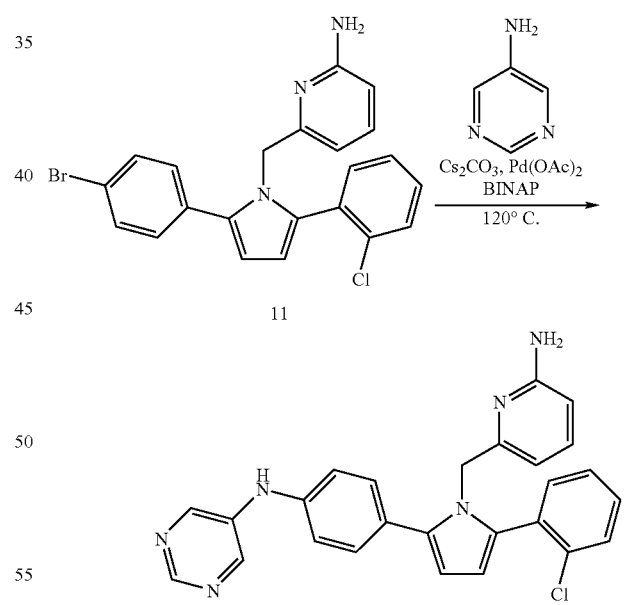

A mixture of 11 (0.269 g, 0.613 mmol) and cesium carbonate (0.200 g, 0.613 mmol) in toluene (40 mL) was degassed and treated with 5-aminopyrimidine (0.058 g, 0.613 mmol), palladium(II) acetate (0.014 g, 0.061 mmol), and racemic-2,2'-bis(diphenylphosphino)-1,1'-binaphthyl (0.057 g, 0.092 mmol). The reaction was degassed again and heated at 120° C. in a sealed tube overnight. The reaction was then cooled to room temperature and concentrated. Purification of the residue by flash chromatography (silica, 96:4 methylene chloride/methanol) and then by preparative HPLC (Method 3) afforded the title compound 0.060 g (22%) as an off-white solid: $R_f$ 0.32 (95:5 methylene chloride/methanol); mp 88-90° C.; $^1$H NMR (300 MHz, CD$_3$OD) δ 8.56 (s, 1H), 8.52 (s, 2H), 7.46-7.13 (m, 9H), 6.32 (d, J=3.6 Hz, 1H), 6.25 (d, J=7.1 Hz, 1H), 6.24 (d, J=3.6 Hz, 1H), 5.65 (d, J=7.1 Hz, 1H), 4.94 (s, 2H); IR (ATR) 3472, 3316, 3041, 1611, 1571, 1528, 1460, 1417, 1315, 1159, 754, 718 cm$^{-1}$; ESI MS m/z 453 [C$_{26}$H$_{21}$ClN$_6$+H]$^+$; HPLC (Method 1)>99% (AUC), $t_R$=11.96 min. Anal. Calcd for C$_{26}$H$_{21}$ClN$_6$·1.5H$_2$O: C, 65.06; H, 5.04; N, 17.51. Found: C, 64.83; H, 4.32; N, 16.97

EXAMPLE 49

Preparation of 6-{2-(2-Chlorophenyl)-5-[4-(pyrimidin-5-yloxy)phenyl]pyrrol-1-ylmethyl}-3-methoxy-2-nitropyridine

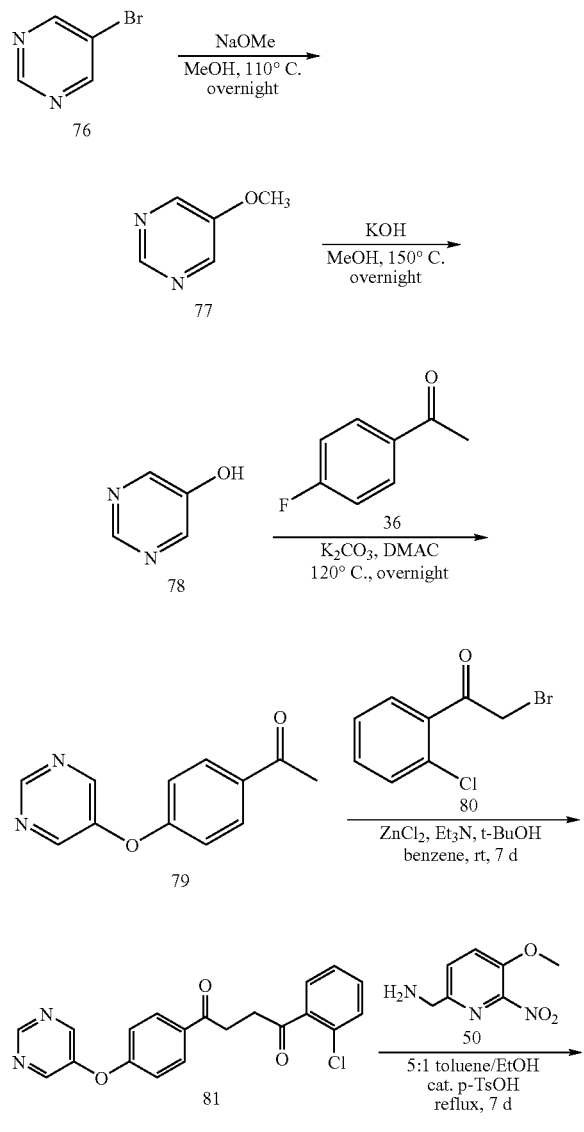

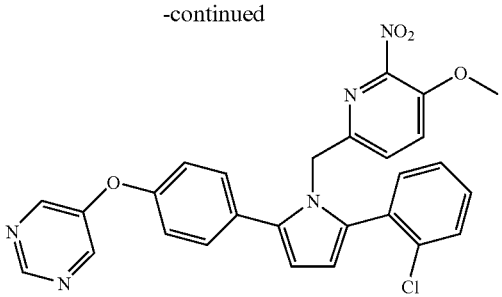

Step 1: Preparation of Intermediate 77

Sodium (1.45 g, 63.0 mmol) was added portionwise to methanol (100 mL) and stirred at room temperature until a homogeneous solution was obtained. The solution was then treated with 5-bromopyrimidine 76 (5.00 g, 31.4 mmol) and heated in a sealed tube at 110° C. overnight. The mixture was cooled to room temperature, concentrated under reduced pressure at a temperature <40° C. to a volume of ~20 mL, diluted with water (20 mL) and then extracted with methylene chloride (3×50 mL). The combined organic layers were dried over magnesium sulfate, filtered and concentrated to afford 77 (2.99 g, 86%) as a white solid: $^1$H NMR (300 MHz, CDCl$_3$) δ 8.86 (s, 1H), 8.42 (s, 2H), 3.93 (s, 3H).

Step 2: Preparation of Intermediate 78

A mixture of 77 (2.99 g, 27.2 mmol) and powdered potassium hydroxide (8.96 g of 85%, 136 mmol) in methanol (50 mL) was heated in a sealed tube at 150° C. overnight. The mixture was cooled to room temperature, neutralized by the addition of acetic acid and concentrated under reduced pressure. The residue obtained was triturated with hot acetonitrile (2×100 mL) and the acetonitrile extracts concentrated under reduced pressure to afford 7.51 g of an off-white solid. This solid was triturated with hot ethyl acetate (100 mL) and the ethyl acetate extract concentrated under reduced pressure to afford 1.81 g of an off-white solid. Further purification by flash chromatography (silica, 9:1 methylene chloride/methanol) afforded 78 (1.11 g, 43%) as an off-white solid: $^1$H NMR (300 MHz, DMSO-d$_6$) δ 10.45 (br s, 1H), 8.67 (s, 1H), 8.34 (s, 2H).

Step 3: Preparation of Intermediate 79

A mixture of 4'-fluoroacetophenone (0.36 g, 2.60 mmol), 78 (0.25 g, 2.60 mmol) and potassium carbonate (0.43 g, 3.12 mmol) in dimethylacetamide (2.5 mL) was heated at 120° C. overnight. The mixture was cooled to room temperature and diluted with water (25 mL) and ethyl acetate (25 mL). The organic layer was separated, washed with brine (25 mL), dried over magnesium sulfate, filtered and concentrated. Purification by flash chromatography (silica, 1:1 ethyl acetate/hexanes) afforded 79 (0.21 g, 38%) as a white solid: $^1$H NMR (300 MHz, CDCl$_3$) δ 9.07 (s, 1H), 8.56 (s, 2H), 8.02 (dd, J=6.9, 1.8 Hz, 2H), 7.09 (dd, J=6.9, 1.8 Hz, 2H), 2.63 (s, 3H); ESI MS m/z 215 [C$_{12}$H$_{10}$N$_2$O$_2$+H]$^+$.

Step 4: Preparation of Intermediate 81

Zinc chloride (1.73 g, 12.7 mmol) was dried under vacuum at 200° C. for 30 min. After cooling to room temperature, benzene (6.5 mL), triethylamine (0.96 g, 9.52 mmol), then t-butanol (0.70 g, 9.52 mmol) were added and the mixture stirred at room temperature. After 1.5 h, 79 (1.36 g, 6.35 mmol) and 2-chlorophenacylbromide 80 (1.48 g, 6.35 mmol) were added and stirring continued at room temperature for 7 d. The reaction was diluted with ethyl acetate (100 mL) and water (50 mL). The organic layer was separated and washed with brine (50 mL), dried over magnesium sulfate, filtered and concentrated. Purification by flash chromatography (silica, 1:1 ethyl acetate/hexanes) afforded 1.24 g of a yellow solid, which was a 6:4 mixture of 81 and 79 as determined by $^1$H NMR analysis. This material was used in the subsequent step without further purification.

Step 5: Preparation of 6-{2-(2-Chlorophenyl)-5-[4-(pyrimidin-5-yloxy)phenyl]pyrrol-1-ylmethyl}-3-methoxy-2-nitropyridine A mixture of 81 (1.23 g of ~60% purity), 50 (0.61 g, 3.35 mmol) and p-toluenesulfonic acid monohydrate (0.032 g, 0.168 mmol) in 5:1 toluene/ethanol (90 mL) was heated at reflux for 7 d. The mixture was cooled and concentrated. Purification by flash chromatography (silica, 1:1 ethyl acetate/hexanes) afforded the title product (0.46 g, 14% over 2 steps) as a yellow solid: $^1$H NMR (300 MHz, CDCl$_3$) δ 9.00 (s, 1H), 8.51 (s, 2H), 7.42-7.37 (m, 3H), 7.29-7.24 (m, 4H), 7.04 (d, J=8.7 Hz, 2H), 6.52 (d, J=8.6 Hz, 1H), 6.40 (m, 2H), 5.16 (s, 2H), 3.87 (s, 3H); ESI MS m/z 514 [C$_{27}$H$_{20}$ClN$_5$O$_4$+H]$^+$.

EXAMPLE 50

Preparation of 2-(2-Amino-6-{2-(2-chloro-phenyl)-5-[4-(pyrimidin-5-yloxy)-phenyl]-pyrrol-1-ylmethyl}-pyridin-3-yloxy)-ethanol

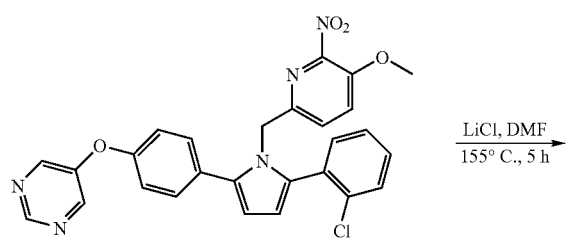

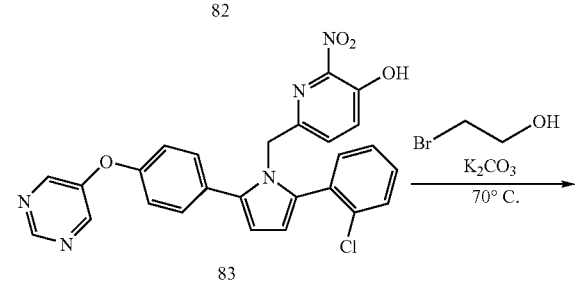

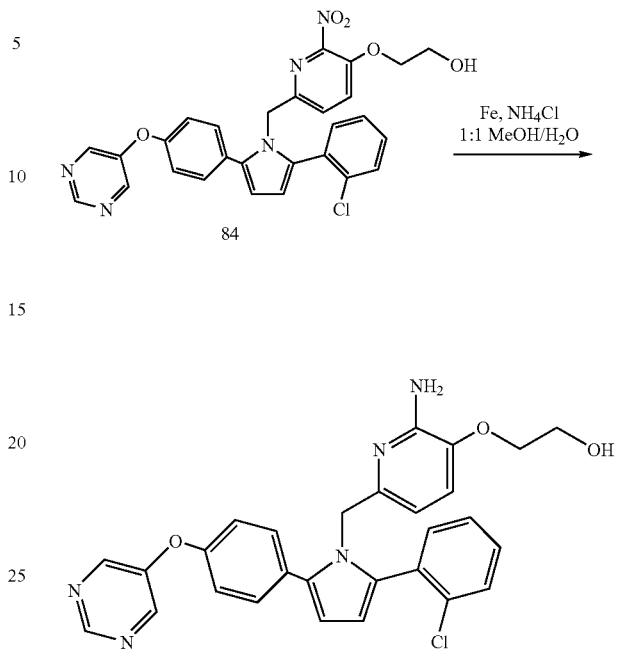

Step 1: Preparation of Intermediate 83

A mixture of 82 (0.150 g, 0.292 mmol) and lithium chloride (0.014 g, 0.321 mmol) in dimethylformamide (3.0 mL) was heated at 155° C. for 5 h. The reaction was cooled to room temperature and diluted with ethyl acetate (300 mL) and 1 N HCl (100 mL). The organic layer was separated and washed with brine (2×50 mL), dried over sodium sulfate, filtered and concentrated to afford 83 (0.150 g, 100%) as a yellow oil: $^1$H NMR (500 MHz, CDCl$_3$) δ 8.91 (s, 1H), 8.41 (s, 2H), 7.37-6.96 (m, 9H), 6.47 (d, J=9.0 Hz, 1H), 6.35 (d, J=3.5 Hz, 1H), 6.30 (d, J=3.5 Hz, 1H), 5.12 (s, 2H); ESI MS m/z 500 [C$_{26}$H$_{18}$ClN$_5$O$_4$+H]$^+$.

Step 2: Preparation of Intermediate 84

A mixture of 83 (0.150 g, 0.300 mmol), potassium carbonate (0.062 g, 0.450 mmol) and 2-bromoethanol (0.056 g, 0.450 mmol) in dimethyl sulfoxide (5 mL) was heated at 70° C. for 3.5 h. The reaction was then cooled to room temperature and diluted with ethyl acetate (100 mL) and water (30 mL). The organic layer was separated and washed with brine (3×20 mL), dried over sodium sulfate, filtered and concentrated. Purification by flash chromatography (silica, 7:3 hexanes/ethyl acetate) afforded 84 (0.11 g, 67%) as a yellow oil: $^1$H NMR (300 MHz, CD$_3$OD) δ 8.90 (s, 1H), 8.53 (s, 2H), 7.60-7.11 (m, 9H), 6.63 (d, J=8.4 Hz, 1H), 6.35 (d, J=3.6 Hz, 1H), 6.27 (d, J=3.6 Hz, 1H), 5.11 (s, 2H), 4.13 (d, J=4.8 Hz, 2H), 3.81 (d, J=4.8 Hz, 2H); ESI MS m/z 544 [C$_{28}$H$_{22}$ClN$_5$O$_5$+H]$^+$.

Step 3: Preparation of 2-(2-Amino-6-{2-(2-chloro-phenyl)-5-[4-(pyrimidin-5-yloxy)-phenyl]-pyrrol-1-ylmethyl}-pyridin-3-yloxy)-ethanol The reduction of 84 was performed as described in method A. Purification by flash chromatography (silica, 97.5:2.5 to 90:10 methylene chloride/methanol) afforded the title compound (0.10 g, 96%) as a white solid: $R_f$ 0.36 (95:5 methylene chloride/methanol); mp 78-81° C.; $^1$H NMR (300 MHz, CD$_3$OD) δ 8.90 (s, 1H), 8.52 (s, 2H), 7.47-7.09 (m, 8H), 6.82 (d, J=8.1 Hz, 1H), 6.35 (d, J=3.6 Hz, 1H), 6.24 (d, J=3.6 Hz, 1H), 5.65 (d, J=8.1 Hz, 1H), 4.90 (s, 2H), 3.95 (t, J=4.2 Hz, 2H), 3.83 (t, J=4.2 Hz, 2H); IR (ATR) 3338, 2924, 1615, 1560, 1475, 1407, 1251, 1185, 1035, 757, 717 cm$^{-1}$; ESI MS m/z 514 [C$_{28}$H$_{24}$ClN$_5$O$_3$+H]$^+$; HPLC (Method 1) 95.1% (AUC), $t_R$=12.16 min. Anal. Calcd for C$_{28}$H$_{24}$ClN$_5$O$_3$.0.25H$_2$O: C, 64.86; H, 4.76; N, 13.51. Found: C, 64.73; H, 4.57; N, 13.14.

EXAMPLE 51

Preparation of 2-(2-Amino-6-{2-(2-chloro-phenyl)-5-[4-(pyrimidin-5-yloxy)-phenyl]-pyrrol-1-ylmethyl}-pyridin-3-ylamino)-ethanol

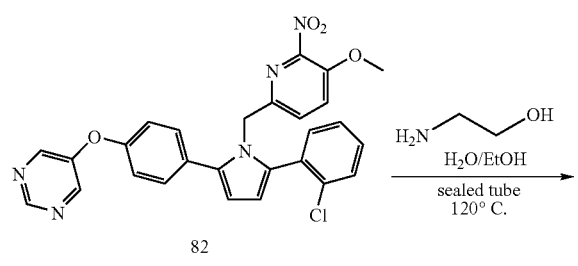

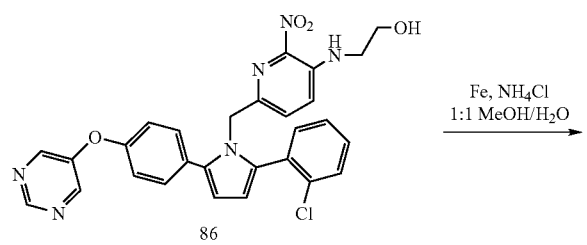

Step 1: Preparation of Intermediate 86

A mixture of 82 (0.150 g, 0.292 mmol), ethanolamine (1.0 mL), water (2.0 mL) and ethanol (2.0 mL) was heated at 120° C. in a sealed tube for 6 h. The reaction was cooled to room temperature, concentrated and diluted with ethyl acetate (100 mL) and water (30 mL). The organic layer was separated and washed with brine (2×20 mL), dried over sodium sulfate, filtered and concentrated. Purification by flash chromatography (silica, 1:9 ethyl acetate/hexanes) afforded 0.10 g of a yellow oil which was a 2:1 mixture of 86 and the nitro displacement by-product as determined by $^1$H NMR analysis. This material was used in the subsequent step without further purification.

Step 2: Preparation of 2-(2-Amino-6-{2-(2-chloro-phenyl)-5-[4-(pyrimidin-5-yloxy)-phenyl]-pyrrol-1-ylmethyl}-pyridin-3-ylamino)-ethanol The reduction of 86 was performed essentially as described in Example 40, step 5. Purification by flash chromatography (silica, 95:5 methylene chloride/methanol) afforded the title compound, (0.060 g) as an off-white solid: $R_f$ 0.23 (95:5 methylene chloride/methanol); mp 78-82° C.; $^1$H NMR (300 MHz, CD$_3$OD) δ 8.90 (s, 1H), 8.51 (s, 2H), 7.46-7.08 (m, 8H), 6.60 (d, J=8.1 Hz, 1H), 6.35 (d, J=3.6 Hz, 1H), 6.23 (d, J=3.6 Hz, 1H), 5.70 (d, J=8.1 Hz, 1H), 4.90 (s, 2H), 3.71 (t, J=5.6 Hz, 2H), 3.13 (t, J=5.6 Hz, 2H); IR (ATR) 3349, 2924, 1676, 1580, 1560, 1481, 1407, 1252, 1200, 757, 717 cm$^{-1}$; ESI MS m/z 513 [C$_{28}$H$_{25}$ClN$_6$O$_2$+H]$^+$; HPLC (Method 1)>99% (AUC), $t_R$=12.16 min. Anal. Calcd for C$_{28}$H$_{25}$ClN$_6$O$_2$.1.25H$_2$O: C, 62.80; H, 5.18; N, 15.69. Found: C, 63.05; H, 4.76; N, 14.82.

EXAMPLE 52

Preparation of Pentanoic acid {4-[1-(6-amino-pyridin-2-ylmethyl)-5-(2-chlorophenyl)-1H-pyrrol-2-yl]-phenyl}-amide

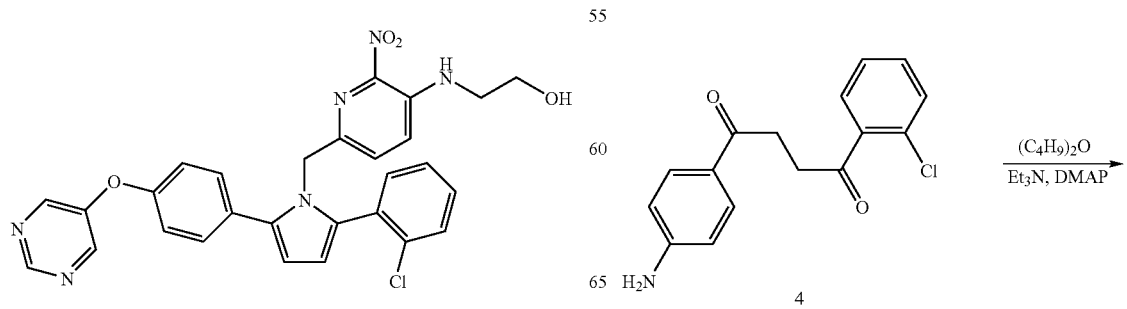

-continued

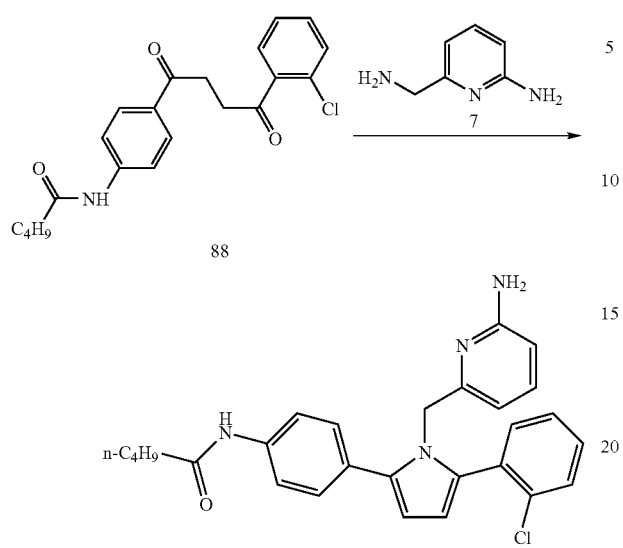

Step 1: Preparation of Intermediate 88

A mixture of 4 (0.20 g, 0.695 mmol), valeric anhydride (0.155 g, 0.834 mmol), triethylamine (0.084 g, 0.834 mmol) and 4-dimethylaminopyridine (0.085 g, 0.695 mmol) in tetrahydrofuran (5 mL) was heated at 50° C. for 4 h. The reaction was cooled to room temperature and concentrated. Purification by flash chromatography (silica, 1:9 to 1:1 ethyl acetate/hexanes) afforded 88 (0.22 g, 85%) as a white solid: $^1$H NMR (500 MHz, CDCl$_3$) δ 7.93 (m, 3H), 7.65 (m, 3H), 7.47-7.33 (m, 3H), 3.45-3.42 (m, 2H), 3.38-3.35 (m, 2H), 2.36 (t, J=7.5 Hz, 2H), 1.70 (m, 2H), 1.35 (m, 2H), 0.95 (t, J=7.3 Hz, 3H); ESI MS m/z 372 [C$_{21}$H$_{22}$ClNO$_3$+H]$^+$.

Step 2: Preparation of Pentanoic acid {4-[1-(6-amino-pyridin-2-ylmethyl)-5-(2-chloro-phenyl)-1H-pyrrol-2-yl]-phenyl}-amide A mixture of 88 (0.22 g, 0.592 mmol), 7 (0.073 g, 0.592 mmol) and p-toluenesulfonic acid monohydrate (0.011 g, 0.059 mmol) in 5:1 toluene/ethanol (6 mL) was heated at 120° C. overnight. The mixture was cooled and concentrated. Purification by flash chromatography (silica, 1:1 ethyl acetate/hexanes) afforded the title compound (0.161 g, 59%) as a white solid: R$_f$ 0.09 (97.5:2.5 methylene chloride/methanol); mp 145-150° C.; $^1$H NMR (500 MHz, CD$_3$OD) δ 7.54-7.15 (m, 9H), 6.31 (d, J=3.6 Hz, 1H), 6.25 (d, J=7.2 Hz, 1H), 6.24 (d, J=3.6 Hz, 1H), 5.63 (d, J=7.2 Hz, 1H), 4.91 (s, 2H), 2.36 (t, J=7.8 Hz, 2H), 1.66 (m, 2H), 1.39 (m, 2H), 0.96 (t, J=7.2 Hz, 3H); IR (ATR) 3385, 3174, 2956, 2929, 1658, 1596, 1528, 1463, 1307, 1184, 837, 756, 720 cm$^{-1}$; ESI MS m/z 459 [C$_{27}$H$_{27}$ClN$_4$O+H]$^+$; HPLC (Method 1)>99% (AUC), t$_R$=13.19 min. Anal. Calcd for C$_{27}$H$_{27}$ClN$_4$O: C, 69.29; H, 6.03; N, 11.97. Found: C, 69.68; H, 5.93; N, 11.63.

EXAMPLE 53

Preparation of 6-[2-(2-Chloro-phenyl)-5-(4-pentylamino-phenyl)-pyrrol-1-ylmethyl]-pyridin-2-ylamine hydrochloride

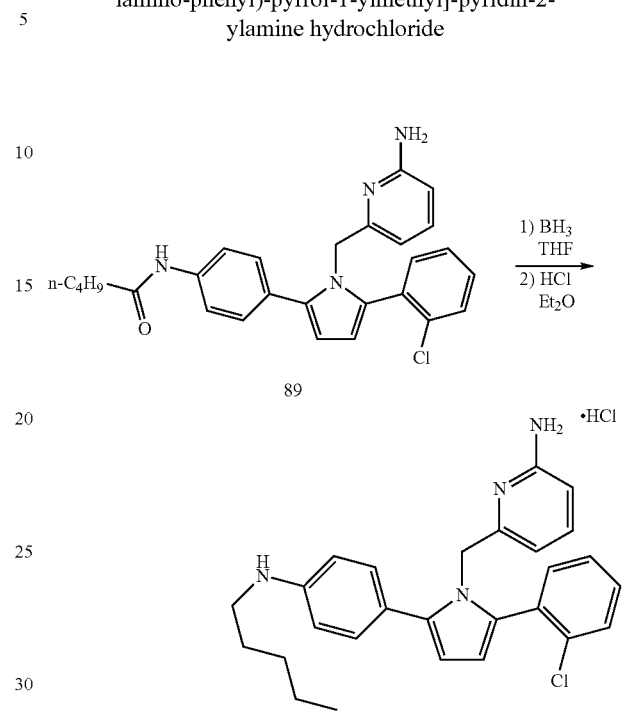

A mixture of 89 (0.060 g, 0.131 mmol) and borane-tetrahydrofuran complex (0.66 mL of a 1.0 M solution in tetrahydrofuran, 0.66 mmol) in tetrahydrofuran (10 mL) was stirred at room temperature for 5 h then heated at reflux overnight. The reaction was cooled to room temperature and HCl (8 mL of a 6.0 M solution in water, 4.80 mmol) was added dropwise. The mixture was then heated at reflux for 2 h, cooled to room temperature, neutralized with sodium bicarbonate solid (4.03 g, 4.80 mmol) and concentrated. Purification by flash chromatography (silica, 3:1 ethyl acetate/hexanes, then 100:0 to 99:1 methylene chloride/methanol) afforded the free amine of the title product (0.022 g, 38%) as a light yellow syrup: $^1$H NMR (300 MHz, CDCl$_3$) δ 7.39-7.10 (m, 8H), 6.55 (m, 2H), 6.29 (s, 2H), 6.18 (d, J=7.8 Hz, 1H), 5.75 (d, J=7.8 Hz, 1H), 4.98 (s, 2H), 4.20 (s, 2H), 3.09 (t, J=6.9 Hz, 2H), 1.61 (m, 2H), 1.25-1.46 (m, 4H), 0.91 (t, J=7.2 Hz, 3H); ESI MS m/z 445 [C$_{27}$H$_{29}$ClN$_4$+H]$^+$.

The conversion of the free amine to the hydrochloride salt was performed exxentially as described in Example 31 to afford 91 (0.025 g, 100%) as an off-white solid: R$_f$ 0.33 (2:1 hexanes/ethyl acetate); mp 145-147° C.; $^1$H NMR (300 MHz, CD$_3$OD) δ 7.67-7.19 (m, 9H), 6.69 (d, J=8.0 Hz, 1H), 6.47 (s, 1H), 6.37 (s, 1H), 5.87 (d, J=8.0 Hz, 1H), 5.13 (s, 2H), 3.30 (m, 2H), 1.85 (m, 2H), 1.45-1.35 (m, 4H), 0.96 (t, J=7.3 Hz, 3H); IR (ATR) 3295, 3088, 2858, 2669, 2461, 1660, 1627, 1486, 1387, 1345, 1170, 994, 760 cm$^{-1}$; ESI MS m/z 445 [C$_{27}$H$_{29}$ClN$_4$+H]$^+$; HPLC (Method 1) 98.8% (AUC), t$_R$=12.94 min. Anal. Calcd for C$_{27}$H$_{29}$ClN$_4$.2HCl.1.5H$_2$O: C, 59.51; H, 6.29; N, 10.28. Found: C, 60.10; H, 5.97; N, 9.69.

EXAMPLE 54
Preparation of 2-[(2-amino-6-{[2-(2-chlorophenyl)-5-(4-propoxyphenyl)-1H-pyrrol-1-yl]methyl}pyridine-3-yl)oxy]ethanol
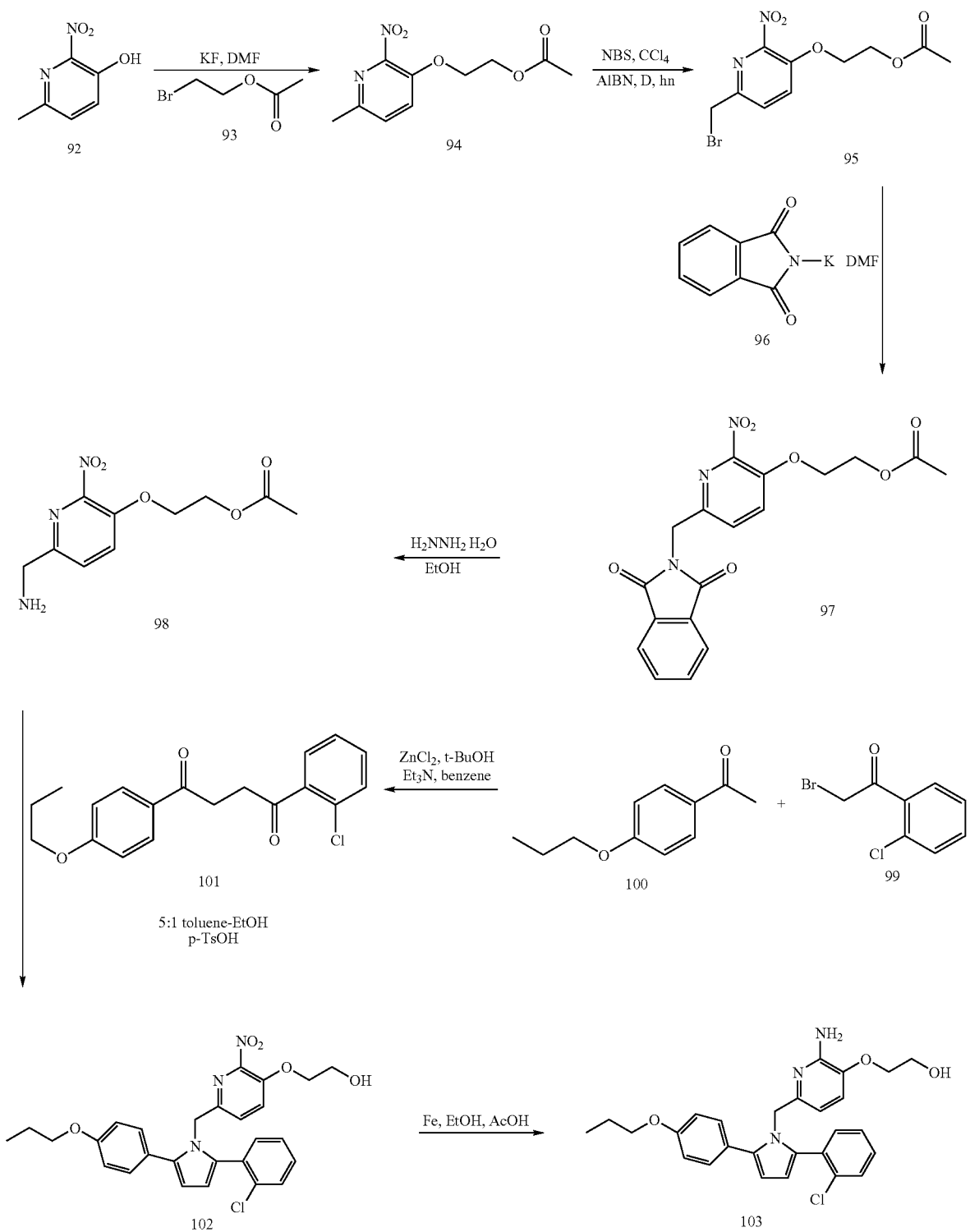

Step 1: Preparation of 1-(2-Chlorophenyl)-4-(4-propoxyphenyl)-butane-1,4-dione (intermediate 101)

To a solution of 11.7 gm (85.6 mmol) of fused $ZnCl_2$ in 20 mL of benzene was 10 added 8.50 mL (64 mmol) of triethylamine and 6.12 mL (64 mmol) of dry t-butanol. After dissolution at room temperature 11.45 gm (64 mmol) of 1-(4-propoxyphenyl) ethanone 100 and 10.0 gm (42.8 mmol) of 2-bromo-1-(2-chlorophenyl) ethanone 99. The mixture was allowed to stir at room temperature for 6 days. The solvents were removed at reduced pressure and the residue added to 100 mL of water. The aqueous phase was extracted with ethyl acetate (200 mL) twice. The combined organic layers were washed with water (150 mL), saturated brine, dried ($Na_2SO_4$) and the solvents removed at reduced pressure. Column chromatography of the residue using 2%-4%-8% ethyl acetate-hexanes yielded 5.3 gm (37%) of a light yellow solid. This was recrystallized from hot hexanes-ethyl acetate. $^1H$ NMR (400 MHz, $CDCl_3$) δ: 1.04 (t, 3H, J=7.42 Hz), 1.82 (m, 2H), 3.36 (m, 2H), 3.42 (m, 2H), 3.98 (t, 2H, J=6.5 Hz), 6.92 (d, 2H J=8.9 Hz), 7.38 (m, 3H), 7.64 (m, 1H), 7.97 (m, 2H).

Step 2: Preparation of Acetic acid 2-(6-methyl-2-nitro-pyridin-3-yloxy)-ethyl ester (Intermediate 94)

To a solution of 5.0 gm (32.4 mmol) of 3-hydroxy-6-methyl-2-nitropyridine 1 in 90 mL of DMF was added 5.65 gm (97.3 mmol) of KF and the solution was allowed to stir at room temperature for 1 h. To the solution was added 5.95 gm (35.6 mmol) acetic acid 2-bromo ethyl ester 93. The heterogeneous mixture was allowed to stir at room temperature for 72 h. The solution was poured into 200 mL of water and extracted twice (300 mL) with EtOAc. The combined organic layers were washed twice (300 mL) with water, saturated brine and then dried (anhydrous Na2SO4) and the solvents removed under reduced pressure. Column chromatography of the residue using 10%-20% EtOAc-hexanes as an eluent yielded 4.5 gm (58% yield) of a yellow oil. $^1H$ NMR (400 MHz, $CDCl_3$) δ: 2.07 (s, 3H), 2.52 (s, 3H), 4.28 (t, 2H, J=4.8 Hz), 4.40 (t, 2H, J=4.8 Hz), 7.35 (d, 2H, J=8.5 Hz), 7.4 (d, 2H J=8.5 Hz).

Step 3: Preparation of Acetic Acid 2-(6-bromomethyl-2-nitro-pyridin-3-yloxy)-ethyl ester (intermediate 95)

To a solution of 2.16 gm (9.0 mmol) of acetic acid 2-(6-methyl-2-nitro-pyridin-3-yloxy)-ethyl ester 94, 1.76 gm (9.9 mmol) of N-bromosuccinimide in 125 mL of $CCl_4$ was added 0.074 gm (44.9 μmol) of AIBN and the reaction was heated to reflux for 1 h. After 1 h a 500 watt sun lamp was used to irradiate the refluxing solution for an additional 4 h. The mixture was poured into 300 mL of $CCl_4$ and washed with water twice (150 mL), saturated brine and the organic layer was dried (anhydrous Na2SO4) and the solvents removed at reduced pressure. Column chromatography of the residue using 50%-30%-10% $CH_2Cl_2$-hexanes yielded 1.06 gm (37%) of a light yellow solid. $^1H$ NMR (400 MHz, $CDCl_3$) δ: 2.06 (s, 3H), 4.31 (t, 2H, J=4.1 Hz), 4.41 (t, 2H, J=4.1 Hz), 4.48 (s, 2H), 7.49 (d, 2H, J=8.5 Hz), 7.65 (d, 2H J=8.5 Hz).

Step 4: Preparation of Acetic acid 2-[6-(1,3-dioxo-1,3-dihydro-isoindol-2-ylmethyl)-nitro-pyridin-3-yloxy]-ethyl ester (intermediate 97)

To a solution of 0.31 gm (0.97 mmol) in 7 mL of DMF was added 0.189 gm (1.02 mmol) of potassium phthalimide 96 and the solution was allowed to stir at room temperature for 18 h. The solid was filtered and washed with hexanes to yield 0.35 gm (94%) of a white solid. $^1H$ NMR (400 MHz, $CDCl_3$) δ: 2.03 (s, 3H), 4.26 (m, 2H), 4.37 (m, 2H), 4.94 (s, 3H), 7.44 (d, 2H, J=8.6 Hz), 7.48 (d, 2H J=8.6 Hz), 7.72 (m, 2H), 7.85 (m, 2H).

Step 5: Preparation of Acetic acid 2-(6-aminomethyl-2-nitropyridin-3-yloxy)-ethyl ester (Intermediate 98)

To a solution of 0.35 gm (0.97 mmol) of Acetic acid 2-[6-(1,3-dioxo-1,3-dihydro-isoindol-2-ylmethyl)-nitro-pyridin-3-yloxy]-ethyl ester 97 in 5 mL of ethanol was added 0.051 mL (1.01 mmol) of hydrazine hydrate at room temperature. The reaction mixture was allowed to stir for 4 h. The mixture was then transferred with ethyl acetate and the solvent was removed at reduced pressure. The residue was taken up in $CHCl_3$ (200 mL) and washed twice with water (100 mL), saturated brine, dried ($Na_2SO_4$), and the solvents removed under reduced pressure. This was used without further purification or characterization.

Step 6: Preparation of 2-{6-[2-(2-Chlorophenyl)-5-(4-propoxyphenyl)-pyrrol-1ylmethyl]-2-nitro-pyridin-3-yloxy}-ethanol (Intermediate 102)

To a solution of 0.2 gm of acetic acid 2-(6-aminomethyl-2-nitropyridin-3-yloxy)-ethyl ester (0.8 mmol) in 3 mL of 5:1 toluene-ethanol was added 0.20 gm of 1-(2-chlorophenyl)-4-(4-propoxyphenyl)-butane-1,4-dione and 10 mg of p-TsOH. The reaction mixture stirred at 100° C. for 72 h. The reaction mixture was poured into 200 mL of $CHCl_3$ and washed twice with water (100 mL), saturated brine, dried ($Na_2SO_4$), and the solvents removed under reduced pressure. The residue was purified by column chromatography using 4% methanol-chloroform as an eluent to give 100 mg (25% yield) of an oil. This was used without further purification or characterization.

Step 7: Preparation of 2-[(2-Amino-6-{[2-(2-chlorophenyl)-5-(4-propoxyphenyl)-1H-pyrrol-1-yl]methyl}pyridine-3-yl)oxy]ethanol To a solution of 0.1 gm (0.2 mmol) of 2-{6-[2-(2-Chlorophenyl)-5-(4-propoxyphenyl)-pyrrol-1ylmethyl]-2-nitro-pyridin-3-yloxy}-ethanol in 4 mL of 1:1 ethanol-acetic acid was added 0.55 gm of Fe powder. The reaction mixture was allowed to stir at 96° C. for 2 h. The mixture was cooled and poured in 100 mL of saturated $NaHCO_3$ and extracted twice with $CH_2Cl_2$. The combined organic layers were dried ($Na_2SO_4$) and the solvents removed under reduced pressure. The residue was purified by column chromatography using 1%-2% methanol-chloroform-0.5% Et3N as an eluent to yield 0.037 gm (39% yield) of a solid mp 89-92° C. $^1H$ NMR (500 MHz, $CDCl_3$) δ: 1.00 (t, 3H, J=7.4 Hz), 1.23 (br s, 3H), 1.77 (m, 2H), 3.88 (m, 4H), 3.98 (t, 2H, J=4.3 Hz), 4.99 (s, 2H), 5.65 (d, 1H, J=8.05 Hz), 6.29 (s, 2H), 6.72 (d, 1H, J=8.05 Hz), 6.84 (d, 1H, J=8.78 Hz), 7.21 (m, 2H), 7.25 (m, 3H), 7.36 (m, 1H); MS (ES) m/z 478.2 ([M+H]$^+$).

EXAMPLE 55

Preparation of 6-[(2,5-diphenyl-1H-pyrrol-1-yl)methyl]pyridin-2-amine

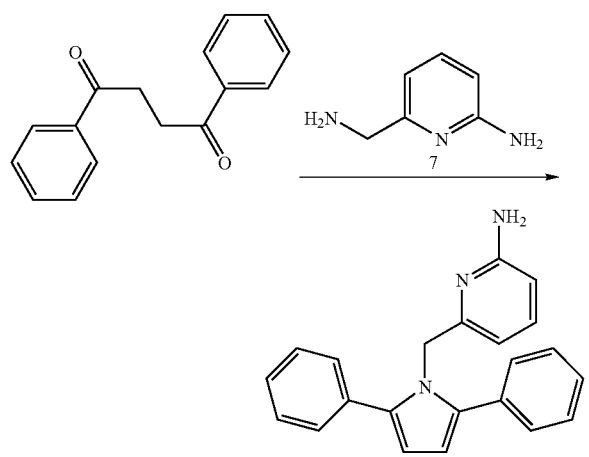

6-(Aminomethyl)pyridin-2-amine (0.050 g, 0.4 mmol) was dissolved in EtOH (2 mL) and Toluene (10 mL) was added. To this mixture was added pTSA (5 mg) and 1,4-diphenyl-1,4-butanedione (0.124 g, 0.4 mmol). The solution was heated to reflux overnight. The solvent was removed and the residue was purified by flash chromatography (20:1 CHCl3: MeOH) to yield 6-[(2,5-diphenyl-1H-pyrrol-1-yl)methyl]pyridin-2-amine as a white solid. mp 143-144° C.; $^1$H NMR (500 MHz, DMSO-$d_6$) δ: 5.06 (s, 2H), 5.50 (d, 1H, J=7.3 Hz), 5.82 (s, 2H), 6.16 (d, 1H, J=8.1 Hz), 6.34 (s, 2H), 7.18 (t, 1H, J=7.47 Hz), 7.28 (t, 2H, J=8.5 Hz), 7.36 (m, 4H), 7.40 (m, 4H); MS (ES) m/z 326.3.

EXAMPLES 56-67

Preparation of 6-[(2,5-diphenyl-1H-pyrrol-1-yl)methyl]pyridin-2-amine Derivatives

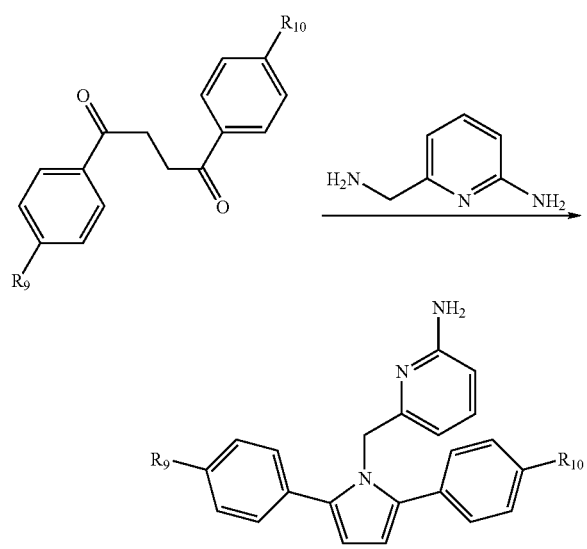

Using essentially the same procedure described in Example 55 and employing the appropriately substituted 1,4-diphenylbutanedione as reactant, the compounds shown on Table V were obtained and identified by HNMR and mass spectral analyses.

TABLE V

| Ex. No. | R9 | R10 | mp ° C. | Ms m/z |
|---|---|---|---|---|
| 56 | OCH$_2$CH$_2$CH$_3$ | H | 106-107 | 384.2 |
| 57 | CO$_2$C$_2$H$_5$ | F | 172-173 | 416.1 |
| 58 | CO$_2$C$_2$H$_5$ | H | 161-162 | 398.2 |
| 59 | CONH-cyclopropyl | H | 108-109 | 409.2 |
| 60 | CONH—C$_2$H$_5$ | H | 105-107 | 397.2 |
| 61 | CONH—C$_2$H$_5$ | F | 184-185 | 415.2 |
| 62 | CONH-i-C$_3$H$_7$ | H | 201-202 | 409.3 |
| 63 | CONH-n-C$_4$H$_9$ | H | 149-150 | 423.3 |
| 64 | CONH—CH$_2$CH=CH$_2$ | H | 150-151 | 409.17 |
| 65 | CONH-n-C$_3$H$_7$ | H | 88-89 | 411.2 |
| 66 | CONH$_2$-2-furylmethyl | H | 98-99 | 453.19 |
| 67 | CONH-cyclobutyl | H | 122-123 | 423.18 |

EXAMPLE 68

Evaluation of BACE-1 Binding Affinity of Test Compounds

Fluorescent Kinetic Assay

Final Assay Conditions: 10 nM human BACE1 (or 10 nM Murine BACE1), 25 μM substrate (WABC-6, MW 1549.6, from AnaSpec), Buffer: 50 mM Na-Acetate, pH 4.5, 0.05% CHAPS, 25% PBS, room temperature. Na-Acetate was from Aldrich, Cat. #24, 124-5, CHAPS was from Research Organics, Cat. # 1304C 1×, PBS was from Mediatech (Cellgro), Cat #21-031-CV, peptide substrate AbzSEVNLDAEFRDpa was from AnaSpec, Peptide Name: WABC-6

Determination of stock substrate (AbzSEVNLDAEFRDpa) concentration: ~25 mM stock solution is made in DMSO using the peptide weight and MW, and diluted to ~25 μM (1:1000) in 1×PBS. Concentration is determined by absorbance at 354 nm using an extinction coefficient ε of 18172 $M^{-1}$ $cm^{-1}$, the concentration of stock substrate is corrected, and the substrate stock stored in small aliquots in –80° C. [Substrate Stock]=ABS$^{354\ nm}$*10$^6$/18172 (in mM)

The extinction coefficient $\epsilon^{354\ nm}$ was adapted from TACE peptide substrate, which had the same quencher-fluorophore pair.

Determination of Stock Enzyme Concentration: the stock concentration of each enzyme is determined by absorbance at 280 nm using ε of 64150 $M^1$ $cm^{-1}$ for hBACE1 and MuBACE1 in 6 M Guanidinium Hydrochloride (from Research Organics, Cat. #5134G-2), pH~6. The extinction coefficient $\epsilon^{280\ nm}$ for each enzyme was calculated based on known amino acid composition and published extinction coefficients for Trp (5.69 $M^{-1}$ $cm^{-1}$) and Tyr (1.28 $M^{-1}$ $cm^{-1}$) residues (*Anal. Biochem.* 182, 319-326).

Dilution and mixing steps: total reaction volume: 100 μL
  2× inhibitor dilutions in buffer A (66.7 mM Na-Acetate, pH 4.5, 0.0667% CHAPS) were prepared, 4× enzyme dilution in buffer A (66.7 mM Na-Acetate, pH 4.5, 0.0667% CHAPS) were prepared, 100 μM substrate dilution in 1×PBS was prepared, and 50 μL 2× Inhibitor, 25 μL 100 μM substrate are added to each well of 96-well plate (from DYNEX Technologies, VWR #: 11311-046), immediately followed by 25 μL 4× enzyme (added to the inhibitor and substrate mix), and the fluorescence readings are initiated.

Fluorescence Readings: Readings at $\lambda_{ex}$ 320 nm and $\lambda_{em}$ 420 nm are taken every 40 sec for 30 min at room temperature and the linear slope for substrate cleavage rate ($v_i$) determined.

Calculation of % Inhibition:

$$\%\text{Inhibition} = 100*(1 - v_i/v_0)$$

$v_i$: substrate cleavage rate in the presence of inhibitor $v_0$: substrate cleavage rate in the absence of inhibitor $IC_{50}$ Determination:

$$\%\text{Inhibition} = ((B*IC_{50}^n) + (100*I_0^n))/(IC_{50}^n + I_0^n)$$

(Model #39 from LSW Tool Bar in Excel where B is the % inhibition from the enzyme control, which should be close to 0.) % Inhibition is plotted vs. Inhibitor Concentration ($I_0$) and the data fit to the above equation to obtain $IC_{50}$ value and Hill number (n) for each compound. Testing at least 10 different inhibitor concentrations is preferred. The data obtained are shown in Table VI below.

TABLE VI

| Ex. No. | BACE 1 $IC_{50}$ μM |
|---|---|
| 1 | D |
| 2 | D |
| 3 | D |
| 4 | C |
| 5 | C |
| 6 | D |
| 14 | C |
| 15 | C |
| 16 | B |
| 17 | D |
| 18 | B |
| 19 | B |
| 20 | C |
| 23 | B |
| 24 | B |
| 26 | B |
| 27 | D |
| 28 | B |
| 29 | B |
| 30 | D |
| 31 | C |
| 32 | B |
| 33 | B |
| 34 | B |
| 35 | B |
| 36 | A |
| 37 | B |
| 38 | D |
| 40 | D |
| 41 | D |
| 42A | D |
| 42B | D |
| 43A | D |
| 43B | D |
| 44 | B |
| 45 | B |
| 46 | B |
| 47 | B |
| 48 | B |
| 50 | A |

TABLE VI-continued

| Ex. No. | BACE 1 $IC_{50}$ μM |
|---|---|
| 51 | A |
| 52 | C |
| 53 | C |
| 54 | B |
| 55 | D |
| 56 | C |
| 57 | D |
| 58 | D |
| 59 | C |
| 60 | C |
| 61 | C |
| 62 | B |
| 63 | C |
| 64 | B |
| 65 | C |
| 66 | D |
| 67 | C |

A = 0.01 μM-0.10 = μM
B = 0.11 μM-1.00 = μM
C = 1.10 μM-5.0 = μM
D = >5.0 μM-0.10 = μM

What is claimed is:

1. A compound of formula Ia

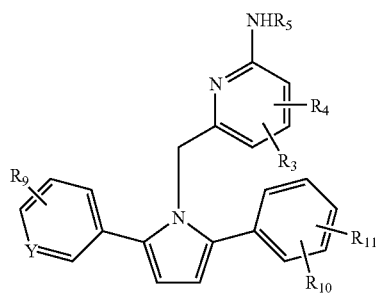

or a pharmaceutically acceptable salt thereof
wherein
Y is CH;
$R_3$ and $R_4$ are each independently H, halogen, $NR_6R_7$, $OR_8$, or an alkyl, haloalkyl or aryl group each group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;
$R_5$ is H or an alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;
$R_6$ and $R_7$ are each independently H or an alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_8$ is H or alkyl or alkenyl each substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_9$ is $OR_{12}$;

$R_{10}$ and $R_{11}$ are each independently H, halogen, $OR_{13}$, or an alkyl or haloalkyl group each group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_{12}$ is pyrimidine group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl; and $R_{13}$ are each independently a H or an alkyl, aryl or group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl.

2. The compound according to claim 1, wherein $R_3$ is attached in the ring position ortho to the $NHR_5$ group and $R_4$ and $R_5$ are H.

3. The compound according to claim 1 wherein $R_{10}$ is H, halogen or an alkyl or alkoxy group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl; and $R_4$, $R_5$ and $R_{11}$ are H.

4. The compound according to claim 1 wherein $R_4$, $R_5$, and $R_{11}$ are H; $R_3$ is H, $OR_8$ or an alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl; $R_9$ is $OR_{12}$ and $R_{10}$ is H, halogen, $OR_{13}$ or an alkyl group substituted with 0-4 independently substituents selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl.

5. The compound according to claim 2 wherein $R_3$ is H or $OR_8$.

6. The compound according to claim 1 selected from the group consisting of:
  6-{2-(2-Chloro-phenyl)-5-[4-(pyrimidin-2-yloxy)-phenyl]-pyrrol-1-ylmethyl}-pyridin-2-ylamine;
  2-(2-Amino-6-{2-(2-chloro-phenyl)-5-[4-(pyrimidin-5-yloxy)-phenyl]-pyrrol-1-ylmethyl}-pyridin-3-yloxy)-ethanol; and
  2-(2-Amino-6-{2-(2-chloro-phenyl)-5-[4-(pyrimidin-5-yloxy)-phenyl]-pyrrol-1-ylmethyl}-pyridin-3-ylamino)-ethanol; or
a pharmaceutically acceptable salt thereof.

7. A pharmaceutical composition which comprises a pharmaceutically acceptable carrier and a compound of formula Ia

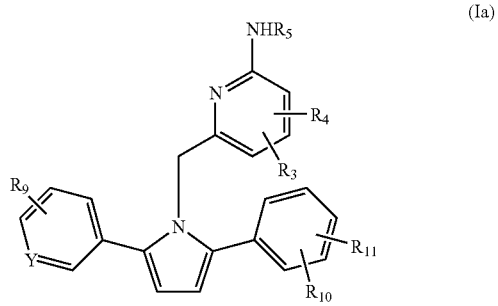

(Ia)

or a pharmaceutically acceptable salt thereof
wherein
Y is CH;

$R_3$ and $R_4$ are each independently H, halogen, $NR_6R_7$, $OR_8$, or an alkyl, haloalkyl or aryl group each group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_5$ is H or an alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_6$ and $R_7$ are each independently H or alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_8$ is H or alkyl or alkenyl each substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_9$ is $OR_{12}$, $R_{10}$ and $R_{11}$ are each independently H, halogen, $OR_{13}$, or an alkyl or haloalkyl group each group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl;

$R_{12}$ is pyrimidine group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl; and $R_{13}$ are each independently a H or an alkyl, aryl or group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl.

8. The composition according to claim 7 wherein in the compound of formula Ia, $R_4$, $R_5$, and $R_{11}$ are H; $R_3$ is H, $OR_8$ or an alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl; $R_9$ is $OR_{12}$, and $R_{10}$ is H, halogen, $OR_{13}$ or an alkyl group substituted with 0-4 substituents independently selected from the group consisting of halo, nitro, cyano, thiocyanato, cyanato, hydroxyl, alkyl, haloalkyl, alkoxy, haloalkoxy, amino, alkylamino, dialkylamino, formyl, alkoxycarbonyl, carboxyl, alkanoyl, alkylthio, alkylsuphinyl, alkylsulphonyl, carbamoyl, alkylamido, phenyl, phenoxy, benzyl, benzyloxy and cycloalkyl.

9. The composition according to claim 7 wherein the compound of formula Ia is selected from the group consisting of:
 6-{2-(2-Chloro-phenyl)-5-[4-(pyrimidin-2-yloxy)-phenyl]pyrrol-1-ylmethyl}-pyridin-2-ylamine;
 2-(2-Amino-6-{2-(2-chloro-phenyl)-5-[4-(pyrimidin-5-yloxy)-phenyl]pyrrol-1-ylmethyl}-pyridin-3-yloxy)-ethanol; and
 2-(2-Amino-6-{2-(2-chloro-phenyl)-5-[4-(pyrimidin-5-yloxy)-phenyl]-pyrrol-1-ylmethyl}-pyridin-3-ylamino)-ethanol; or
 a pharmaceutically acceptable salt thereof.

* * * * *